US011739166B2

(12) United States Patent
Greenawalt et al.

(10) Patent No.: US 11,739,166 B2
(45) Date of Patent: Aug. 29, 2023

(54) REACTIVE POLYSACCHARIDE-BASED HEMOSTATIC AGENT

(71) Applicant: Davol Inc., Warwick, RI (US)

(72) Inventors: Keith Greenawalt, Milton, MA (US); Christopher Bowley, Newport, RI (US); Jessica Powell, Laurel, MD (US); Rajendra R. Bhat, Cary, NC (US); Michael T. Cash, Timberlake, NC (US); Aaron D. Strickland, Freeville, NY (US); Esther M. Valliant, Freeville, NY (US); Frederick H. Strickler, Jr., Boston, MA (US); Andrew C. Yang, Taylorsville, NC (US)

(73) Assignee: Davol Inc., Warwick, RI (US)

( * ) Notice: Subject to any disclaimer, the term of this patent is extended or adjusted under 35 U.S.C. 154(b) by 0 days.

(21) Appl. No.: 17/365,749

(22) Filed: Jul. 1, 2021

(65) Prior Publication Data
US 2022/0002444 A1 Jan. 6, 2022

Related U.S. Application Data

(60) Provisional application No. 63/047,892, filed on Jul. 2, 2020.

(51) Int. Cl.
*C08B 31/00* (2006.01)
*C08B 31/12* (2006.01)
*C08B 31/04* (2006.01)
*A61L 24/08* (2006.01)

(52) U.S. Cl.
CPC .............. *C08B 31/00* (2013.01); *A61L 24/08* (2013.01); *C08B 31/04* (2013.01); *C08B 31/125* (2013.01)

(58) Field of Classification Search
CPC ....... C08B 31/00; C08B 31/04; C08B 31/125; A61L 24/08
See application file for complete search history.

(56) References Cited

U.S. PATENT DOCUMENTS

| | | |
|---|---|---|
| 4,002,173 A | 1/1977 | Manning et al. |
| 4,101,380 A | 7/1978 | Rubinstein et al. |
| 4,537,767 A | 8/1985 | Rothman et al. |
| 4,664,105 A | 5/1987 | Dautzenberg et al. |
| 4,775,622 A | 10/1988 | Hitzeman et al. |
| 4,839,345 A | 6/1989 | Doi et al. |
| 4,909,251 A | 3/1990 | Seelich |
| 4,913,897 A | 4/1990 | Chvapil et al. |
| 4,914,027 A | 4/1990 | Knapp et al. |
| 4,937,193 A | 6/1990 | Hinchliffe et al. |
| 4,990,447 A | 2/1991 | Konig et al. |
| 5,037,744 A | 8/1991 | Knapp et al. |
| 5,100,784 A | 3/1992 | Latta et al. |
| 5,118,794 A | 6/1992 | Grangeorge et al. |
| 5,132,404 A | 7/1992 | Ohtani et al. |
| 5,187,261 A | 2/1993 | Latta et al. |
| 5,209,776 A | 5/1993 | Bass |
| 5,250,662 A | 10/1993 | Chang |
| 5,260,202 A | 11/1993 | Clarke et al. |
| 5,277,818 A | 1/1994 | Matsuoka et al. |
| 5,292,362 A | 3/1994 | Bass et al. |
| 5,302,697 A | 4/1994 | Goodey et al. |
| 5,324,775 A | 6/1994 | Rhee et al. |
| 5,369,020 A | 11/1994 | Sumi et al. |
| 5,380,712 A | 1/1995 | Ballance et al. |
| 5,409,815 A | 4/1995 | Nakagawa et al. |
| 5,410,016 A | 4/1995 | Hubbell et al. |
| 5,440,018 A | 8/1995 | Ohmura et al. |
| 5,476,909 A | 12/1995 | Kim et al. |
| 5,502,042 A | 3/1996 | Gruskin et al. |
| 5,503,993 A | 4/1996 | Hayasuke et al. |
| 5,514,379 A | 5/1996 | Weissleder et al. |
| 5,514,380 A | 5/1996 | Song et al. |
| 5,521,287 A | 5/1996 | Ohmura et al. |
| 5,571,801 A | 11/1996 | Segall et al. |
| 5,583,114 A | 12/1996 | Barrows et al. |
| 5,593,858 A | 1/1997 | Fleer et al. |
| 5,605,255 A | 2/1997 | Reidel et al. |
| 5,612,196 A | 3/1997 | Becquart et al. |
| 5,612,197 A | 3/1997 | Ohda et al. |
| 5,616,691 A | 4/1997 | Takahashi et al. |
| 5,627,046 A | 5/1997 | Falcone et al. |
| 5,627,052 A | 5/1997 | Schrader |
| 5,631,145 A | 5/1997 | Kobayashi et al. |
| 5,633,146 A | 5/1997 | Fleer et al. |
| 5,643,792 A | 7/1997 | Okabayashi et al. |
| 5,648,243 A | 7/1997 | Hurwitz et al. |
| 5,656,729 A | 8/1997 | Fuluhata et al. |

(Continued)

FOREIGN PATENT DOCUMENTS

AU   2007296056 A1   3/2008
CA      2451624 A1  12/2002

(Continued)

OTHER PUBLICATIONS

Li et al., Polymer Degradation and Stability, 2017, 137, p. 75-82. (Year: 2017).*
Delval et al., Carbohydrate Polymers, 2005, 60, p. 67-75. (Year: 2005).*
Das et al., RSC Adv., 2015, 5, p. 25014-25050. (Year: 2015).*
Lim et al., Polym. Adv. Technol., 2018, 29, p. 2766-2773. (Year: 2018).*
International Search Report and Written Opinion dated Jul. 8, 2021 for International Application No. PCT/US2021/023359.
International Search Report and Written Opinion dated Oct. 29, 2020 for International Application No. PCT/US2020/039660.

(Continued)

*Primary Examiner* — Jonathan S Lau
(74) *Attorney, Agent, or Firm* — Wolf, Greenfield & Sacks, P.C.

(57) ABSTRACT

Compositions and methods related to powdered hemostats that crosslink during and/or after application to a bleeding site are generally described.

32 Claims, 4 Drawing Sheets

(56) References Cited

U.S. PATENT DOCUMENTS

| | | |
|---|---|---|
| 5,667,986 A | 9/1997 | Goodey et al. |
| 5,677,424 A | 10/1997 | Rucheton et al. |
| 5,679,543 A | 10/1997 | Lawlis |
| 5,691,451 A | 11/1997 | Ohya et al. |
| 5,728,553 A | 3/1998 | Goodey et al. |
| 5,733,563 A | 3/1998 | Fortier |
| 5,752,974 A | 5/1998 | Rhee |
| 5,756,313 A | 5/1998 | Okabayashi et al. |
| 5,759,819 A | 6/1998 | Kobayashi et al. |
| 5,770,229 A | 6/1998 | Tanihara et al. |
| 5,783,423 A | 7/1998 | Wood et al. |
| 5,791,352 A | 8/1998 | Reich et al. |
| 5,846,930 A | 12/1998 | Ristol Debart et al. |
| 5,849,874 A | 12/1998 | van der Laken et al. |
| 5,874,500 A | 2/1999 | Rhee et al. |
| RE36,259 E | 7/1999 | Tenold |
| 5,919,907 A | 7/1999 | Shanbrom |
| 5,962,649 A | 10/1999 | Noda et al. |
| 5,965,386 A | 10/1999 | Kerry-Williams et al. |
| 5,986,062 A | 11/1999 | Ohmura et al. |
| 5,994,507 A | 11/1999 | Pilotti et al. |
| 6,001,974 A | 12/1999 | Demmer et al. |
| 6,022,954 A | 2/2000 | Dernis et al. |
| 6,034,221 A | 3/2000 | Berezenko et al. |
| 6,043,213 A | 3/2000 | Tsubota |
| 6,051,248 A | 4/2000 | Sawhney et al. |
| 6,060,461 A | 5/2000 | Drake |
| 6,063,061 A | 5/2000 | Wallace |
| 6,113,629 A | 9/2000 | Ken |
| 6,150,504 A | 11/2000 | Van Der Laken et al. |
| 6,165,201 A | 12/2000 | Sawhney et al. |
| 6,166,130 A | 12/2000 | Rhee et al. |
| 6,177,095 B1 | 1/2001 | Sawhney et al. |
| 6,179,862 B1 | 1/2001 | Sawhney |
| 6,183,498 B1 | 2/2001 | Devore et al. |
| 6,217,894 B1 | 4/2001 | Sawhney et al. |
| 6,312,725 B1 | 11/2001 | Wallace et al. |
| 6,328,229 B1 | 12/2001 | Duronio et al. |
| 6,362,254 B2 | 3/2002 | Harris et al. |
| 6,371,975 B2 | 4/2002 | Cruise |
| 6,437,025 B1 | 8/2002 | Harris et al. |
| 6,458,147 B1 | 10/2002 | Cruise et al. |
| 6,458,889 B1 | 10/2002 | Trollsas et al. |
| 6,475,508 B1 | 11/2002 | Schwartz et al. |
| 6,495,127 B1 | 12/2002 | Wallace et al. |
| 6,504,011 B1 | 1/2003 | Van Der Laken et al. |
| 6,514,534 B1 | 2/2003 | Sawhney |
| 6,521,431 B1 | 2/2003 | Kiser et al. |
| 6,534,591 B2 | 3/2003 | Rhee et al. |
| 6,541,543 B2 | 4/2003 | Harris et al. |
| RE38,158 E | 6/2003 | Barrows et al. |
| 6,576,263 B2 | 6/2003 | Truong et al. |
| 6,613,884 B1 | 9/2003 | Johansson |
| 6,617,133 B1 | 9/2003 | Noda et al. |
| 6,624,245 B2 | 9/2003 | Wallace et al. |
| 6,629,947 B1 | 10/2003 | Sahatjian et al. |
| 6,638,740 B1 | 10/2003 | Goodey et al. |
| 6,648,852 B2 | 11/2003 | Wirt et al. |
| 6,685,727 B2 | 2/2004 | Fisher et al. |
| 6,703,047 B2 | 3/2004 | Sawhney et al. |
| 6,706,690 B2 | 3/2004 | Reich |
| 6,708,847 B2 | 3/2004 | Ljungquist |
| 6,733,472 B1 | 5/2004 | Epstein et al. |
| 6,818,018 B1 | 11/2004 | Sawhney |
| 6,830,756 B2 | 12/2004 | Hnojewyj |
| 6,831,157 B2 | 12/2004 | Van Der Laken et al. |
| 6,833,408 B2 | 12/2004 | Sehl et al. |
| 6,874,657 B2 | 4/2005 | Metzner et al. |
| 6,887,974 B2 | 5/2005 | Pathak |
| 6,899,889 B1 | 5/2005 | Hnojewyj et al. |
| 6,908,749 B2 | 6/2005 | Nouchi et al. |
| RE38,827 E | 10/2005 | Barrows et al. |
| 6,969,400 B2 | 11/2005 | Rhee et al. |
| 6,989,192 B2 | 1/2006 | Husemann et al. |
| 6,994,686 B2 | 2/2006 | Cruise et al. |
| 7,001,885 B2 | 2/2006 | Adachi et al. |
| 7,008,635 B1 | 3/2006 | Coury et al. |
| 7,009,034 B2 | 3/2006 | Pathak et al. |
| 7,025,990 B2 | 4/2006 | Sawhney |
| 7,030,278 B2 | 4/2006 | Harris et al. |
| 7,057,019 B2 | 6/2006 | Pathak |
| 7,074,425 B2 | 7/2006 | Constantine et al. |
| 7,077,339 B2 | 7/2006 | Leach |
| 7,119,124 B2 | 10/2006 | Hegedus et al. |
| 7,151,135 B2 | 12/2006 | Rhee et al. |
| 7,166,577 B2 | 1/2007 | Otagiri et al. |
| 7,176,256 B2 | 2/2007 | Rhee et al. |
| 7,223,561 B2 | 5/2007 | Goodey et al. |
| 7,223,803 B2 | 5/2007 | Harris et al. |
| 7,238,364 B2 | 7/2007 | Sawhney et al. |
| 7,247,314 B2 | 7/2007 | Hnojewyj et al. |
| 7,279,001 B2 | 10/2007 | Addis et al. |
| 7,304,208 B2 | 12/2007 | Huang et al. |
| 7,307,148 B2 | 12/2007 | Bousquet-Gagnon et al. |
| 7,318,933 B2 | 1/2008 | Hnojewyj |
| 7,320,962 B2 | 1/2008 | Reich |
| 7,332,566 B2 | 2/2008 | Pathak et al. |
| 7,335,220 B2 | 2/2008 | Khosravi et al. |
| 7,347,850 B2 | 3/2008 | Sawhney et al. |
| 7,351,249 B2 | 4/2008 | Hnojewyj et al. |
| 7,423,124 B2 | 9/2008 | Belew et al. |
| 7,459,542 B2 | 12/2008 | Sang et al. |
| 7,485,719 B2 | 2/2009 | Abe et al. |
| 7,490,738 B2 | 2/2009 | Crews |
| 7,501,455 B2 | 3/2009 | Hegedus et al. |
| 7,516,872 B2 | 4/2009 | Boone et al. |
| 7,528,202 B2 | 5/2009 | Harris et al. |
| 7,592,418 B2 | 9/2009 | Pathak et al. |
| 7,597,882 B2 | 10/2009 | Pathak et al. |
| 7,601,515 B2 | 10/2009 | Goodey et al. |
| 7,641,075 B2 | 1/2010 | Crews |
| 7,648,713 B2 | 1/2010 | Sawhney |
| 7,714,088 B2 | 5/2010 | Harris et al. |
| 7,718,851 B2 | 5/2010 | Huang et al. |
| 7,727,547 B2 | 6/2010 | Fortune et al. |
| 7,799,767 B2 | 9/2010 | Lamberti et al. |
| 7,883,693 B2 | 2/2011 | Sehl et al. |
| 7,914,819 B1 | 3/2011 | Wen et al. |
| 7,943,570 B2 | 5/2011 | Nakajou et al. |
| 7,963,937 B2 | 6/2011 | Pauser et al. |
| 7,972,357 B2 | 7/2011 | Bettuchi |
| 7,993,877 B2 | 8/2011 | Van Urk et al. |
| 8,003,742 B2 | 8/2011 | Harris et al. |
| 8,034,367 B2 | 10/2011 | Hnojewyj |
| 8,067,031 B2 | 11/2011 | Daniloff et al. |
| 8,084,580 B2 | 12/2011 | Jorquera Nieto et al. |
| 8,088,416 B2 | 1/2012 | Jorquera Nieto et al. |
| 8,092,837 B2 | 1/2012 | Enyart et al. |
| 8,100,294 B2 | 1/2012 | May et al. |
| 8,105,622 B2 | 1/2012 | Sawhney |
| 8,119,604 B2 | 2/2012 | Gombotz et al. |
| RE43,331 E | 5/2012 | Samaritani et al. |
| 8,231,599 B2 | 7/2012 | Jorquera Nieto et al. |
| 8,236,527 B2 | 8/2012 | Chen et al. |
| 8,236,927 B2 | 8/2012 | Stange |
| 8,241,656 B2 | 8/2012 | Chudzik et al. |
| 8,252,551 B2 | 8/2012 | Sleep et al. |
| 8,257,690 B2 | 9/2012 | Chenault |
| 8,258,102 B2 | 9/2012 | Sleep |
| 8,258,264 B2 | 9/2012 | Tagawa et al. |
| 8,288,477 B2 | 10/2012 | Hadba et al. |
| 8,309,680 B2 | 11/2012 | McManus et al. |
| 8,314,195 B2 | 11/2012 | Elisseeff |
| 8,323,262 B2 | 12/2012 | D'Alessio et al. |
| 8,409,249 B2 | 4/2013 | Hnojewyj et al. |
| 8,410,189 B2 | 4/2013 | Carnahan et al. |
| 8,460,695 B2 | 6/2013 | Greenawalt |
| 8,460,708 B2 | 6/2013 | Daniloff et al. |
| 8,481,073 B2 | 7/2013 | Daniloff et al. |
| 8,512,749 B2 | 8/2013 | Sawhney et al. |
| 8,535,705 B2 | 9/2013 | Pathak et al. |
| 8,545,864 B2 | 10/2013 | Morris et al. |
| 8,545,871 B2 | 10/2013 | Arthur et al. |
| 8,563,037 B2 | 10/2013 | Rappleye et al. |

(56) References Cited

U.S. PATENT DOCUMENTS

| | | |
|---|---|---|
| 8,623,842 B2 | 1/2014 | Roberts et al. |
| 8,673,335 B2 | 3/2014 | Jones et al. |
| 8,703,170 B2 | 4/2014 | Hedrich et al. |
| 8,703,176 B2 | 4/2014 | Zhu et al. |
| 8,741,832 B2 | 6/2014 | Acharya et al. |
| 8,802,652 B2 | 8/2014 | Myntti et al. |
| 8,846,022 B2 | 9/2014 | Carnahan et al. |
| 8,912,168 B2 | 12/2014 | Ji et al. |
| 8,968,716 B2 | 3/2015 | Park et al. |
| 8,968,783 B2 | 3/2015 | Bennett et al. |
| 8,980,295 B2 | 3/2015 | Kao et al. |
| 9,023,379 B2 | 5/2015 | Pathak et al. |
| 9,040,093 B2 | 5/2015 | Wagner |
| 9,061,087 B2 | 6/2015 | Roberts et al. |
| 9,114,172 B2 | 8/2015 | Rhee et al. |
| 9,345,662 B2 | 5/2016 | Sinko et al. |
| 9,345,809 B2 | 5/2016 | Falcone et al. |
| 9,375,505 B2 | 6/2016 | Hedrich et al. |
| 9,393,344 B2 | 7/2016 | Stockman et al. |
| 9,492,376 B2 | 11/2016 | Seliktar et al. |
| 9,616,088 B2 | 4/2017 | Diehn et al. |
| 9,662,400 B2 | 5/2017 | Smith et al. |
| 9,700,650 B2 | 7/2017 | Gong et al. |
| 9,707,252 B2 | 7/2017 | Hadba et al. |
| 9,708,416 B2 | 7/2017 | Malmsjo et al. |
| 9,844,597 B2 | 12/2017 | Chau et al. |
| 9,878,066 B2 | 1/2018 | Stockman et al. |
| 9,895,465 B2 | 2/2018 | Lamberti et al. |
| 9,993,577 B2 | 6/2018 | Grinstaff et al. |
| 10,172,938 B2 | 1/2019 | Kiick et al. |
| 10,314,937 B2 | 6/2019 | Ji et al. |
| 10,517,988 B1 | 12/2019 | Modak et al. |
| 10,584,184 B2 | 3/2020 | Tramontano et al. |
| 10,595,978 B2 | 3/2020 | Lavigne et al. |
| 10,905,792 B2 | 2/2021 | Laub et al. |
| 11,154,665 B2 | 10/2021 | Goodman et al. |
| 11,208,530 B2 | 12/2021 | Zhao et al. |
| 2002/0022588 A1 | 2/2002 | Wilkie et al. |
| 2002/0106409 A1 | 8/2002 | Sawhney et al. |
| 2003/0023209 A1 | 1/2003 | Gruskin et al. |
| 2003/0187387 A1 | 10/2003 | Wirt et al. |
| 2003/0223957 A1 | 12/2003 | Schwartz et al. |
| 2005/0118238 A1 | 6/2005 | Zhu et al. |
| 2005/0123588 A1 | 6/2005 | Zhu et al. |
| 2005/0271727 A1 | 12/2005 | Yao |
| 2006/0078536 A1 | 4/2006 | Kodokian et al. |
| 2006/0088570 A1 | 4/2006 | Cruise et al. |
| 2006/0093648 A1 | 5/2006 | Coury et al. |
| 2006/0273109 A1 | 12/2006 | Keller |
| 2007/0065481 A1 | 3/2007 | Chudzik et al. |
| 2007/0086958 A1 | 4/2007 | Drake et al. |
| 2007/0213768 A1 | 9/2007 | Wasserman et al. |
| 2007/0248653 A1 | 10/2007 | Cochrum et al. |
| 2008/0038313 A1 | 2/2008 | Addis et al. |
| 2008/0215088 A1 | 9/2008 | Hnojewyj et al. |
| 2008/0293910 A1 | 11/2008 | Kapiamba et al. |
| 2009/0062233 A1 | 3/2009 | Ji et al. |
| 2009/0152267 A1 | 6/2009 | May et al. |
| 2009/0285780 A1 | 11/2009 | Lee |
| 2009/0291911 A1 | 11/2009 | Myntti et al. |
| 2010/0087851 A1 | 4/2010 | Jones et al. |
| 2010/0100099 A1 | 4/2010 | Reilly et al. |
| 2010/0168007 A1 | 7/2010 | Cruise et al. |
| 2010/0204718 A1 | 8/2010 | Rappleye et al. |
| 2010/0217231 A1 | 8/2010 | Ilan et al. |
| 2010/0274279 A1 | 10/2010 | Delmotte |
| 2010/0297235 A1 | 11/2010 | Hnojewyj |
| 2011/0027216 A1 | 2/2011 | Chenault |
| 2011/0104280 A1 | 5/2011 | Hnojewyj |
| 2011/0123476 A1 | 5/2011 | Kapiamba et al. |
| 2011/0125089 A1 | 5/2011 | Senderoff et al. |
| 2011/0150821 A1 | 6/2011 | Daniloff et al. |
| 2011/0166596 A1 | 7/2011 | Delmotte |
| 2011/0272436 A1 | 11/2011 | Vogt et al. |
| 2011/0274725 A1 | 11/2011 | Breton et al. |
| 2011/0282464 A1 | 11/2011 | Sargeant et al. |
| 2012/0035129 A1 | 2/2012 | Wagman |
| 2012/0041481 A1 | 2/2012 | Daniloff et al. |
| 2012/0101519 A1 | 4/2012 | Hill et al. |
| 2012/0156259 A1 | 6/2012 | Rau et al. |
| 2012/0244198 A1 | 9/2012 | Malmsjo et al. |
| 2012/0315305 A1 | 12/2012 | Koopman et al. |
| 2013/0090291 A1 | 4/2013 | Guile et al. |
| 2013/0096082 A1 | 4/2013 | Harkamp et al. |
| 2013/0209659 A1 | 8/2013 | Racenet et al. |
| 2013/0261192 A1 | 10/2013 | Yang et al. |
| 2014/0105950 A1 | 4/2014 | Hardy et al. |
| 2014/0171883 A1 | 6/2014 | Roberts et al. |
| 2015/0306277 A1 | 10/2015 | Pathak et al. |
| 2017/0056550 A1 | 3/2017 | Hoemann et al. |
| 2017/0106119 A1 | 4/2017 | Skinner et al. |
| 2017/0252479 A1 | 9/2017 | Ji et al. |
| 2018/0036338 A1 | 2/2018 | Sanders et al. |
| 2018/0344898 A1 | 12/2018 | Kronenthal et al. |
| 2019/0001018 A1 | 1/2019 | Stockman et al. |
| 2019/0388516 A1 | 12/2019 | Floyd et al. |
| 2019/0388577 A1 | 12/2019 | Chandrashekhar-Bhat et al. |
| 2019/0388580 A1 | 12/2019 | Guo et al. |
| 2019/0388665 A1 | 12/2019 | Christakis et al. |
| 2020/0030481 A1 | 1/2020 | Hedrich et al. |
| 2020/0046877 A1 | 2/2020 | Kageyama et al. |
| 2020/0102446 A1 | 4/2020 | Dowling |
| 2020/0121825 A1 | 4/2020 | Dowling |
| 2020/0139021 A1 | 5/2020 | Ilan et al. |
| 2021/0060204 A1 | 3/2021 | Ji et al. |
| 2022/0001075 A1 | 1/2022 | Greenawalt et al. |
| 2022/0211900 A1 | 7/2022 | Greenawalt et al. |
| 2022/0323637 A1 | 10/2022 | Greenawalt et al. |

FOREIGN PATENT DOCUMENTS

| | | |
|---|---|---|
| CA | 2581093 A1 | 3/2006 |
| CN | 100556467 C | 11/2009 |
| CN | 101791436 A | 8/2010 |
| CN | 101497670 B | 4/2012 |
| CN | 105838299 A | 8/2016 |
| CN | 110464869 A | 11/2019 |
| CN | 111068101 A | 4/2020 |
| CN | 111317857 A | 6/2020 |
| CN | 111317858 A | 6/2020 |
| CN | 111714683 A | 9/2020 |
| CN | 111714684 A | 9/2020 |
| CN | 111714686 A | 9/2020 |
| CN | 111714688 A | 9/2020 |
| CN | 111729125 A | 10/2020 |
| CN | 112138205 A | 12/2020 |
| CN | 112494712 A | 3/2021 |
| CN | 108744019 B | 5/2021 |
| CN | 113061255 A | 7/2021 |
| CN | 110269954 B | 8/2021 |
| DE | 3502998 A1 | 7/1986 |
| EP | 0258067 B1 | 3/1993 |
| EP | 0420007 B1 | 1/1994 |
| EP | 0402205 B1 | 12/1995 |
| EP | 0701822 A2 | 3/1996 |
| EP | 0705298 A1 | 4/1996 |
| EP | 0422769 B1 | 4/1997 |
| EP | 0504823 B1 | 6/1997 |
| EP | 0367220 B1 | 1/1998 |
| EP | 0428758 B1 | 1/1998 |
| EP | 0584166 B1 | 3/1998 |
| EP | 0597035 B1 | 9/1998 |
| EP | 0876165 A1 | 11/1998 |
| EP | 0498133 B1 | 5/1999 |
| EP | 0625202 B1 | 7/1999 |
| EP | 0524681 B1 | 11/1999 |
| EP | 0559895 B1 | 1/2001 |
| EP | 0764209 B1 | 1/2001 |
| EP | 0828759 B1 | 1/2001 |
| EP | 0570916 B1 | 1/2002 |
| EP | 1185288 A1 | 3/2002 |
| EP | 0655503 B1 | 7/2002 |
| EP | 1218437 A1 | 7/2002 |
| EP | 0736605 B1 | 4/2003 |

(56) References Cited

FOREIGN PATENT DOCUMENTS

| | | |
|---|---|---|
| EP | 0341103 B2 | 8/2003 |
| EP | 0637317 B1 | 8/2003 |
| EP | 0699687 B1 | 1/2004 |
| EP | 0749478 B1 | 2/2004 |
| EP | 1031578 B1 | 4/2004 |
| EP | 1610829 A1 | 1/2006 |
| EP | 1504031 B1 | 8/2006 |
| EP | 1329462 B1 | 12/2006 |
| EP | 1718673 B1 | 9/2007 |
| EP | 1149163 B1 | 12/2008 |
| EP | 1710250 B1 | 4/2009 |
| EP | 2093245 A2 | 8/2009 |
| EP | 1479393 B1 | 8/2010 |
| JP | 5232347 B2 | 7/2013 |
| KR | 101507589 B1 | 4/2015 |
| KR | 102220832 B1 | 2/2021 |
| WO | WO 90/13540 A1 | 11/1990 |
| WO | WO 93/15204 A1 | 8/1993 |
| WO | WO 94/03155 A1 | 2/1994 |
| WO | WO 97/22371 A1 | 6/1997 |
| WO | WO 97/29715 A1 | 8/1997 |
| WO | WO 98/29099 A2 | 7/1998 |
| WO | WO 2006/113845 A1 | 10/2006 |
| WO | WO 2007/084609 A2 | 7/2007 |
| WO | WO 2012/123728 A2 | 9/2012 |
| WO | WO 2019/137414 A1 | 7/2019 |
| WO | WO 2020/004813 A1 | 1/2020 |
| WO | WO 2020/019880 A1 | 1/2020 |
| WO | WO 2020/044237 A1 | 3/2020 |
| WO | WO 2020/068814 A1 | 4/2020 |
| WO | WO 2020/197969 A1 | 10/2020 |
| WO | WO 2020/264188 A1 | 12/2020 |
| WO | WO 2021/027219 A1 | 2/2021 |
| WO | WO 2021/128050 A1 | 7/2021 |
| WO | WO 2021/188904 A1 | 9/2021 |
| WO | WO 2021/189024 A1 | 9/2021 |

OTHER PUBLICATIONS

International Preliminary Report on Patentability dated Jan. 6, 2022 for International Application No. PCT/US2020/039660.

International Search Report and Written Opinion dated Apr. 4, 2022 for International Application No. PCT/US2021/065204.

[No. Author Listed], Tridynetm Vascular Sealant. C.R. Bard, Inc. 2015. 21 pages.

Abuchowski et al., Cancer therapy with chemically modified enzymes. I. Antitumor properties of polyethylene glycol-asparaginase conjugates. Cancer Biochem Biophys. Jun. 1984;7(2):175-86.

Calabretta et al., Antibacterial activities of poly (amidoamine) dendrimers terminated with amino and poly(ethylene glycol) groups. Biomacromolecules. Jun. 2007;8(6):1807-11. doi: 10.1021/bm0701088. Epub May 19, 2007.

Carlstedt et al., Hydration and the phase diagram of acid hydrolyzed potato starch. Carbohydr Polym. Nov. 4, 2014;112:569-77. doi: 10.1016/j.carbpol.2014.06.037. Epub Jun. 21, 2014. Supplementary Material, 6 pages.

Conti et al., A proposed new method for the crosslinking of chitosan microspheres. Drug Deliv. 1998;5(2):87-93. doi: 10.3109/10717549809031383.

Diaz et al., Partially PEGylated PAMAM dendrimers as solubility enhancers of Silybin. Pharm Dev Technol. Sep. 2018;23(7):689-696. doi: 10.1080/10837450.2017.1315134. Epub Apr. 19, 2017.

Elchinger et al., Polysaccharides: The "Click" Chemistry Impact. Polymers. Sep. 27, 2011;3(4):1607-51. doi: 10.3390/polym3041607.

El-Sayed et al., New approach for immobilization of 3-aminopropyltrimethoxysilane and TiO2 nanoparticles into cellulose for BJ1 skin cells proliferation. Carbohydr Polym. Nov. 1, 2018;199:193-204. doi: 10.1016/j.carbpol.2018.07.004. Epub Jul. 9, 2018.

Ereth et al., Microporous polysaccharide hemospheres do not inhibit bone healing compared to bone wax or microfibrillar collagen. Orthopedics. Mar. 2008;31(3):222. doi: 10.3928/01477447-20080301-10.

Fogh-Andersen et al., Ionic binding, net charge, and Donnan effect of human serum albumin as a function of pH. Clin Chem. Jan. 1993;39(1):48-52.

Fuller, C., Reduction of intraoperative air leaks with Progel in pulmonary resection: a comprehensive review. J Cardiothorac Surg. Apr. 16, 2013;8:90. doi: 10.1186/1749-8090-8-90.

Hamdi et al., Enzymatic degradation of epichlorohydrin crosslinked starch microspheres by alpha-amylase. Pharm Res. Jun. 1999;16(6):867-75. doi: 10.1023/a:1018878120100.

Hamdi et al., Formulation of epichlorohydrin cross-linked starch microspheres. J Microencapsul. May-Jun. 2001;18(3):373-83. doi: 10.1080/02652040010019505.

Haroon et al., Chemical modification of starch and its application as an adsorbent material. R. Soc. Chem., Aug. 12, 2016;6:78264-85. doi: https://doi.org/10.1039/C6RA16795K.

Hasegawa et al., 'Click chemistry' on polysaccharides: a convenient, general, and monitorable approach to develop (1—>3)-beta-D-glucans with various functional appendages. Carbohydr Res. Jan. 16, 2006;341(1):35-40. doi: 10.1016/j.carres.2005.10.009. Epub Nov. 14, 2005.

Holmes et al., Antimicrobial efficacy and mechanism of action of poly(amidoamine) (PAMAM) dendrimers against opportunistic pathogens. Int J Antimicrob Agents. Apr. 2019;53(4):500-507. doi: 10.1016/j.ijantimicag.2018.12.012. Epub Dec. 30, 2018.

Jevprasesphant et al., The influence of surface modification on the cytotoxicity of PAMAM dendrimers. Int J Pharm. Feb. 18, 2003;252(1-2):263-6. doi: 10.1016/s0378-5173(02)00623-3.

Kobayashi et al., In vivo evaluation of a new sealant material on a rat lung air leak model. J Biomed Mater Res. 2001;58(6):658-65. doi: 10.1002/jbm.1066.

Koga et al., Chemically-modified cellulose paper as a microstructured catalytic reactor. Molecules. Jan. 15, 2015;20(1):1495-508. doi: 10.3390/molecules20011495.

Koga et al., In situ modification of cellulose paper with amino groups for catalytic applications. J. Mater. Chem. May 27, 2011;21:9356-61. doi: https://doi.org/10.1039/C1JM10543D.

Kuniak et al., Study of the Crosslinking Reaction between Epichlorohydrin and Starch. Starch. 1972;24(4):110-116. doi: 10.1002/star.19720240404.

Lopez et al., Antibacterial activity and cytotoxicity of PEGylated poly(amidoamine) dendrimers. Mol Biosyst. Oct. 2009;5(10):1148-56. doi: 10.1039/b904746h. Epub Jul. 3, 2009. Author Manuscript, 17 pages.

Qi et al., PEG-conjugated PAMAM dendrimers mediate efficient intramuscular gene expression. AAPS J. Sep. 2009;11(3):395-405. doi: 10.1208/s12248-009-9116-1. Epub May 29, 2009.

Rostami et al., Peptide-conjugated PEGylated PAMAM as a highly affinitive nanocarrier towards HER2-overexpressing cancer cells. RSC Adv. Oct. 21, 2016;6:107337-107343. doi: 10.1039/C6RA19552K.

Sadeghi et al., Evaluation of different parameters effect on maltodextrin production by alpha-amylase Termamyl 2-x, 2008, World Applied Sciences Journal, 3(1):34-39.

Schmitz et al., Use of a plant-based polysaccharide hemostat for the treatment of sternal bleeding after median sternotomy. J Cardiothorac Surg. Apr. 24, 2015;10:59. doi: 10.1186/s13019-015-0263-4.

Shao et al., Comparison of generation 3 polyamidoamine dendrimer and generation 4 polypropylenimine dendrimer on drug loading, complex structure, release behavior, and cytotoxicity. Int J Nanomedicine. 2011;6:3361-72. doi: 10.2147/IJN.S27028. Epub Dec. 16, 2011.

Suwanprateeb et al., Preparation and characterization of PEG-PPG-PEG copolymer/pregelatinized starch blends for use as resorbable bone hemostatic wax. J Mater Sci Mater Med. Dec. 2013;24(12):2881-8. doi: 10.1007/s10856-013-5027-x. Epub Aug. 17, 2013.

Tankam et al., Alkynyl polysaccharides: synthesis of propargyl potato starch followed by subsequent derivatizations. Carbohydr Res. Oct. 15, 2007;342(14):2049-60. doi: 10.1016/j.carres.2007.05.017. Epub May 18, 2007.

Wang et al., Preparation of amino-functionalized regenerated cellulose membranes with high catalytic activity. Int J Biol Macromol. Sep. 2017;102:944-951. doi: 10.1016/j.ijbiomac.2017.04.096. Epub Apr. 27, 2017.

(56) References Cited

OTHER PUBLICATIONS

Xue et al., Amino-terminated generation 2 poly(amidoamine) dendrimer as a potential broad-spectrum, nonresistance-inducing antibacterial agent. AAPS J. Jan. 2013;15(1):132-42. doi: 10.1208/S12248-012-9416-8. Epub Nov. 8, 2012.
U.S. Appl. No. 17/942,536, filed Sep. 12, 2022, Addison et al.
PCT/US2021/023359, Sep. 29, 2022, International Preliminary Report on Patentability.
International Preliminary Report on Patentability dated Sep. 29, 2022 for International Application No. PCT/US2021/023359.
Anraku et al., Stabilizing mechanisms in commercial albumin preparations: octanoate and N-acetyl-L-tryptophanate protect human serum albumin against heat and oxidative stress. Biochim Biophys Acta. Oct. 1, 2004;1702(1):9-17. doi: 10.1016/j.bbapap.2004.07.002.
Cai et al., The Proof Is in the Pidan: Generalizing Proteins as Patchy Particles. ACS Cent Sci. 2018 Jul. 25;4(7):840-853. doi: 10.1021/acscentsci.8b00187. Epub Jun. 28, 2018.
Cleland et al., Polyethylene glycol enhanced protein refolding. Biotechnology (N Y). Sep. 1992;10(9):1013-9. doi: 10.1038/nbt0992-1013.

\* cited by examiner

US 11,739,166 B2

REACTIVE POLYSACCHARIDE-BASED HEMOSTATIC AGENT

RELATED APPLICATIONS

This application claims priority under 35 U.S.C. § 119(e) to U.S. Provisional Patent Application No. 63/047,892, filed Jul. 2, 2020, and entitled "Reactive Polysaccharide-Based Hemostatic Agent," which is incorporated herein by reference in its entirety for all purposes.

TECHNICAL FIELD

Compositions and methods related to powdered hemostats that crosslink during and/or after application to a bleeding site are generally described.

BACKGROUND

Existing powdered hemostats such as degradable starch microspheres (DSMs) or oxidized regenerative cellulose (ORC) and flowable hemostats such as liquid thrombin or fibrin glue can suffer from poor tissue adherence and may not be sufficiently effective when used for certain bleeding/wound sites. This may be due to a lack of absorbency, insufficient tissue adherence and/or cohesivity at the wound site to resist being washed away in the case of powdered hemostats. Furthermore, powder forms of hemostatic materials can, in certain cases, be difficult to apply to certain difficult to access bleeding sites, and therefore may suffer an inability to be able to be effectively applied to and/or stay at the source of bleeding. While flowable hemostatic forms are better suited for certain such applications, conventional powdered hemostats are often unable or poorly suited to be delivered in suspension, and existing flowable hemostats such as thrombin solutions and fibrin glues may be insufficiently effective or counterindicated for many applications. Additionally, typical conventional hemostats do not form a strong hydrogel network. This can create a need for manual compression to keep the products in place after application to a bleeding site, making it challenging for surgeons to continue to operate in the same area. Accordingly, improved hemostatic compositions and methods would be desirable.

SUMMARY

Compositions and methods related to powdered hemostats that crosslink during and/or after application to a bleeding site are generally described. The subject matter of the present invention involves, in some cases, interrelated products, alternative solutions to a particular problem, and/or a plurality of different uses of one or more systems and/or articles.

In one aspect, a dry, powdered hemostatic composition is provided. In some embodiments, the dry, powdered hemostatic composition comprises a first component comprising a modified polysaccharide component comprising a plurality of polysaccharide chains. In some embodiments, the plurality of polysaccharide chains are functionalized with electrophilic groups capable of reacting with amine groups. In some embodiments, the first modified polysaccharide component comprises one or more modified polysaccharides chosen from a) a plurality of dry, porous, microspheres formed of crosslinked starch functionalized with the electrophilic groups, and b) hydrolyzed, uncrosslinked starch functionalized with the electrophilic groups. In some embodiments, the dry, powdered hemostatic composition comprises a second component comprising a protein. In some embodiments, the first and second components are able to crosslink with each other to form a hemostatic hydrogel.

In some embodiments, the dry, powdered hemostatic composition comprises a first component comprising a modified polysaccharide component comprising a plurality of polysaccharide chains functionalized with electrophilic groups capable of reacting with amine groups, wherein the first modified polysaccharide component comprises one or more modified polysaccharides chosen from: a) a plurality of dry, porous, microspheres formed of crosslinked starch functionalized with the electrophilic groups, and b) hydrolyzed, uncrosslinked starch functionalized with the electrophilic groups. In some embodiments, the dry, powdered hemostatic composition comprises a second component comprising a multifunctionalized polyalkylene oxide-based polymer comprising amine groups or a corresponding salt thereof, wherein the first and second components are able to crosslink with each other to form a hemostatic hydrogel.

In some embodiments, the dry, powdered hemostatic composition comprises a first component comprising a multifunctionalized polyalkylene oxide-based polymer comprising electrophilic groups comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry, powdered hemostatic composition comprises a second component comprising a modified polysaccharide component comprising a plurality of polysaccharide chains functionalized with amine groups. In some embodiments, the first and second components are able to crosslink with each other into a hemostatic hydrogel.

In some embodiments, the dry, powdered hemostatic composition comprises a first component comprising hydrolyzed, uncrosslinked starch functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry, powdered hemostatic composition comprises a second component comprising hydrolyzed, uncrosslinked starch functionalized with amine groups. In some embodiments, the first and second components are able to crosslink into a hemostatic hydrogel upon exposure to water.

In some embodiments, the dry, powdered hemostatic composition comprises a first component comprising a first modified polysaccharide component comprising a plurality of polysaccharide chains functionalized with electrophilic groups capable of reacting with amine groups. In some embodiments, the dry, powdered hemostatic composition comprises a second component comprising a second modified polysaccharide component comprising a starch functionalized with amine groups. In some embodiments, the amine groups are at least two bonds removed from the backbone of the starch. In some embodiments, the first and second components are able to crosslink with each other to form a hemostatic hydrogel.

In some embodiments, the dry, powdered hemostatic composition comprises a first dry powder component comprising a plurality of first modified microporous microspheres comprising hydrolyzed starch crosslinked with glycerol ether or polyglycerol ether linkages, such as 1,3,-oxy-propan-2-ol linkages, functionalized with ligands comprising leaving groups selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry, powdered hemostatic composition comprises a second dry powder component comprising a plurality of second modified microporous microspheres comprising hydrolyzed starch crosslinked with glycerol ether or polyglycerol ether linkages, such as 1,3,-oxy-propan-2-ol linkages, functionalized with amine groups. In some embodiments, the first and second dry powder components are able to crosslink into a hemostatic hydrogel upon exposure to water.

In some embodiments, the dry, powdered hemostatic composition comprises a first dry powder component comprising hydrolyzed, uncrosslinked starch functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry, powdered, hemostatic composition comprises a second dry powder component comprising hydrolyzed, uncrosslinked starch functionalized with amine groups. In some embodiments, the first and second dry powder components are able to crosslink into a hemostatic hydrogel upon exposure to water.

In some embodiments, the dry, powdered hemostatic composition comprises a first component comprising a plurality of first modified microporous microspheres comprising hydrolyzed starch crosslinked with glycerol ether or polyglycerol ether linkages, such as 1,3,-oxy-propan-2-ol linkages, functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry, powdered hemostatic composition comprises a second component comprising a plurality of second modified microporous microspheres comprising hydrolyzed starch crosslinked with glycerol ether or polyglycerol ether linkages, such as 1,3,-oxy-propan-2-ol linkages, functionalized with amine groups. In some embodiments, the first and second components are able to crosslink into a hemostatic hydrogel upon exposure to water.

In some embodiments, the dry, powdered hemostatic composition comprises a first dry powder component comprising a plurality of modified microporous microspheres comprising hydrolyzed starch crosslinked with glycerol ether or polyglycerol ether linkages comprising at least 1,3,-oxy-propan-2-ol linkages, and functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry, powdered hemostatic composition comprises a second dry powder component comprising a protein. In some embodiments, the first and second dry powder components are able to crosslink into a hemostatic hydrogel upon exposure to water.

In some embodiments, the dry, powdered hemostatic composition comprises a first dry powder component comprising a multifunctionalized polymer comprising electrophilic groups comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry, powdered hemostatic composition comprises a second dry powder component comprising a plurality of modified microporous microspheres comprising hydrolyzed starch crosslinked with glycerol ether or polyglycerol ether linkages comprising at least 1,3,-oxy-propan-2-ol linkages, functionalized with amine groups. In some embodiments, the first and second dry powder components are able to crosslink into a hemostatic hydrogel upon exposure to water.

In some embodiments, the dry, powdered hemostatic composition comprises a first component comprising a multifunctionalized polyalkylene oxide-based polymer selected from the group consisting of

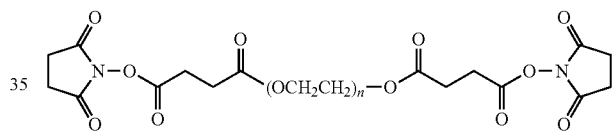

Poly(ethylene glycol) disuccinimidyl succinate, I

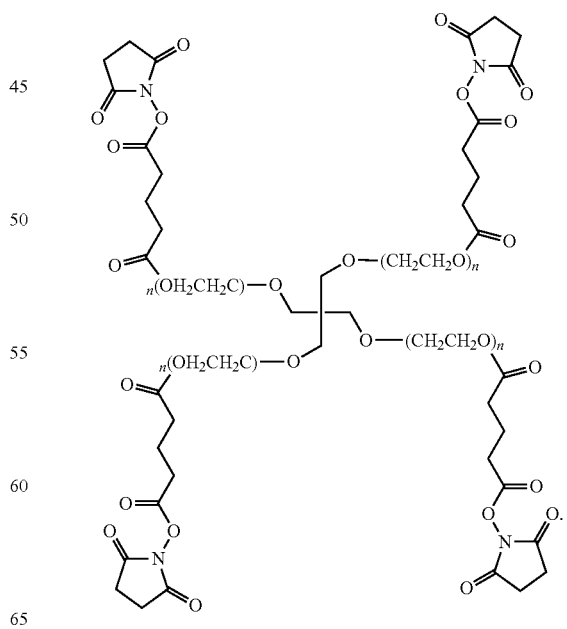

PEG Tetrasuccinimidyl Glutarate, and

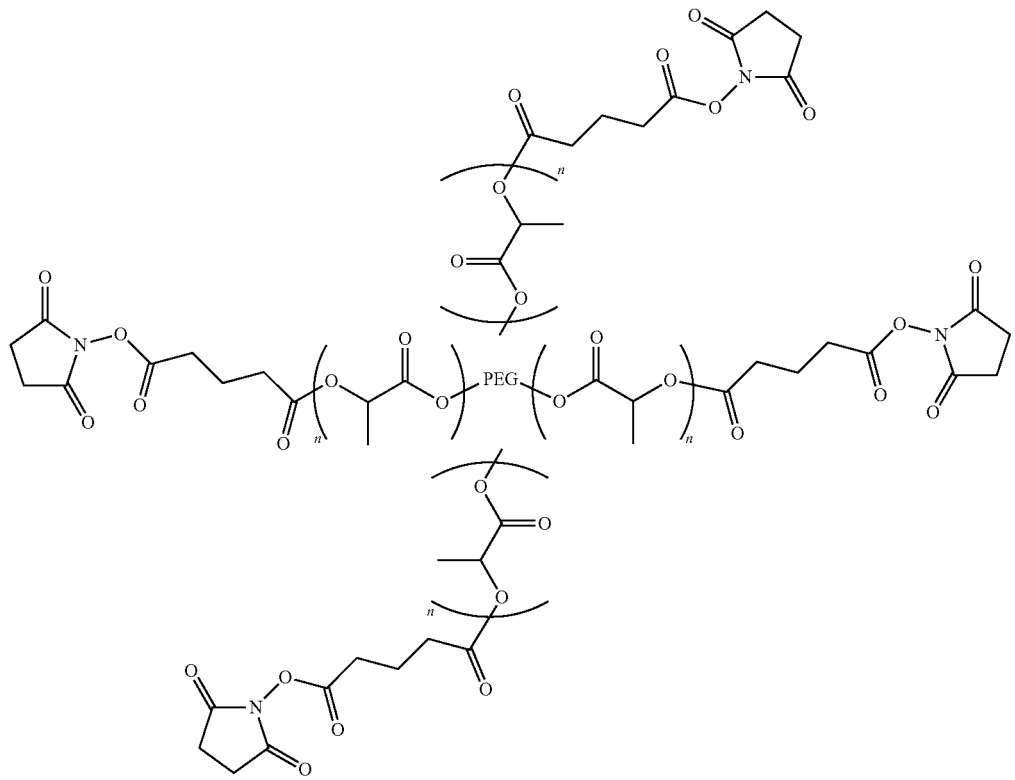

PEG tetrasuccinimidyl lactylglutarate. In some embodiments, the dry, powdered hemostatic composition comprises a second component comprising a modified polysaccharide component comprising a starch functionalized with amine groups. In some embodiments, the amine groups are at least two bonds removed from the backbone of the starch. In some embodiments, the first and second components are able to crosslink with each other into a hemostatic hydrogel.

In another aspect, a method for controlling bleeding is described. In some embodiments, the method for controlling bleeding comprises applying a dry powder to a bleeding/wound site. In some embodiments, the dry powder comprises a first component comprising a modified polysaccharide component comprising a plurality of polysaccharide chains functionalized with electrophilic groups capable of reacting with amine groups. In some embodiments, the first modified polysaccharide component comprises one or more modified polysaccharides chosen from a) a plurality of dry, porous, microspheres formed of crosslinked starch functionalized with the electrophilic groups, and b) hydrolyzed, uncrosslinked starch functionalized with the electrophilic groups. In some embodiments, the dry powder comprises a second component comprising a protein. In some embodiments, a hemostatic hydrogel is formed via crosslinking of the first component and the second component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first component comprising a modified polysaccharide component comprising a plurality of polysaccharide chains functionalized with electrophilic groups capable of reacting with amine groups, wherein the first modified polysaccharide component comprises one or more modified polysaccharides chosen from: a) a plurality of dry, porous, microspheres formed of crosslinked starch functionalized with the electrophilic groups, and b) hydrolyzed, uncrosslinked starch functionalized with the electrophilic groups; and a second component comprising a multifunctionalized polyalkylene oxide-based polymer comprising amine groups or a corresponding salt thereof. In some embodiments, a hemostatic hydrogel is formed via crosslinking of the first component and the second component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first component comprising a multifunctionalized polyalkylene-based polymer comprising electrophilic groups comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry powder comprises a second component comprising a modified polysaccharide component comprising a plurality of polysaccharide chains functionalized with amine groups. In some embodiments, a hemostatic hydrogel is formed via crosslinking of the first component and the second component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first component comprising hydrolyzed, uncrosslinked starch functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry powder comprises a second component comprising hydrolyzed, uncrosslinked starch functionalized with amine groups. In some embodiments, a hemostatic hydrogel is formed via crosslinking of the first component and the second component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first component comprising a first modified polysaccharide component comprising a plurality of polysaccharide chains functionalized with electrophilic groups capable of reacting with amine groups. In some embodiments, the dry powder comprises a second component comprising a second modified polysaccharide component comprising a starch functionalized with amine groups. In some embodiments, the amine groups are at least two bonds removed from the backbone of the starch. In some embodiments, a hemostatic hydrogel is formed via crosslinking of the first component and the second component at the bleeding/wound site able to reduce or stop bleeding at the bleeding/wound site.

In some embodiments, the method comprises applying a dry powder comprising a first dry powder component and a second dry component to a bleeding/wound site. In some embodiments, the first dry powder component comprises a plurality of polysaccharide chains functionalized with electrophilic groups capable of reacting with amine groups. In some embodiments, the first modified polysaccharide component comprises one or more modified polysaccharides chosen from a) a plurality of dry, porous, microspheres formed of crosslinked starch functionalized with the electrophilic groups, and b) hydrolyzed, uncrosslinked starch functionalized with the electrophilic groups. In some embodiments, the second dry powder component comprises a plurality of polysaccharide chains functionalized with amine groups. In some embodiments, the second modified polysaccharide component comprises one or more modified polysaccharides chosen from a) a plurality of dry, porous, microspheres formed of crosslinked starch functionalized with the amine groups, and b) hydrolyzed, uncrosslinked starch functionalized with the amine groups. In some embodiments, a hemostatic hydrogel is formed via crosslinking of the first dry powder component and the second dry powder component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first dry powder component comprising a plurality of polysaccharide chains functionalized with electrophilic groups capable of reacting with amine groups. In some embodiments, the dry powder comprises a second dry powder component comprising a starch functionalized with amine groups. In some embodiments, the amine groups are at least two bonds removed from the backbone of the starch. In some embodiments, a hemostatic hydrogel is formed via crosslinking of the first dry powder component and the second dry powder component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first dry powder component comprising a plurality of first biodegradable microporous microspheres comprising hydrolyzed starch crosslinked with glycerol ether or polyglycerol ether linkages, such as 1,3,-oxy-propan-2-ol linkages, functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry powder comprises a second dry powder component comprising a plurality of second biodegradable microporous microspheres comprising hydrolyzed starch crosslinked with glycerol ether or polyglycerol ether linkages, such as 1,3,-oxy-propan-2-ol linkages, functionalized with amine groups. In some embodiments, a hemostatic hydrogel is formed via crosslinking of the first dry powder component and the second dry powder component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first dry powder component comprising hydrolyzed, uncrosslinked starch functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry powder comprises a second dry powder component comprising hydrolyzed, uncrosslinked starch functionalized with amine groups. In some embodiments, a hemostatic hydrogel is formed via crosslinking of the first dry powder component and the second dry powder component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first component comprising a plurality of first modified microporous microspheres comprising hydrolyzed starch crosslinked with glycerol ether or polyglycerol ether linkages, such as 1,3,-oxy-propan-2-ol linkages, functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry powder comprises a plurality of second modified microporous microspheres comprising hydrolyzed starch crosslinked with glycerol ether or polyglycerol ether linkages, such as 1,3,-oxy-propan-2-ol linkages, functionalized with amine groups. In some embodiments, a hemostatic hydrogel is formed via crosslinking of the first component and the second component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first powder component comprising a plurality of modified microporous microspheres comprising hydrolyzed starch crosslinked with glycerol ether or polyglycerol ether linkages comprising at least 1,3,-oxy-propan-2-ol linkages, and functionalized with ligands comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry powder comprises a second dry powder component comprising a protein. In some embodiments, a hemostatic hydrogel is formed via crosslinking of the first component and the second component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first powder component comprising a multifunctionalized polymer comprising electrophilic groups comprising leaving groups selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl. In some embodiments, the dry powder comprises a second dry powder component comprising a plurality of modified microporous microspheres comprising hydrolyzed starch crosslinked with glycerol ether or polyglycerol ether linkages comprising at least 1,3,-oxy-propan-2-ol linkages, functionalized with amine groups. In some embodiments, a hemostatic hydrogel is formed via crosslinking of the first component and the second component at the bleeding/wound site able to reduce or stop bleeding at the bleeding/wound site.

In some embodiments, the method for controlling bleeding comprises applying a dry powder to a bleeding/wound site. In some embodiments, the dry powder comprises a first component comprising a multifunctionalized polyalkylene oxide-based polymer selected from the group consisting of

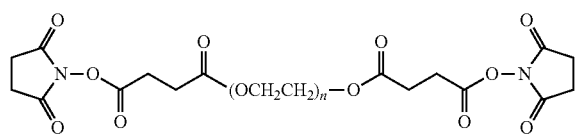

Poly(ethylene glycol) disuccinimidyl succinate, I

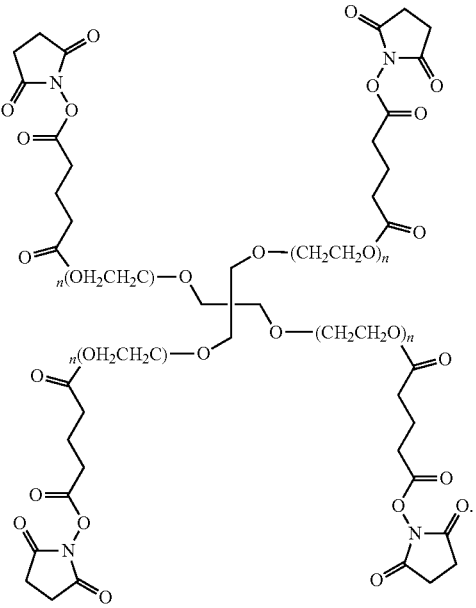

PEG Tetrasuccinimidyl Glutarate, and

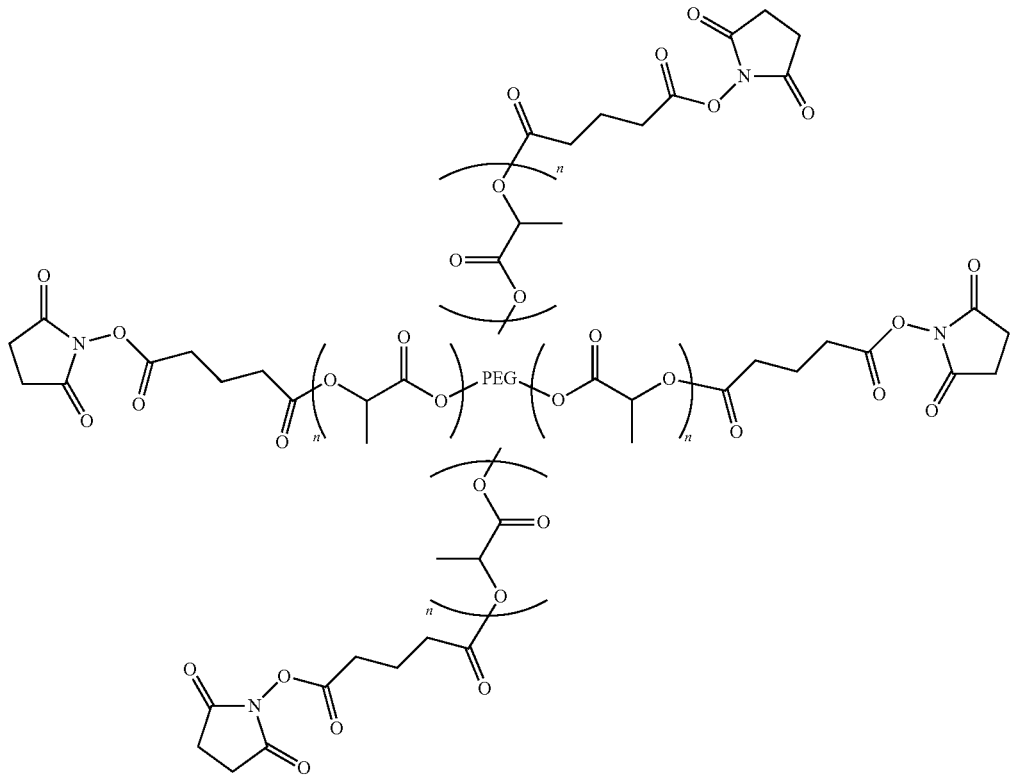

PEG tetrasuccinimidyl lactylglutarate. In some embodiments, the dry powder comprises a second component comprising a modified polysaccharide component comprising a starch functionalized with amine groups. In some embodiments, the amine groups are at least two bonds removed from the backbone of the starch. In some embodiments, a hemostatic hydrogel is formed via crosslinking of the first component and the second component at the bleeding/wound site able to reduce or stop bleeding at the bleeding/wound site.

In another aspect, isolated modified polysaccharides are provided. In some embodiments, the isolated modified polysaccharide comprises hydrolyzed, uncrosslinked starch functionalized with electrophilic groups capable of reacting with amine groups.

In another aspect, dried, isolated starch compositions are provided. In some embodiments, the dried, isolated starch composition comprises starch functionalized with N-oxysulfosuccinimidyl groups.

In another aspect, methods of making an isolated modified polysaccharide are provided. In some embodiments, the method comprises exposing hydrolyzed, uncrosslinked starch, a coupling agent, and an electrophilic group precursor to a liquid solution, such that the hydrolyzed, uncrosslinked starch is functionalized with electrophilic groups; and removing the resulting hydrolyzed, uncrosslinked starch functionalized with electrophilic groups from at least some of the liquid solution to provide the isolated modified polysaccharide comprising the hydrolyzed, uncrosslinked starch functionalized with electrophilic groups.

In one aspect, a modified polysaccharide is provided. In some embodiments, the modified polysaccharide comprises a first modified polysaccharide component comprising a plurality of polysaccharide chains functionalized with electrophilic groups capable of reacting with amine groups. In some embodiments, the first modified polysaccharide component comprises one or more modified polysaccharides chosen from a) a plurality of dry, porous, microspheres formed of crosslinked starch functionalized with the electrophilic groups, and b) hydrolyzed, uncrosslinked starch functionalized with the electrophilic groups. In some embodiments, the modified polysaccharide comprises a second modified polysaccharide component comprising a plurality of polysaccharide chains functionalized with amine groups. In some embodiments, the second modified polysaccharide component comprises one or more modified polysaccharides chosen from a) a plurality of dry, porous, microspheres formed of crosslinked starch functionalized with the amine groups, and b) hydrolyzed, uncrosslinked starch functionalized with the amine groups. In some embodiments, the first and second modified polysaccharide components are able to crosslink with each other to form a hemostatic hydrogel.

In some embodiments, the modified polysaccharide comprises a first modified polysaccharide component comprising a plurality of polysaccharide chains functionalized with electrophilic groups capable of reacting with amine groups. In some embodiments, the modified polysaccharide comprises a second modified polysaccharide component comprising a starch functionalized with amine groups. In some embodiments, the amine groups are at least two bonds removed from the backbone of the starch.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
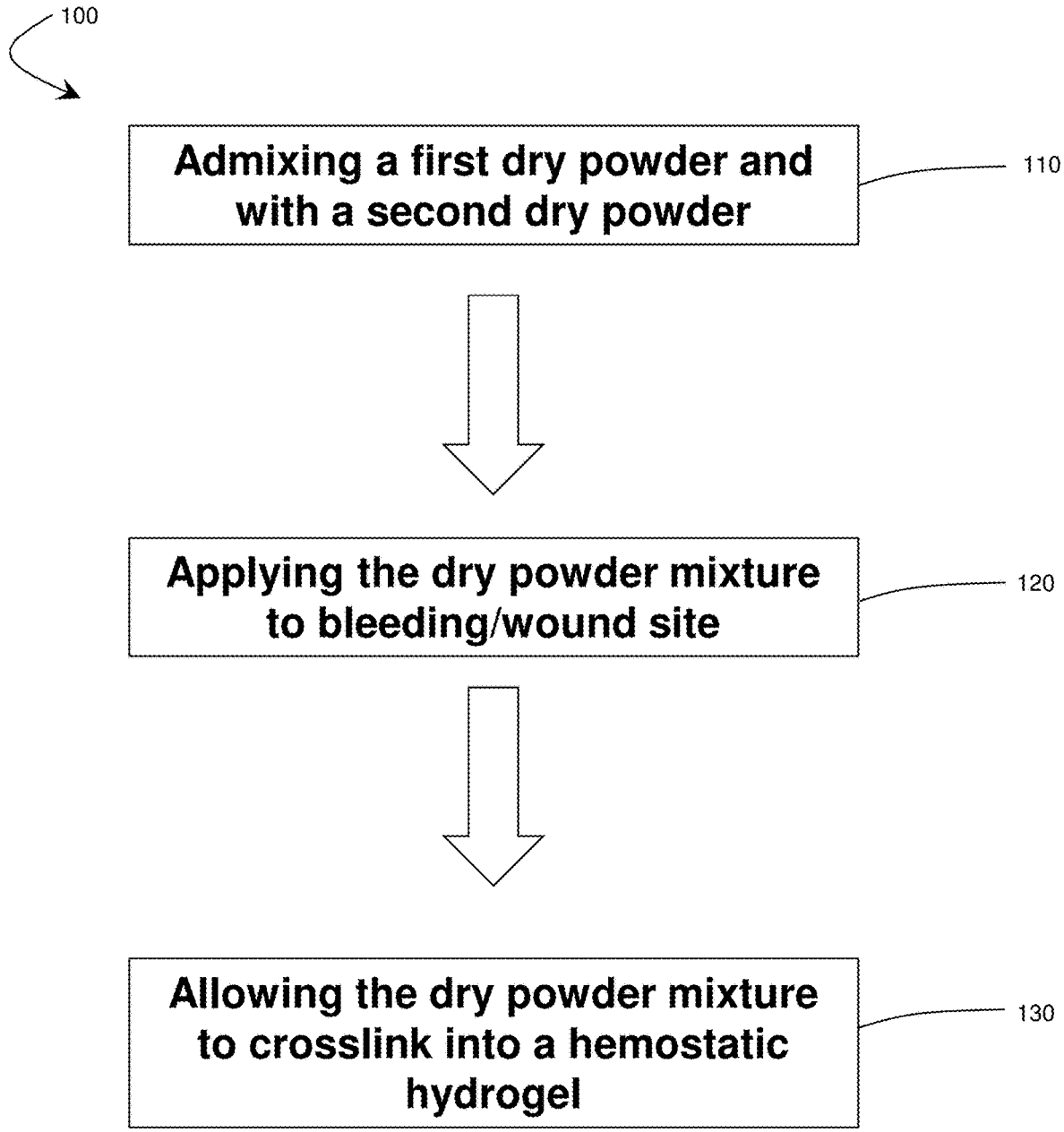
FIG. 1 shows, in accordance with certain embodiments, exemplary steps in a method for forming a hemostatic hydrogel with a dry powdered mixture.

Compositions and methods related to powdered hemostats comprising one or more functionalized polysaccharides that crosslink during and/or after application to a bleeding site are generally described. For certain embodiments involving dry powdered hemostats, upon exposure to an aqueous liquid, a dry powdered mixture of reactive hemostat components may crosslink to from a hemostatic hydrogel. Exposure to an aqueous liquid may be achieved as the dry, powdered, crosslinking compositions are applied to a bleeding/wound site comprising blood and/or other bodily fluids. Additionally, the powdered compositions may be delivered to a bleeding/wound site as a powder, in certain embodiments. In addition to, or instead of, use as a hemostatic material for controlling or stopping bleeding, in certain embodiments, compositions and methods described herein may be useful for a variety of other medical applications, such as postsurgical adhesion barriers, sealants and wound dressings.

As used herein, the term "crosslink" refers to a chemical reaction between two or more similar or dissimilar polymers, copolymers, oligomers, and/or macromers that links the two or more similar or dissimilar polymers, copolymers, oligomers, or macromers via formation of at least one covalent bond and/or ionic bond, or a chain extension between one or more polymers, copolymers, oligomers, and/or macromers to provide a longer chain of the one or more polymers, copolymers, oligomers, and/or macromers via formation of at least one covalent bond and/or ionic bond.

For certain embodiments in which the hemostat is used in dry powder form, a multi-component (e.g., two component, three component, etc.) composition may be used. In certain embodiments, one or more components comprises a modified polysaccharide (e.g., a starch functionalized with reactive groups). In some embodiments, a component of the dry powder hemostat comprises a multifunctionalized polyalkylene oxide-based component, a protein, or another nucleophilic polymer that is capable of crosslinking with a modified polysaccharide. The dry powder may also comprise a crosslinking initiator that initiates crosslinking of the one or more modified polysaccharides and other components of the dry powder In certain embodiments related to the multi-component composition, crosslinking to form a hemostatic hydrogel occurs upon exposure of the composition to an aqueous liquid, such as at a bleeding/wound site. In some cases, the structural properties (e.g., particle size and/or particle density) of certain components of the dry powder composition may affect the time required for the dry powder composition to crosslink and form a hemostatic hydrogel or may affect the degree of crosslinking or both.

In some embodiments wherein the hemostat is used in dry powder form, a two-component reactive dry powder mixture may be used. In certain embodiments, the first component may comprise a first dry powder comprising a functionalized polysaccharide (e.g., starch) and/or a multifunctionalized polyalkylene oxide-based component, and a second component may comprise a second dry powder (which may also be a functionalized polysaccharide, a multifunctionalized polyalkylene oxide-based component and/or protein (e.g., albumin)) able to crosslink with the first component. Upon exposure to an aqueous liquid, the second component may crosslink with the first component and/or a crosslinking initiator may be used in certain cases to initiate crosslinking between two different reactive powdered hemostats, resulting in a crosslinked hemostatic hydrogel that is capable of stopping and/or reducing bleeding at the bleeding/wound site. Hemostatic precursors comprising crosslinking functionalized polysaccharide (e.g., starch)-based components, multifunctionalized polyalkylene oxide-based components (such as polyethylene glycol (PEG)), and/or protein (e.g., albumin) may help alleviate issues related to the need for manual compression by forming a hydrogel with tissue adherence in certain embodiments.

As indicated above, in certain embodiments, modified polysaccharide is employed as a hemostatic material. In some embodiments, the modified polysaccharide is provided as a dry, powdered composition comprising a first dry powder and a second dry powder. A first modified polysaccharide component may comprise a plurality of polysaccharide chains (e.g., hydrolyzed starch chains) functionalized with electrophilic groups and the second modified polysaccharide component may comprise a plurality of polysaccharide chains functionalized with nucleophilic groups reactive with the electrophilic groups of the first dry powder (e.g., amines). In some cases, the first modified polysaccharide component comprises one or more polysaccharides chosen from one or more of a) a plurality of dry, porous microspheres formed of cross-linked starch functionalized with electrophilic groups that are capable of reacting with amines, b) hydrolyzed, uncrosslinked starch functionalized with electrophilic groups capable of reacting with amines, and c) starch functionalized with electrophilic groups capable of reacting with amines, where the electrophilic groups are at least two bonds, at least three bonds, at least four bonds, or more removed from the backbone of the starch. In certain cases, the second modified polysaccharide component comprises one or more modified polysaccharides chosen from one or both of: a) a plurality of dry, porous microspheres formed of crosslinked starch functionalized with amine groups, b) hydrolyzed, uncrosslinked starch functionalized with amine groups, and c) starch functionalized with amine groups, where the electrophilic groups are at least two bonds, at least three bonds, at least four bonds, or more removed from the backbone of the starch. The second modified polysaccharide component may crosslink with the first modified polysaccharide component upon exposure to an aqueous liquid and/or a crosslinking initiator (e.g., a base or basic buffer salt solution). In some embodiments, a modified polysaccharide component (e.g., comprising functionalized microporous microspheres comprising crosslinked hydrolyzed starch, comprising functionalized uncrosslinked hydrolyzed starch, and/or comprising a starch with reactive groups at least two bonds, at least three bonds, at least four bonds, or more removed from the backbone of the starch) can crosslink with a material other than another modified polysaccharide component (e.g., a multifunctionalized polymer such as a multifunctionalized polyalkylene oxide as described below, a protein such as albumin, etc.), as described in more detail below.

As indicated above, in some embodiments the dry powder composition comprises modified polysaccharides that are functionalized with reactive groups. Modified polysaccharides, as useful herein, comprise polysaccharide chains modified with functional groups (e.g., functionalized polysaccharide chains). Examples of polysaccharides that may be modified as described herein, include, but are not limited to, starches, celluloses, chitosans, pectins, dextrans, or derivatives or combinations thereof. The use of polysaccharide chains in hemostatic applications can be beneficial due to their general biocompatibility and, in some cases biodegradability.

The modified polysaccharide may comprise a first modified polysaccharide component. The first modified polysaccharide component comprises, in accordance with certain embodiments, a plurality of polysaccharide chains functionalized with electrophilic groups capable of reacting with nucleophilic groups, such as amine groups. For example, the first modified polysaccharide component may comprise starch (e.g., hydrolyzed, uncrosslinked starch, or dry, porous, microspheres formed of crosslinked starch) functionalized with leaving groups selected from the group G, where G is N-oxysuccinimidyl, N-oxysulfosuccinimidyl, N-oxymaleimidyl, N-oxyphthalimidyl, nitrophenoxyl, N-oxyimidazolyl, and tresyl).

The modified polysaccharide may in some embodiments comprise a second modified polysaccharide component. The second modified polysaccharide component comprises, in accordance with certain embodiments, a plurality of polysaccharide chains functionalized with nucleophilic groups, such as amine groups. For example, the second modified polysaccharide component may comprise starch (e.g., hydrolyzed, uncrosslinked starch, dry, porous, microspheres formed of crosslinked starch, or a modified starch such as hydroxyalkyl starch or carboxyalkyl starch) functionalized with ligands comprising amino acids selected from the group consisting of lysine, glycine, arginine, and alanine. In some embodiments, the second modified polysaccharide comprises amine groups bound to the polysaccharide via other types of moieties, such as those that comprise moieties comprising silicon, as described in more detail below.

In some embodiments, the first and second modified polysaccharide components of the modified polysaccharide are able to crosslink with each other into a hemostatic hydrogel. In certain embodiments, the crosslinking between the first modified polysaccharide component and second modified polysaccharide component is achieved when the leaving group of the electrophilic groups (e.g., a leaving group from the group G above) react with an amine group (e.g., a primary amine or secondary amine from an amino acid ligand or a silane-containing moiety attached to a modified polysaccharide chain) to form a covalent bond (e.g., an amide bond). The formation of a hemostatic hydrogel from the crosslinking of a first modified polysaccharide component and a second polysaccharide component may provide a highly absorbent, easily localizable hemostatic agent with relatively rapid resorption rates in the body. The formation of such a hydrogel via crosslinking of the first and second polysaccharide components can be initiated, in some embodiments, by the exposure of the modified polysaccharide to an aqueous medium (e.g., blood). In some embodiments, the crosslinking reaction is initiated by a crosslinking initiator. In some embodiments, the crosslinking initiator comprises a base or a basic buffer (e.g., a basic crosslinking initiator) of the type and/or pH ranges described herein. In general, it should be understood that the polysaccharide-based and polyalkylene oxide-based functionalized components described above and below may be used independently or in combination with each other in certain cases.

In certain embodiments, the first and/or second modified polysaccharide components may comprise a plurality of dry, porous, microspheres. In some embodiments, the microspheres are formed of crosslinked starch (e.g., crosslinked, hydrolyzed starch). In certain embodiments where the first and/or second modified polysaccharide component comprise a plurality of dry, porous, microspheres, the microspheres of the first and/or second component are able to crosslink with the modified polysaccharides of the other modified polysaccharide component (e.g., the first and second modified polysaccharide components are able to crosslink with each other, with at least one of the first and second modified polysaccharide components comprising dry, porous, microspheres). A resulting hydrogel comprising the crosslinked dry, porous microspheres formed of crosslinked starch can, in certain cases, have certain advantageous properties. For example, a hemostatic hydrogel comprising crosslinked dry, porous microspheres formed of crosslinked starch may have good strength, flexibility, and tissue adhesion at a bleeding/wound site, while also having relatively high blood absorption. Further, in certain cases and without being limited by theory, a hemostatic hydrogel comprising crosslinked dry, porous microspheres formed of crosslinked starch may accelerate hemostasis relative to other compositions at least in part via the hydration of the microspheres due to their porous (e.g., microporous) nature, thereby providing a molecular sieving effect that may result in selectively removing water from blood and/or by initiating a coagulation cascade, for example, by concentrating endogenous coagulants and formed elements at the surface of the particles to accelerate coagulation and hemostasis at the bleeding site. In some embodiments, the dry, porous (e.g., microporous) microspheres described herein are formed of crosslinked hydrolyzed starch (as described in more detail below). In certain cases, microspheres comprising crosslinked hydrolyzed starch may have beneficial properties in hemostatic applications relative to powders comprising crosslinked non-hydrolyzed starch (e.g., raw starch). For example, hydrolyzed starch chains have a lower weight average molecular weight than chains of non-hydrolyzed starch. Such lower molecular weight chains can, in some cases, reduce or even eliminate the presence of crystalline regions in materials containing hydrolyzed starch. In contrast, crystalline regions are often present in materials containing non-hydrolyzed starch with higher molecular weight chains (e.g., raw starch granules). Without being bound by any particular theory, such crystalline regions may in some cases contribute to relatively slow degradation (e.g., biodegradation) and elicit inflammatory responses when materials containing the crystalline regions are implanted (e.g., in a hemostatic composition). As such, porous microspheres formed of crosslinked hydrolyzed starch may, in certain cases, mitigate such deleterious phenomena (slow degradation and eliciting of inflammation).

As mentioned above, in some embodiments, a dry, powdered hemostatic composition is provided. In some cases, the dry powdered composition (e.g., a mixture of a dry powders) comprises the modified polysaccharide described herein. In some embodiments, the dry powdered composition comprises a first component (e.g., first dry powder). In some embodiments, the first component comprises a plurality of first modified microporous (or porous) microspheres comprising hydrolyzed starch crosslinked with glycerol ether or polyglycerol ether linkages, such as 1,3,-oxy-propan-2-ol linkages, functionalized with ligands comprising leaving groups selected from the same group as G described above. In some such embodiments, a second component (e.g., second dry powder) is provided. In some embodiments, the second component comprises a plurality of second modified microporous microspheres comprising hydrolyzed starch crosslinked glycerol ether or polyglycerol ether linkages, such as 1,3,-oxy-propan-2-ol linkages, functionalized with ligands comprising amino acids selected from the group consisting of lysine, glycine, arginine; and alanine. In certain embodiments, the first and second components (e.g., first and second dry powders) are able to crosslink into a hemostatic hydrogel upon exposure to water (e.g., at a bleeding site). The dry powdered composition can be used to control bleeding, in accordance with certain embodiments, according to the method described below.

In some embodiments, the first and/or second modified polysaccharide components comprise a dry powder formed of hydrolyzed, uncrosslinked starch. In some such embodiments, these first and second modified polysaccharide components (at least one of which may comprise a dry powder form of hydrolyzed starch) are able to crosslink with each other to form the hemostatic hydrogel upon exposure to an aqueous medium. A resulting hydrogel that is formed by the crosslinking of the functionalized, hydrolyzed, uncrosslinked starch can, in certain cases, have certain advantageous properties. For example, a hemostatic hydrogel that is formed by the crosslinking of the functionalized, hydrolyzed, uncrosslinked starch may, in some cases, have good strength, flexibility, and tissue adhesion at a bleeding/wound site, while also having retaining a relatively high water solubility relative to other compositions that may comprise starch that is not hydrolyzed. A relatively high water solubility, may, in certain cases, increase overall water uptake upon exposure, for example to a bleeding/wound site, which may accelerate the formation of hydrogel and hemostasis. In some embodiments, the presence of hydrolyzed starch (e.g., functionalized hydrolyzed starch) in the hemostatic hydrogel may result in the hemostatic hydrogel having beneficial properties relative to hemostatic hydrogels formed of non-hydrolyzed starch. As mentioned elsewhere herein, hydrolyzed starch chains typically have a lower weight average molecular weight than chains of non-hydrolyzed starch (e.g., raw starch). Such lower molecular weight chains can, in some cases, reduce or even eliminate the presence of crystalline regions in materials containing hydrolyzed starch. In contrast, crystalline regions are often present in materials containing non-hydrolyzed starch with higher molecular weight chains (e.g., raw starch granules). Without being bound by any particular theory, such crystalline regions may in some cases contribute to relatively slow degradation (e.g., biodegradation) and elicit inflammatory responses when materials containing the crystalline regions are implanted (e.g., as part of a hemostatic composition). As such, hemostatic hydrogels formed by the crosslinking of functionalized, hydrolyzed, uncrosslinked starch may, in certain cases, mitigate such deleterious phenomena (slow degradation and eliciting of inflammation) relative to materials containing non-hydrolyzed starch.

In some embodiments, the first and/or second modified polysaccharide components comprise a polysaccharide in which the reactive groups (e.g., electrophilic groups, nucleophilic groups (e.g., amine groups)) are spaced apart from the backbone of the polysaccharide by a multi-bond spacer. It has been observed that having the reactive groups (e.g., electrophilic groups, amine groups) of the modified polysaccharide spaced apart from the backbone of the polysaccharide by a multi-bond spacer, as opposed to being bound closely (e.g., within just 1 bond of) of the backbone, may, in some cases, improve the crosslinking ability of the modified polysaccharide component. Without wishing to be bound by any particular theory, having more space between the reactive groups may (e.g., via a linking moiety of sufficient length) contribute at least in part to faster crosslinking (and/or greater extent of crosslinking) and/or beneficial physical properties of resulting hydrogels (e.g., enhanced swelling) due to greater conformational freedom for the reactive groups and lower steric hindrance compared to reactive groups bound closely to the backbone. In some embodiments, the first polysaccharide component comprises a starch functionalized with electrophilic groups, as described above. In some such embodiments, the electrophilic groups are at least two, at least three, at least four, at least five, at least six, at least seven, at least 8, at least 10, and/or up to 15, up to 20, or more bonds removed from the backbone of the starch. In some embodiments, the second polysaccharide component comprises a starch functionalized with amine groups, as described above. In some such embodiments, the amine groups are at least two, at least three, at least four, at least five, at least six, at least seven, at least 8, at least 10, and/or up to 15, up to 20, or more bonds removed from the backbone of the starch. In the present context, the term "bond" referred to in the phrases "number of bonds removed" or "spaced apart from by a number of bonds" refers to a bond length of any of a single bond, double bond, or triple bond creating such spacing. For example, in a compound having a structure A-C-B, B is two bonds removed from A, while in a compound having structure A-C=B, B is also two bonds removed from A, because both the single bond and the double bond are counted identically in this context. The terms "number of bonds removed" or "spaced apart from by a number of bonds" are based on the connectivity of the compound and not an absolute distance, and as such, are conformation-independent. Additionally, in the present context, the backbone of a polysaccharide is considered to be the chain of repeating monosaccharide units. For example, in the present context, the backbone of the starch is considered to be the chain of repeating $C_6H_{10}O_5$ glucose units of the starch. Structures (A) and (B) are shown below purely for illustrative purposes.

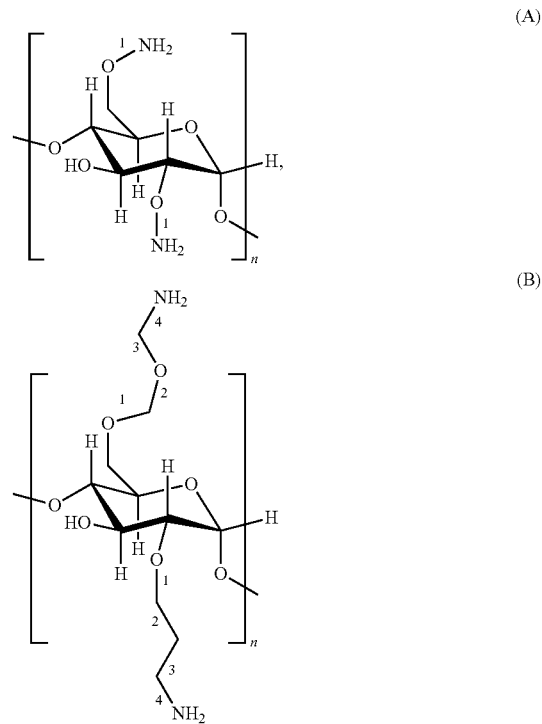

In exemplary structure (A), the amine groups are only one bond removed from the starch backbone (as can be understood from the numbers on the bonds shown in structure (A)), while in exemplary structure (B), the amine groups are 4 bonds removed from the starch backbone (as can be understood from the numbers on the bonds shown in structure (B)). In some embodiments, a modified polysaccharide comprising polysaccharide chains having structure (B) is capable of crosslinking with another component (e.g., a first modified polysaccharide component or a multifunctionalized polyalkylene oxide-based polymer) to a greater extent or at a faster rate than is a modified polysaccharide comprising polysaccharide chains having structure (A).

Those of ordinary skill, with the benefit of this disclosure, would understand how to make a modified polysaccharide comprising reactive groups (e.g., electrophilic groups, amine groups) that are spaced apart from the backbone of the polysaccharide by a desired number of bonds (e.g., four bonds as shown in structure (B)). As one non-limiting example, in some embodiments, the reactive groups (e.g., electrophilic groups, amine groups) are introduced to a starch that is modified prior to being functionalized with the reactive groups. In some such embodiments, the modification to the starch includes the introduction of moieties that position at least some of the reactive hydroxy groups of the starch farther away from the backbone relative to the unmodified (e.g., native) starch. For example, in some embodiments, the first and/or second modified polysaccharide is formed by functionalizing a hydroxyalkyl starch. Hydroxyalkyl starches (e.g., hydroxymethyl starch, hydroxyethyl starch, etc.) are known to those of skill in the art. In some embodiments, the first modified polysaccharide comprises a hydroxyalkyl starch functionalized with the electrophilic groups. As one particular example, in some embodiments, the first modified polysaccharide comprises a hydroxyethyl starch functionalized with the electrophilic groups. In some embodiments, the second modified polysaccharide comprises a hydroxyalkyl starch functionalized with the amine groups. As one particular example, in some embodiments, the second modified polysaccharide comprises a hydroxyethyl starch functionalized with the amine groups.

In some embodiments, other strategies for positioning the reactive groups at a desired distance away from the backbone of the polysaccharide may be employed. For example, in some embodiments, a starch is not modified prior to functionalization, but the functionalization involves coupling the unmodified starch to a moiety that comprises a sufficient number of bonds between the reactive group (e.g., electrophilic group, amine group) and the point of coupling between the starch and the moiety to achieve the desired distance between the reactive group and the backbone.

Starch, in its native (unhydrolyzed) form, is a polysaccharide biopolymer comprising amylose and amylopectin. The polysaccharide chains of starch are typically a combination of long, linear chains and branched cluster. Native starch typically forms gelatinous mixtures with water. Starch is generally derived from plant sources such as potatoes.

When native starch is hydrolyzed into smaller poly-glucose chains, it can form a hydrolyzed starch composition that is water-soluble. In some embodiments, the resulting hydrolyzed, uncrosslinked starch can be functionalized (e.g., with a leaving group or a ligand comprising an amine). In some embodiments, the hydrolyzed starch can be crosslinked (e.g., with a crosslinking agent such as epichlorohydrin) to form porous or microporous microspheres. Some such microporous microspheres may serve as good hemostatic agents due in part to their ability to absorb water from blood without absorbing certain other components of blood.

Hydrolyzed starch generally refers to poly-glucose chains derived from the partial hydrolysis of native starch (e.g., vegetable starch). Hydrolyzed starch and its properties are described in detail in Carlstedt, J., Wojtasz, J., Fyhr, P., & Kocherbitov, V. (2014); "Hydration and the phase diagram of acid hydrolyzed potato starch. Carbohydrate polymers," 112, 569-577, which is incorporated herein by reference in its entirety. Hydrolyzed starch can be produced, for example, by treating starch with acid at elevated temperatures. More specifically, starch can be treated with dilute aqueous or dilute alcohol solutions containing a mineral acid (e.g., hydrochloric acid or sulfuric acid) at temperatures below the gelatinization temperature of the starch, followed by neutralization and washing, and drying. For example, hydrolyzed starch particles or microspheres can be produced via the acid-hydrolysis of potato starch, followed by spray-drying. Hydrolyzed starch can also be produced by enzymatic digestion processes, with, for example, α-amylase. An example of such a hydrolyzed starch composition is maltodextrin. Various protocols and approaches to the enzymatic production of maltodextrin are taught and evaluated in Sadeghi, A., Shahidi, F., Mortazavi, S. A., & Mahalati, M. N. (2008). "Evaluation of different parameters effect on maltodextrin production by-amylase Termamyl 2-x," World Applied Sciences Journal, 3(1), 34-39, which is incorporated herein by reference in its entirety. Maltodextrin is also available for sale by commercial vendors such as Sigma Aldrich, Avebe, Roquette, Ingredion, and Nowamyl. Maltodextrins, according to the usage in the present disclosure, can also be produced via acid-hydrolysis of starch. In some embodiments, a hydrolyzed, uncrosslinked starch functionalized with electrophilic groups is or comprises maltodextrin functionalized with electrophilic groups (e.g., the leaving groups of G). In some embodiments, a hydrolyzed, uncross-linked starch functionalized with amine groups is or comprises maltodextrin functionalized with amine groups.

A hydrolyzed starch composition can be described in terms of its dextrose equivalents (DE). A dextrose equivalent is a measure of the amount of reducing sugars present in a sugar product, and the dextrose equivalents for a poly-glucose composition is indicative of the degree of conversion (e.g., via hydrolysis) from starch (DE of ~0) to dextrose/glucose (DE of 100). The DE of a composition can be measured, for example, using Lane-Eynon titration based on the reduction of copper(II) sulfate in an alkaline tartrate solution. As one example, maltodextrins generally have a DE from 3 to 20.

In some embodiments, a hydrolyzed, uncrosslinked starch functionalized with electrophilic groups has a relatively high DE value. Having a relatively high DE value may be associated with improved water solubility of dry powdered compositions, in some instances. In some embodiments, a first component (e.g., dry powder) comprises hydrolyzed, uncrosslinked starch functionalized with electrophilic groups having a DE of greater than or equal to 1, greater than or equal to 1.5, greater than or equal to 2, greater than or equal to 2.5, greater than or equal to 3, greater than or equal to 4, greater than or equal to 5, greater than or equal to 8, greater than or equal to 10, greater than or equal to 12, or greater. In some embodiments, a first component (e.g., dry powder) comprises hydrolyzed, uncrosslinked starch functionalized with electrophilic groups having a DE of less than or equal to 20, less than or equal to 18, less than or equal to 15, less than or equal to 13, less than or equal to 12, less than or equal to 10, or less. Combinations of these ranges (e.g., a DE of greater than or equal to 1 and less than or equal to 20, greater than or equal to 3 and less than or equal to 12) are possible. In some embodiments, a first component (e.g., dry powder) comprises maltodextrin functionalized with electrophilic groups having a DE of 12.

In some embodiments, a hydrolyzed, uncrosslinked starch functionalized with amine groups has a relatively high DE value. In some embodiments, a second component (e.g., dry powder) comprises hydrolyzed, uncrosslinked starch functionalized with amine groups having a DE of greater than or equal to 1, greater than or equal to 1.5, greater than or equal to 2, greater than or equal to 2.5, greater than or equal to 3, greater than or equal to 4, greater than or equal to 5, greater than or equal to 8, greater than or equal to 10, greater than or equal to 12, or greater. In some embodiments, a second component (e.g., dry powder) comprises hydrolyzed, uncrosslinked starch functionalized with amine groups having a DE of less than or equal to 20, less than or equal to 18, less than or equal to 15, less than or equal to 13, less than or equal to 12, less than or equal to 10, or less. Combinations of these ranges (e.g., a DE of greater than or equal to 1 and less than or equal to 20, greater than or equal to 3 and less than or equal to 12) are possible. In some embodiments, a second component (e.g., dry powder) comprises maltodextrin functionalized with amine groups having a DE of 12.

The poly-glucose chains of hydrolyzed starch typically have weight averaged molecular weights as measured by size exclusion chromatography-multi-angle laser light scattering (SEC-MALLS) in the range of greater than or equal to 1,000 Da to 1,000,000 Da. In some embodiments, the poly-glucose chains of hydrolyzed starch have weight averaged molecular weights of greater than or equal to 1,000 Da, greater than or equal to 2,000 Da, greater than or equal to 5,000 Da, greater than or equal to 10,000 Da, greater than or equal to 20,000 Da, greater than or equal to 30,000 Da, or greater. In some embodiments, the poly-glucose chains of hydrolyzed starch have weight averaged molecular weights of less than or equal to 1,000,000 Da, less than or equal to 500,000 Da, less than or equal to 250,000 Da, less than or equal to 100,000 Da, less than or equal to 75,000 Da, less than or equal to 50,000 Da, less than or equal to 40,000 Da, or less. Combinations (e.g., greater than or equal to 1,000 Da and less than or equal to 1,000,000 Da, greater than or equal to 1,000 Da and less than or equal to 100,000 Da, greater than or equal to 1,000 Da and less than or equal to 40,000 Da) are possible.

As mentioned above, hydrolyzed starch, in contrast to native starch, is water-soluble. For example, hydrolyzed starch derived from the acid-hydrolysis of potato starch can be obtained in the form of a white powder that has an aqueous solubility of at least 1 wt. % (e.g., at room temperature) and as high as 50 wt. % or more (e.g., at elevated but relatively mild temperatures (e.g., at 70° C.)). Such a solubility can contribute to an ease of manipulation or modification (e.g., lyophilizing to form uniform foams, undergoing chemical reactions in homogeneous aqueous conditions, etc.).

It has been observed in the context of the present disclosure that in some instances, functionalization of a polysaccharide (e.g., a hydrolyzed starch) can affect the solubility of the resulting modified polysaccharide component (e.g., in water). It has been observed that hydrolyzed, uncrosslinked starch functionalized with certain electrophilic groups may have a greater solubility (e.g., in water) than hydrolyzed, uncrosslinked starch functionalized with other electrophilic groups. In some embodiments, a component of a dry, powdered hemostat comprises a modified polysaccharide component comprising a plurality of polysaccharide chains functionalized with electrophilic groups and/or nucleophilic groups, and the component is a dry powder having a water solubility of at least 1 wt. % (e.g., at least 2 wt. %, at least 3 wt. %, at least 4 wt. %, at least 5 wt. %, at least 8 wt. %, at least 10 wt. %, at least 12 wt. %) and/or as high as 15 wt. %, as high as 18 wt. %, as high as 20 wt. %, as high as 25 wt. %, or higher at a temperature of 37° C. One example of a suitable electrophilic group that can impart improved solubility compared to other electrophilic groups is N-oxysulfosuccinimidyl:

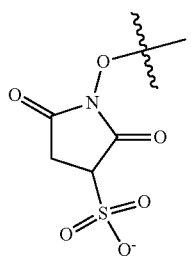 [SMILES: *ON1C(=O)CC(S(=O)(=O)[O-])C1=O]

In some embodiments, a first component of a dry powder hemostat comprises hydrolyzed, uncrosslinked starch functionalized with N-oxysulfosuccinimidyl.

Microparticles comprising polysaccharides (e.g., starch), herein referred to as microspheres, can be used as hemostatic agents, and such use is described in U.S. Pat. No. 6,060,461, which in incorporated herein by reference in its entirety. As mentioned above, the crosslinked polysaccharide chains of microspheres can be crosslinked with any suitable crosslinking agent capable of reacting with the polysaccharide chains to form chemical links between different polysaccharide chains and/or different portions of the polysaccharide chains. The chemical linkages between the crosslinked polysaccharide chains could include but are not limited to amide bonds, ester bonds, metal coordination complexes, diethers, and glycerol ethers. In some embodiments, epichlorohydrin is used as a crosslinking agent.

Epichlorohydrin is known to undergo a number of reactions in the presence of polysaccharides, as described in Hamdi G, Ponchel G. "Enzymatic degradation of epichlorohydrin crosslinked starch microspheres by alpha-amylase;" Pharm Res. 1999, June; 16(6), 867-75, which is incorporated herein by reference in its entirety. In summary, epichlorohydrin can crosslink polysaccharide (e.g., polyglucose) chains to form glycerol ether or polyglycerol ether linkages, such as 1,3-propan-2-ol linkages. Epichlorohydrin can also undergo hydrolysis, form a glycerol monoether, or polymerize without crosslinking poly-glucose chains. As such, when the polysaccharides (e.g., starch) described herein are crosslinked via epichlorohydrin, the glycerol ether and polyglycerol ether linkages formed between polysaccharide chains, while present, may, in some embodiments, not be the exclusive product between the epichlorohydrin and the uncrosslinked polysaccharide chains.

In some embodiments, the microspheres comprise crosslinked hydrolyzed starch. In some embodiments, these biodegradable microspheres comprising hydrolyzed starch are crosslinked by reacting with epichlorohydrin, resulting in glycerol ether or polyglycerol ether linkages, such as 1,3-oxy-propan-2-ol linkages.

In accordance with certain embodiments, microspheres comprising crosslinked hydrolyzed starch can be manufactured according to one or more of the methods described in the following references: U.S. Patent Publication Number 2012/0244198; Hamdi G, Ponchel G. "Enzymatic degradation of epichlorohydrin crosslinked starch microspheres by alpha-amylase," Pharm Res. 1999, June; 16(6):867-75; and Hamdi G, Ponchel G, Duchêne D. "Formulation of epichlorohydrin cross-linked starch microspheres" J Microencapsul. 2001, May-June; 18(3):373-83, all of which are incorporated herein by reference in their entirety. In certain embodiments, the microspheres are produced via the emulsification of hydrolyzed starch in an organic solvent (e.g., toluene or ethylene chloride) followed by crosslinking with epichlorohydrin.

In a specific example, which can be scaled to produce any desired quantity of final product, the dry, porous microspheres comprising crosslinked hydrolyzed starch are prepared, in accordance with certain embodiments, by dissolving 2 g of sodium hydroxide in 280 mL of purified water, to which is then added 2 g of sodium borohydride. 153 g of hydrolyzed starch is then added to the water mixture and stirred for at least 2 hours. The water mixture containing the hydrolyzed starch is then added to 450 g of toluene containing 20 g of dissolved surfactant (Rhodafac™ PA17). The temperature of the combined water and toluene emulsion is raised to 70° C., and stirred until the desired droplet size distribution is obtained. 22 g of epichlorohydrin is then added, and crosslinking is performed for 5 hours. The mixture is cooled to room temperature and allowed to settle, at which point the supernatant is removed by decanting. The resulting microspheres are washed three times with 95% ethanol, then once with 0.8% acetic acid, and then four times with purified water. The microspheres are then dehydrated with absolute ethanol and dried at 60° C.

The starch microspheres and other powders used herein may have a diameter on the microscale. In some embodiments, the microspheres have diameters in the range of from 1 μm to 1000 μm. In some embodiments, the microspheres/ powders have diameters in the range of from 10 μm to 100 μm. For example, in accordance with certain embodiments, the biodegradable microspheres comprising crosslinked hydrolyzed starch have diameters in the range of from 1 μm to 1000 μm.

In some embodiments, the microspheres have a relatively high porosity. Having a relatively high porosity can assist, in part, increasing the water uptake of the microspheres, which can be helpful in inducing hemostasis, in certain embodiments. In some embodiments, the microspheres are microporous. For example, in some embodiments, the microspheres comprising crosslinked hydrolyzed starch are microporous. In some embodiments, the microspheres have an average pore size of greater than or equal to 0.5 nm and less than or equal to 1000 nm. In some embodiments, the microspheres have an average pore size of greater than or equal to 5 nm and less than or equal to 500 nm.

The porosity of the microspheres can be controlled, for example, using the methods of U.S. Pat. No. 6,060,461. Non-limiting examples, for controlling porosity include codispersion with a differentially soluble material, particle formation from an emulsion or dispersion, and sintering of smaller sub-particles.

As mentioned above, in some embodiments, uncrosslinked polysaccharide chains and/or microspheres in the modified polysaccharide are functionalized with functional groups (e.g., electrophilic groups with leaving groups from group G described above, amine groups).

One method, in accordance with certain embodiments, for modifying microspheres with functional groups is described by U.S. Patent Publication Number 2012/0244198, which describes the modification of biodegradable microspheres comprising crosslinked hydrolyzed starch with endogenous ligands. In particular, U.S. Patent Publication Number 2012/0244198 describes attaching ligands to the hydroxyl groups of the glucose monomers of the crosslinked hydrolyzed starch via carboxylic ester bonds. The ligands, in certain embodiments, comprise at least one functional group capable of forming an ester bond. In some embodiments, the functional group capable of forming an ester bond is a carboxylic acid group (i.e., the ligand has at least one COOH group). In some embodiments, the ligands are or comprise amino acids. For example, in some embodiments, the ligands are selected from the group of lysine, glycine, arginine, and alanine.

A general procedure for modifying microspheres, in accordance with certain embodiments, is as follows. The ligand (e.g., an amino acid or other reactive ligand, 10.8 mmol) is mixed with a carbonyldiimidazole (CDI, 10.8 mmol) in 50 mL DMF and heated to 80° C. for 2 hours. The microspheres (5 g) are added to the DMF mixture, the temperature is raised to 90° C., and the mixture is stirred overnight. The reaction mixture is then washed with 250 mL of ethanol twice, washed with diluted HCl (250 mL) once, and washed with water (250 mL) twice. The material is then dehydrated with ethanol and dried overnight at 60° C. In the case of using protected ligands (e.g., an amino acid with a tert-butoxycarbonyl or Boc protecting group), the protecting group can be removed following the above procedure (e.g., removing the Boc group with trifluoroacetic acid). The general procedure may be modified as needed, depending on the ligand.

The above general procedure for attaching a ligand to the polysaccharide microspheres (e.g., the glucose monomers of the microspheres comprising crosslinked hydrolyzed starch) accordingly takes place after the formation of the microsphere. For example, in some embodiments, the above general procedure occurs after the emulsification and crosslinking of hydrolyzed starch to form biodegradable microspheres.

However, in some embodiments, the general procedure can be modified such that the attachment of the ligand to the monomers of the polysaccharide (e.g., the glucose monomers of the poly-glucose chains of hydrolyzed starch) can occur before emulsification or crosslinking, resulting in ligand-modified uncrosslinked polysaccharide chains. In some embodiments, the ligand-modified uncrosslinked polysaccharide chains are not emulsified or crosslinked at all. For example, in accordance with some embodiments, hydrolyzed starch is modified with a ligand (e.g., an amino acid) using an adapted version of the general procedure described above wherein hydrolyzed starch is added to the DMF mixture instead of the biodegradable microspheres comprising crosslinked hydrolyzed starch. The ligand-modified hydrolyzed starch can then be used, for example, as a component in a hemostatic composition, without any further crosslinking with epichlorohydrin. In other embodiments, the ligand-modified polysaccharide is then crosslinked to form a microsphere, as mentioned above. For example, ligand-modified hydrolyzed starch, in accordance with certain embodiments, is then emulsified and cross-linked with epichlorohydrin to form ligand-modified biodegradable microspheres.

In some embodiments, the general procedure described above to introduce amino acid groups to the starch is performed on a modified starch (e.g., a starch modified such that, upon functionalization, the reactive groups (e.g., amine groups of the amino acids) are spaced apart from the backbone of the starch by an increased number of bonds). For example, in some embodiments, hydroxyalkyl starch (e.g., hydroxyethyl starch) is modified with a ligand (e.g., an amino acid) using an adapted version of the general procedure described above, wherein the modified starch (e.g., hydroxyalkyl starch) is used instead of the hydrolyzed starch.

While certain techniques and chemistries for functionalizing the polysaccharides with reactive groups such as amine groups are described above (e.g., via the attachment of ligands comprising amino acids), other suitable techniques may be used. For example, in some embodiments, a polysaccharide (e.g., any of the starches described herein) can be functionalized via silanization (e.g., by reacting the polysaccharide with a silane or alkoxysilane comprising the reactive group, such as an aminoalkylsilane). One non-limiting example of a suitable reagent in some such cases is (3-aminopropyl)triethoxysilane (APTES). One of ordinary skill in the art, with the benefit of this disclosure, would know suitable conditions for functionalizing a polysaccharide with a silane such as APTES. Exemplary methods for performing silanization steps are described in Wang, W.; Bai, Q.; Liang, T.; Bai, H.; Liu, X. *Int Biol Macromol*, 2017, 102, 944-951, Koga, H.; Kitaoka, T.; Isogai, A. *J Mater. Chem.* 2011, 21, 9356-9361, Koga, H.; Kitaoka, T.; Isogai, A. *Molecules*. 2015, 20, 1495-1508, and El-Sayed, N. S.; El-Sakhawy, M.; Brun, N.; Hesemann, P. *Carbohydrate Polymers*, 2018, 199, 193-204, each of which is incorporated by reference herein in their entirety. In some embodiments, at least some of the reactive groups of the modified polysaccharide component are bound to the polysaccharide via a linking moiety comprising silicon. In certain cases, at least some of the reactive groups are bound to the polysaccharide via a linking moiety comprising —O—$SiR_2$—$(CH_2)_n$—, wherein R is hydroxy or alkoxy and n is an integer from 1 to 10. In some embodiments, at least some of the amine groups of the second modified polysaccharide component are bound to the polysaccharide via a linking moiety comprising silicon. In certain cases, at least some of the amine groups are bound to the polysaccharide via a linking moiety comprising —O—$SiR_2$—$(CH_2)_n$—, wherein R is hydroxy or alkoxy and n is an integer from 1 to 10. In some embodiments, at least some of the amine groups are bound to the polysaccharide via a linking moiety comprising —O—$Si(OEt)_2$-$(CH_2)_3$—. In some embodiments, at least some of the reactive groups (e.g., amine groups) are bound to the polysaccharide via a linking moiety comprising —O—$SiR_2$—$(CH_2)_n$—NR'—$(CH_2)_m$—, wherein R is hydroxy or alkoxy, R is alkyl or hydrogen, and n and m are independently integers from 1 to 10.

As another non-limiting example, in some embodiments, a polysaccharide (e.g., any of the starches described herein) can be functionalized with amine groups by first introducing a leaving group and then reacting the starch comprising the leaving group with one or more reagents to introduce the amine. One exemplary way to introduce a leaving group is to introduce a tosyl (p-toluenesulfonyl) leaving group (e.g., at the oxygen at the 2 position or the 6 position of the monosaccharide in the case of starch). A tosylate group can, in some cases, be introduced by adapting the methods disclosed in El-Sayed, N. S.; El-Sakhawy, M.; Brun, N.; Hesemann, P. *Carbohydrate Polymers*, 2018, 199, 193-204, which is incorporated by reference herein in its entirety. Another exemplary way to introduce a leaving group is to replace one or more of the hydroxy groups of the monosaccharide units with bromo groups. A bromo group can, in some cases, be introduced by adapting the methods disclosed in in Hasegawa, T., et al. *Carbohydr. Res.* 2006, 341, 35-40, which is incorporated by reference herein in its entirety.

Once the polysaccharide (e.g., starch) comprises a leaving group (e.g., a tosyl group, bromo group, etc.), any of a number of suitable follow up steps can be used to introduce an amine group. One non-limiting method is to use a "click" chemistry method. For example, in some embodiments, the polysaccharide comprising the leaving group is reacted with an azide (e.g., sodium azide) to form an azide-functionalized polysaccharide (via a substitution reaction that releases the leaving group). In some such embodiments, the azide-functionalized polysaccharide is reacted with a reagent comprising an amino group, such a group with an alkyne (e.g., propyne), an amine, and an organic linker connecting the alkyne and the amine. One exemplary such class of reagents are the propargyl-polyethylene glycol-amine reagents (where the polyethylene glycol can be any suitable length). Such azide and click chemistry methods can be used, in some cases, by adapting the methods disclosed in Elchinger, P; Faugeras, P; Boens, B; Brouillette, F; Montplaisir, D; Zerrouki, R; Lucas, R. *Polymers,* 2011, 3, 1607-1651, which is incorporated by reference herein in its entirety.

Another exemplary functionalization method involves introducing an azide group as described above, and then reducing the azide group (e.g., with $LiAlH_4$ in dioxane) to form an amine group. The azide group of the azide-functionalized polysaccharide can be reduced to an amine, in some cases, by adapting the methods disclosed in Gonera, A.; 2004, *Amino functional Starch Derivatives: Synthesis, Analysis, and Application*, Cuvillier Verlag, which is incorporated by reference herein in its entirety.

In some embodiments, once the polysaccharide (e.g., starch) comprises a leaving group (e.g., a tosyl group, bromo group, etc.), polysaccharide comprising the leaving group can be reacted with di-amino reagent in which one of the two amine groups is protected (e.g., via a tert-butoxycarbonyl group). The two amine groups can be linked, in some cases, by an organic linking group (e.g., polyethylene glycol). The protecting group (e.g., Boc group) can then be removed in a follow-up step (e.g., via treatment with trifluoroacetic acid).

Another non-limiting method for functionalizing a polysaccharide (e.g., starch) with amine groups is by reacting the polysaccharide with an alkylamine. For example, in some embodiments, the polysaccharide is reacted via a substitution reaction with an alkylamine comprising a leaving group, such as 3-chloropropylamine or 2-chloropropylamine. In some embodiments, the polysaccharide is reacted with an aziridine. Exemplary methods for performing such reactions are described in in Gonera, A.; 2004, *Amino functional Starch Derivatives: Synthesis, Analysis, and Application*, Cuvillier Verlag.

In some embodiments, the polysaccharide is functionalized with one or more electrophilic groups, as mentioned above. One non-limiting method for functionalizing a polysaccharide (e.g., starch) with an electrophilic group (e.g., an N-oxy-succinimidyl group, N-oxysulfosuccinimidyl) is by first modifying the polysaccharide, and then coupling the modified polysaccharide to the electrophilic group. As one non-limiting example, in some embodiments, a starch (e.g., hydrolyzed starch) is reacted with chloroacetic acid in sodium hydroxide to form carboxymethyl starch. Then, in some such embodiments, the carboxymethyl starch is coupled to an N-hydroxy-succinimide or N-hydroxysulfosuccinimide using carbodiimide coupling chemistry to create an ester linkage, such as with 1-ethyl-3-(3-dimethylaminopropyl)carbodiimide (EDC). One exemplary method for performing the chloroacetic acid reaction step of such a functionalization is described in Haroon, M., et al. *R. Soc. Chem.,* 2016, 6, 78264-78285, which is incorporated by reference herein in its entirety. As another non-limiting example, in some embodiments, a starch (e.g., hydrolyzed starch) is reacted with succinic anhydride in dimethylsulfoxide (DMSO) in the presence of base (e.g., dimethylaminopyridine) to form a succinated starch. Then, in some such embodiments, the succinated starch is coupled to N-hydroxysuccinimide or N-hydroxysulfosuccinimide using carbodiimide coupling chemistry to create an ester linkage, such as with 1-ethyl-3-(3-dimethylaminopropyl)carbodiimide (EDC).

In some such embodiments, the succinated starch is coupled to N-hydroxysuccinimide or N-hydroxysulfosuccinimide using carbodiimide coupling chemistry to create an ester linkage in an aqueous solvent (e.g., a solvent having water in an amount of greater than 50 vol %, at least 75 vol %, at least 90 vol %, at least 95 vol %, at least 98 vol %, at least 99 vol % or 100 vol %), such as with 1-ethyl-3-(3-dimethylaminopropyl)carbodiimide (EDC). In some such embodiments, the succinated starch is coupled to N-hydroxysuccinimide or N-hydroxysulfosuccinimide using carbodiimide coupling chemistry to create an ester linkage in an organic solvent (e.g., a solvent comprising an organic liquid (e.g., DMSO) in an amount of greater than 50 vol %, at least 75 vol %, at least 90 vol %, at least 95 vol %, at least 98 vol %, at least 99 vol % or 100 vol %), such as with N,N-diisopropylcarbodiimide (DIC) and/or N,N'-dicyclohexylcarbodiimide (DCC). It has been determined in the context of this disclosure that coupling a modified starch such as succinated starch to compounds such as to N-hydroxysuccinimide or N-hydroxysulfosuccinimide in organic solvents can, in some instances, result in products (e.g., dry powder products of functionalized starch) containing less residual water than otherwise identical products prepared by coupling in aqueous solvents. Less residual water can, in some embodiments, be advantageous when water in components of dry powdered mixtures is deleterious (e.g., by causing undesired crosslinking or hydrolysis of reactive electrophilic end groups during storage rather than upon application to a bleeding/wound site).

In some embodiments, an isolated modified polysaccharide comprising hydrolyzed, uncrosslinked starch functionalized with electrophilic groups is provided. Such a modified polysaccharide, in its isolated state, may be useful as a crosslinking agent, for example as a reactive precursor component (e.g., for forming hydrogels useful for hemostatic applications). The electrophilic groups may be capable of reacting with nucleophiles such as amine groups (e.g., amine groups of a functionalized polysaccharide, a multi-functionalized polymer such as PEG-diamine, a protein such as albumin, etc.). The hydrolyzed, uncrosslinked starch functionalized with electrophilic groups (e.g., functionalized maltodextrin) may be present in the isolated modified polysaccharide composition in an amount of greater than or equal to 50 wt. %, greater than or equal to 60 wt. %, greater than or equal to 75 wt. %, greater than or equal to 90 wt. %, greater than or equal to 95 wt. %, greater than or equal to 98 wt. %, greater than or equal to 99 wt. %, greater than or equal to 99.9 wt. %, or higher. Such an isolated composition may have undergone one or more purification steps known in the art to remove other component (e.g., unreacted starting materials, reaction byproducts, solvent, etc.), such as filtration, washing, distillation, precipitation, crystallization, etc. The hydrolyzed, uncrosslinked starch functionalized with electrophilic groups may comprise electrophilic groups in any of the amounts per monomer or macromer described below or have a percentage of hydroxy groups substituted as described below.

It has been observed herein that number density of functional groups (e.g., reactive electrophilic groups and/or nucleophilic groups) introduced to the functionalized polysaccharides herein can be adjusted based on reaction conditions (e.g., by adjusting reaction times, by adjusting reagent ratios, etc.). Without wishing to be bound by any particular theory, an ability to tune the degree of functionalization may provide a way to alter crosslinking behavior (e.g., crosslinking rate) and properties of the resulting hemostatic hydrogels (e.g., burst strength, elastic modulus, etc.).

According to certain embodiments, the first modified polysaccharide component comprises any of a variety of suitable electrophilic groups with leaving groups (e.g., N-oxysuccinimidyl) per macromer (e.g., poly-glucose macromer). For example, in certain embodiments, the first component may comprise greater than or equal to 0 electrophilic groups per macromer, greater than or equal to 1 electrophilic groups per macromer, greater than or equal to 2 electrophilic groups residues per macromer, greater than or equal to 3 electrophilic groups per macromer, greater than or equal to 5 electrophilic groups per macromer, greater than or equal to 10 electrophilic groups per macromer, greater than or equal to 15 electrophilic groups per macromer, greater than or equal to 25 electrophilic groups per macromer, greater than or equal to 50 electrophilic groups per macromer, greater than or equal to 75 electrophilic groups per macromer, greater than or equal to 100 electrophilic groups per macromer, greater than or equal to 150 electrophilic groups per macromer, greater than or equal to 200 electrophilic groups per macromer, greater than or equal to 300 electrophilic groups per macromer, greater than or equal to 400 electrophilic groups per macromer, greater than or equal to 500 electrophilic groups per macromer, or more. According to certain embodiments, the first component may comprise less than or equal to 1500 electrophilic groups per macromer, less than or equal to 1200 electrophilic groups per macromer, less than or equal to 1000 electrophilic groups per macromer, less than or equal to 800 electrophilic groups per macromer, less than or equal to 600 electrophilic groups per macromer, less than or equal to 500 electrophilic groups per macromer, less than or equal to 400 electrophilic groups per macromer, less than or equal to 300 electrophilic groups per macromer, less than or equal to 200 electrophilic groups per macromer, less than or equal to 100 electrophilic groups per macromer, less than or equal to 90 electrophilic groups per macromer, less than or equal to 75 electrophilic groups per macromer, less than or equal to 60 electrophilic groups per macromer, less than or equal to 50 electrophilic groups per macromer, less than or equal to 25 electrophilic groups per macromer, less than or equal to 15 electrophilic groups per macromer, less than or equal to 10 electrophilic groups per macromer, less than or equal to 5 electrophilic groups per macromer, less than or equal to 4 electrophilic groups per macromer, or less than or equal to 3 electrophilic groups per macromer. Combinations of the above recited ranges are also possible (e.g., the first component comprises greater than or equal to 1 electrophilic group per macromer and less than or equal to 1500 electrophilic groups per macromer).

According to certain embodiments, the first modified polysaccharide component comprises any of a variety of suitable electrophilic groups with leaving groups (e.g., N-oxy-succinimidyl) as expressed as a percentage of hydroxy groups of the polysaccharide that have been substituted. For example, in certain embodiments, the percentage of hydroxy groups of the polysaccharide of the first component substituted with electrophilic groups with leaving groups may be greater than or equal to 0%, greater than or equal to 1%, greater than or equal to 2%, greater than or equal to 5%, greater than or equal to 8%, greater than or equal to 10%, greater than or equal to 15%, greater than or equal to 20%, greater than or equal to 30%, greater than or equal to 40%, greater than or equal to 45%, greater than or equal to 50%, greater than or equal to 60%, greater than or equal to 75%, greater than or equal to 90%, or greater. In some embodiments, the percentage of hydroxy groups of the polysaccharide of the first component substituted with electrophilic groups with leaving groups is less than or equal to 100%, less than or equal to 99%, less than or equal to 95%, less than or equal to 90%, less than or equal to 75%, less than or equal to 60%, less than or equal to 50%, less than or equal to 45%, less than or equal to 40%, less than or equal to 35%, less than or equal to 30%, less than or equal to 25%, less than or equal to 20%, less than or equal to 15%, or less. Combinations of the above recited ranges are also possible (e.g., the percentage of hydroxy groups of the polysaccharide of the first component substituted with electrophilic groups with leaving groups is greater than or equal to 1% and less than or equal to 100%, greater than or equal to 5% and less than or equal to 60%, or greater than or equal to 15% and less than or equal to 45%).

According to certain embodiments, the first modified polysaccharide component comprises any of a variety of suitable electrophilic groups with leaving groups (e.g., N-oxysuccinimidyl) per monomer unit (e.g., anhydroglucose monomer). For example, in certain embodiments, the first component may comprise greater than or equal to 0 electrophilic groups per monomer, greater than or equal to 0.1 electrophilic groups per monomer, greater than or equal to 0.2 electrophilic groups residues per monomer, greater than or equal to 0.45 electrophilic groups residues per monomer, greater than or equal to 0.5 electrophilic groups per monomer, greater than or equal to 0.9 electrophilic groups residues per monomer, greater than or equal to 1.0 electrophilic groups per monomer, greater than or equal to 1.35 electrophilic groups residues per monomer, greater than or equal to 1.5 electrophilic groups per monomer, greater than or equal to 2.0 electrophilic groups per monomer, or greater. According to certain embodiments, the first component may comprise less than or equal to 3 electrophilic groups per monomer, less than or equal to 2.5 electrophilic groups per monomer, less than or equal to 2.0 electrophilic groups per monomer, less than or equal to 1.5 electrophilic groups per monomer, less than or equal to 1.35 electrophilic groups per monomer, less than or equal to 1.0 electrophilic groups per monomer, or less. Combinations of the above recited ranges are also possible (e.g., the first component comprises greater than or equal to 0.1 electrophilic groups per monomer and less than or equal to 3 electrophilic groups per monomer).

According to certain embodiments, the first modified polysaccharide component (e.g., as part of a first dry powder) comprises any of a variety of suitable electrophilic groups with leaving groups (e.g., N-oxysuccinimidyl) per microsphere (e.g., microsphere comprising crosslinked hydrolyzed starch). The number of electrophilic groups may depend on the method employed for functionalizing the polysaccharide chains of the microsphere. For example, in some embodiments, a microsphere comprising crosslinked polysaccharide chains (e.g., crosslinked hydrolyzed starch) may be first prepared and then functionalized by reacting the microsphere with functionalizing agents. In other embodiments, the polysaccharide chains may be functionalized with electrophilic groups prior to crosslinking to form the microspheres. Further, the number of electrophilic groups per microsphere will also generally scale with the size of the microsphere (e.g., as represented by the diameter of the microsphere). In some, but not necessarily all embodiments, the microspheres are derived from crosslinked functionalized polysaccharide chains comprising electrophilic groups in amounts within the ranges described above (on a per macromer and/or per monomer basis). In some such embodiments, the microspheres have diameters with the ranges described herein (e.g., from 1 µm to 1000 µm).

According to certain embodiments, the second modified polysaccharide component comprises (e.g., as part of a second dry powder) any of a variety of suitable amine groups (e.g., an amino acid ligand comprising an amine such as lysine, or an amine group linked via a silicon-containing moiety as described above) per macromer (e.g., poly-glucose macromer). For example, in certain embodiments, the second component may comprise greater than or equal to 0 amine groups per macromer, greater than or equal to 1 amine groups per macromer, greater than or equal to 2 amine groups residues per macromer, greater than or equal to 3 amine groups per macromer, greater than or equal to 5 amine groups per macromer, greater than or equal to 10 amine groups per macromer, greater than or equal to 15 amine groups per macromer, greater than or equal to 25 amine groups per macromer, greater than or equal to 50 amine groups per macromer, greater than or equal to 75 amine groups per macromer, greater than or equal to 100 amine groups per macromer, greater than or equal to 150 amine groups per macromer, greater than or equal to 200 amine groups per macromer, greater than or equal to 300 amine groups per macromer, greater than or equal to 400 amine groups per macromer, greater than or equal to 500 amine groups per macromer, or more. According to certain embodiments, the second component may comprise less than or equal to 1500 amine groups per macromer, less than or equal to 1200 amine groups per macromer, less than or equal to 1000 amine groups per macromer, less than or equal to 800 amine groups per macromer, less than or equal to 600 amine groups per macromer, less than or equal to 500 amine groups per macromer, less than or equal to 400 amine groups per macromer, less than or equal to 300 amine groups per macromer, less than or equal to 200 amine groups per macromer, less than or equal to 100 amine groups per macromer, less than or equal to 90 amine groups per macromer, less than or equal to 75 amine groups per macromer, less than or equal to 60 amine groups per macromer, less than or equal to 50 amine groups per macromer, less than or equal to 25 amine groups per macromer, less than or equal to 15 amine groups per macromer, less than or equal to 10 amine groups per macromer, less than or equal to 5 amine groups per macromer, less than or equal to 4 amine groups per macromer, or less than or equal to 3 amine groups per macromer. Combinations of the above recited ranges are also possible (e.g., the first component comprises greater than or equal to 1 amine groups per macromer and less than or equal to 1500 amine groups per macromer).

According to certain embodiments, the second modified polysaccharide component comprises any of a variety of suitable amine groups (e.g., an amino acid ligand comprising an amine such as lysine, or an amine group linked via a silicon-containing moiety as described above) as expressed as a percentage of hydroxy groups of the polysaccharide that have been substituted. For example, in certain embodiments, the percentage of hydroxy groups of the polysaccharide of the second component substituted with amine groups may be greater than or equal to 0%, greater than or equal to 1%, greater than or equal to 2%, greater than or equal to 5%, greater than or equal to 8%, greater than or equal to 10%, greater than or equal to 15%, greater than or equal to 20%, greater than or equal to 30%, greater than or equal to 40%, greater than or equal to 45%, greater than or equal to 50%, greater than or equal to 60%, greater than or equal to 75%, greater than or equal to 90%, or greater. In some embodiments, the percentage of hydroxy groups of the polysaccharide of the second component substituted with amine groups is less than or equal to 100%, less than or equal to 99%, less than or equal to 95%, less than or equal to 90%, less than or equal to 75%, less than or equal to 60%, less than or equal to 50%, less than or equal to 45%, less than or equal to 40%, less than or equal to 35%, less than or equal to 30%, less than or equal to 25%, less than or equal to 20%, less than or equal to 15%, or less. Combinations of the above recited ranges are also possible (e.g., the percentage of hydroxy groups of the polysaccharide of the second component substituted with amine groups is greater than or equal to 1% and less than or equal to 100%, greater than or equal to 5% and less than or equal to 60%, or greater than or equal to 15% and less than or equal to 45%).

According to certain embodiments, the first modified polysaccharide component comprises any of a variety of suitable amine groups (e.g., an amino acid ligand comprising an amine such as lysine, or an amine group linked via a silicon-containing moiety as described above) per monomer unit (e.g., anhydroglucose monomer). For example, in certain embodiments, the first component may comprise greater than or equal to 0 amine groups per monomer, greater than or equal to 0.1 amine groups per monomer, greater than or equal to 0.2 amine groups per monomer, greater than or equal to 0.45 amine groups per monomer, greater than or equal to 0.5 amine groups per monomer, greater than or equal to 0.9 amine groups per monomer, greater than or equal to 1.0 amine groups per monomer, greater than or equal to 1.35 amine groups per monomer, greater than or equal to 1.5 amine groups per monomer, greater than or equal to 2.0 amine groups per monomer, or greater. According to certain embodiments, the first component may comprise less than or equal to 3 amine groups per monomer, less than or equal to 2.5 amine groups per monomer, less than or equal to 2.0 amine groups per monomer, less than or equal to 1.5 amine groups per monomer, less than or equal to 1.35 amine groups per monomer, less than or equal to 1.0 amine groups per monomer, or less. Combinations of the above recited ranges are also possible (e.g., the first component comprises greater than or equal to 0.1 amine groups per monomer and less than or equal to 3 amine groups per monomer).

According to certain embodiments, the second modified polysaccharide component comprises any of a variety of suitable amine groups (e.g., an amino acid ligand comprising an amine such as lysine or an amine group linked via a silicon-containing moiety as described above) per microsphere (e.g., microsphere comprising crosslinked hydrolyzed starch). The number of amine groups may depend on the method employed for functionalizing the polysaccharide chains of the microsphere. For example, in some embodiments, a microsphere comprising crosslinked polysaccharide chains (e.g., crosslinked hydrolyzed starch) may be first prepared and then functionalized by reacting the microsphere with functionalizing agents. In other embodiments, the polysaccharide chains may be functionalized with amine groups prior to crosslinking to form the microspheres. Further, the number of amine groups per microsphere will also generally scale with the size of the microsphere (e.g., as represented by the diameter of the microsphere). In some, but not necessarily all embodiments, the microspheres are derived from crosslinked functionalized polysaccharide chains comprising amine groups in amounts within the ranges described above (on a per macromer and/or per monomer basis). In some such embodiments, the microspheres have diameters with the ranges described herein (e.g., from 1 µm to 1000 µm).

In some embodiments, the uncrosslinked polysaccharide chains and/or microspheres are modified with only nucleophilic groups (e.g., modified only with amines) or only with electrophilic groups (e.g., modified only with N-oxysuccinimidyl groups). In some embodiments, the uncrosslinked polysaccharide chains and/or microspheres are modified with at least one nucleophilic group and at least one electrophilic group.

According to some embodiments, a dry, powdered, hemostatic composition comprises a first component and a second component. In some aspects, the first component is in the form of a first powder (e.g., a first dry powder), and the second component is in the form of a second powder (e.g., a second dry powder). In certain embodiments, a two part crosslinking dry powder hemostatic formulation is provided. As mentioned above, in some embodiments, a first component of a dry powder hemostat (e.g., a first dry powder) comprises a multifunctionalized polymer. The multifunctionalized polymer may be a multifunctionalized polyalkylene oxide-based polymer (e.g., capable of reactive with a modified polysaccharide component). For example, in some embodiments, a first component (e.g., first dry powder) comprises a multifunctionalized polymeric composition of the formula:

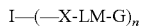

wherein:
X is a polyoxyethylene chain portion or a bond;
each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments;
each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl;
I is a multifunctional linking moiety derived from a multinucleophilic compound; and
n is an integer from 2 to 10;
with the proviso that when X is a difunctional polyoxyethylene chain portion and n=2, —X—I—X— is polyethylene glycol (PEG), which is a diradical fragment represented by the formula:

wherein a is an integer from 20 to 300.
In some embodiments, a first component (e.g., dry powder) comprises a multifunctionalized polymeric composition of the formula:

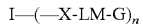

wherein:
X is a polyoxyethylene chain portion or a bond;
each LM is the same and is a difunctional linking moiety represented by the formulas —C(O)—, —(CH$_2$)$_b$—C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 1 to 10, d is an integer from 1 to 10, and R is a polymer or copolymer having 1 to 10 monomeric lactide, glycolide, trimethylene carbonate, caprolactone or p-dioxanone fragments;
each G is the same is a leaving group selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl;

I is a multifunctional linking moiety derived from a multinucleophilic compound; and n is an integer from 2 to 10;

with the proviso that when X is a difunctional polyoxyethylene chain portion and n=2, —X—I—X— is polyethylene glycol (PEG), which is a diradical fragment represented by the formula:

O—(CH$_2$—CH$_2$—O—)$_a$— wherein a is an integer from 20 to 300.

While in some embodiments, a multifunctionalized polymer of the formula I—(—X-LM-G)$_n$ as described above is a difunctionalized polymer such as PEGSS(2) (e.g., where X is a bond and n is 2 and I is a difunctional polyethylene glycol (PEG)), in some embodiments the first component comprises a multifunctionalized polymer with a higher (than two) degree of functionality (e.g., n is 3, 4, 5, 6, 7, or 8).

According to some embodiments, the first component (e.g., dry powder) comprises a multifunctionalized polymeric composition of the formula:

I—(—X-LM-G)$_n$ wherein:

when X is a bond, I is a multi-arm PEG in which the number of arms is n.

In certain embodiments, X in the formula I—(—X-LM-G)$_n$ is the difunctional polyethylene oxide polyethylene glycol (PEG), which is represented by the formula:

—O—(CH$_2$—CH$_2$—O—)$_a$— wherein:

a is an integer from 20 to 300.

In some embodiments, the first component (e.g., dry powder) comprises a multifunctionalized polymeric composition of the formula:

I-(LM-G)$_n$ wherein:

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, —N(H)—C(O)—(CH$_2$)$_d$—C(O)— where d is an integer from 1 to 10, —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments;

each G is a leaving group independently selected from the group of N-oxysuccinimidyl, N-oxysulfosuccinimidyl, N-oxymaleimidyl, N-oxyphthalimidyl, nitrophenoxyl, N-oxyimidazolyl, and tresyl;

I is a multifunctional polyoxyethylene chain portion having n functional groups able to react with a functional group of LM; and n is an integer from 2 to 10.

In some such embodiments, the multifunctionalized polymeric composition has a higher (than two) degree of functionalization, though in some embodiments the multifunctionalized polymeric composition is difunctionalized (e.g., n is 2). It should be understood than when it is stated that the multifunctionalized polyoxyethylene chain portion has n functional groups able to react with a functional group of LM, such characterization relates to the nature of the portions of the molecule in their unassembled/disassembled state for the purpose of explaining to the reader the nature of the subcomponents and their mutual reactivity. Of course, as would be apparent to those skilled in the art, with respect to the compositions described by the chemical formulas described herein, the reaction between the indicated functional group and LM is understood to have occurred in the polymer represented by the formula I-(LM-G)$_n$, (i.e., the formula describes the nature of the formed bonds based on the reactivity of their precursor components rather than the formula representing a set of reactants in an unreacted state). For example, in considering PEG-SS(2) as a species of I-(LM-G)$_n$, I is a polyethylene glycol chain portion and LM is succinate diradical. The polyethylene glycol has a functional group (an oxide oxygen) bound to a carbonyl carbon of the succinate diradical (—C(O)—(CH$_2$)$_2$—C(O)—). In this way, the polyethylene glycol chain portion has a functional group (an oxyl radical) able to react with a functional group (a carbonyl carbon radical) of the succinate diradical, as evidenced by the fact the two functional groups are bound in PEGSS(2).

According to some embodiments, the first component (e.g., dry powder) comprises a multifunctionalized polymeric composition of the formula:

I-(LM-G)$_n$ wherein:

each LM is the same and is a difunctional linking moiety represented by the formulas —C(O)—, —(CH$_2$)$_b$—C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments;

each G is the same and is a leaving group selected from the group of N-oxysuccinimidyl, N-oxysulfosuccinimidyl, N-oxymaleimidyl, N-oxyphthalimidyl, nitrophenoxyl, N-oxyimidazolyl and tresyl;

I is a multifunctional polyoxyethylene chain portion having n functional groups able to react with a functional group of LM; and n is an integer from 2 to 10.

In some embodiments, the first component (e.g., dry powder) comprises a multifunctionalized polymeric composition of the formula G-LM-PEG-LM-G wherein:

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 2 to 10, d is an integer from 2 to 10, and R is a polymer or copolymer having 1 to 10 monomeric lactide, glycolide, trimethylene carbonate, caprolactone or p-dioxanone fragments;

each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl.

In certain embodiments, the first component (e.g., first dry powder) comprises a multifunctionalized polymeric composition of the formula G-LM-PEG-LM-G wherein:

each LM is the same and is a difunctional linking moiety represented by the formulas —C(O)—, —(CH$_2$)$_b$—C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, and an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments; and each G is the same and is a leaving group selected from the group of N-oxysuccinimidyl, N-oxysulfosuccinimidyl, N-oxymaleimidyl, N-oxyphthalimidyl, nitrophenoxyl, N-oxyimidazolyl, and tresyl.

According to some embodiments, the first component (e.g., first dry powder) may comprise any of a variety of suitable multifunctionalized polymeric compositions. For example, in certain embodiments, the first component (e.g., first dry powder) may comprise:

PEG disuccinimidyl succinate (PEG(SS)2), a 2-arm crosslinker of the form:

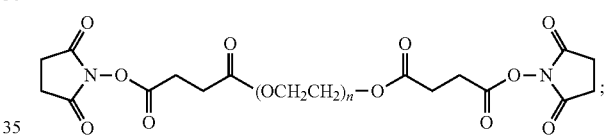

PEG disuccinimidyl hexanoate (PEG(SHA)2), a 2-arm crosslinker of the form:

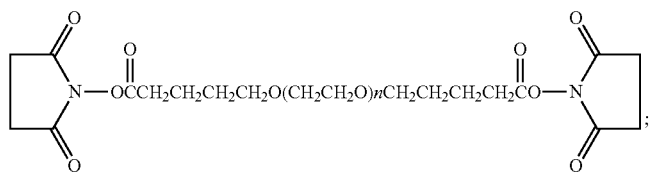

PEG disuccinimidyl valerate (PEG(SVA)2), a 2-arm crosslinker of the form:
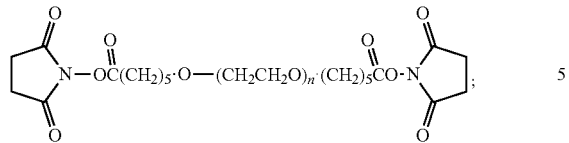
PEG tetrasuccinimidyl glutarate (PEG(SG)4), a 4 arm crosslinker of the form:
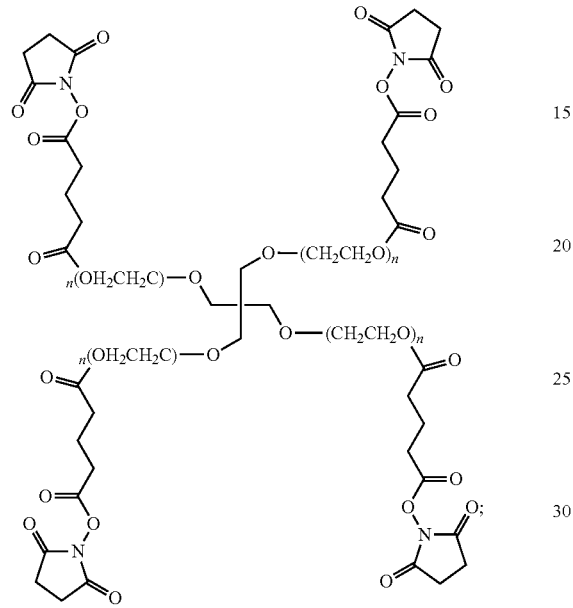
and/or
PEG tetrasuccinimidyl lactylglutarate (PEG(SG)4LA), a 4 arm crosslinker of the form:
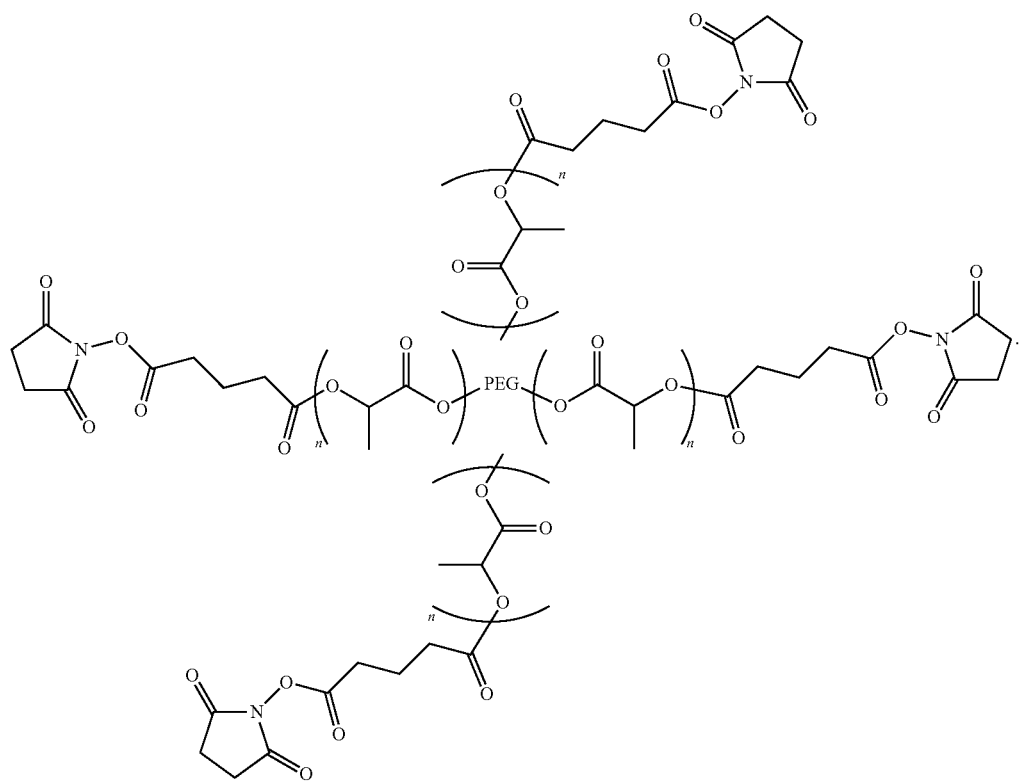

In some such embodiments, in any of the chemical structures above (e.g., PEG(SS)2, PEG(SVA)2, PEG(SHA)2, PEG(SG)4, PEG(SG)4LA), each n is independently an integer from 10 to 500. In some such embodiments, each n may independently be an integer from 50 to 200.

Other multifunctionalized polymeric compositions are also possible. For example, in some embodiments the first component (e.g., first dry powder) comprises a di- or higher order multifunctionalized PEG based on any of the following PEG NHS esters:

| PEG NHS Ester | Ester (Symbol) |
|---|---|
| PEG-CH$_2$CH$_2$CH$_2$CH$_2$—CO$_2$—NHS | Succinimidyl Valerate (SVA) |
| PEG-O—CO$_2$—NHS | Succinimidyl Carbonate (SC) |
| PEG-O$_2$C—CH$_2$CH$_2$CH$_2$—CO$_2$—NHS | Succinimidyl Glutarate (SG) |
| PEG-O$_2$C—CH$_2$CH$_2$—CO$_2$—NHS | Succinimidyl Succinate (SS) |
| PEG-O—CH$_2$—CO$_2$—NHS | Succinimidyl Carboxymethylated (SCM) |
| PEG-O—CH$_2$ CH$_2$ CH$_2$—CO$_2$—NHS | Succinimidyl Butanoate (SBA) |
| PEG-NHCO—CH$_2$ CH$_2$—CO$_2$—NHS | Succinimidyl Succinamide (SSA) |
| PEG-O—CH$_2$ CH$_2$—CO$_2$—NHS | Succinimidyl Propionate (SPA) |
| PEG2- O$_2$CHN—CH(R)$^a$—CO$_2$— NHS | mPEG2-NHS |

In certain embodiments, the first component (e.g., first dry powder) comprises a combination of multifunctionalized polymeric compositions. For example, in certain embodiments, the first component may comprise any suitable combination of a difunctionalized polymeric composition, a trifunctionalized polymeric composition, a tetrafunctionalized polymeric composition, a pentafunctionalized polymeric composition, a hexafunctionalized polymeric composition, a heptafunctionalized polymeric composition, and/or an octafunctionalized polymeric composition. In some non-limiting embodiments, the first component comprises a difunctionalized polymeric composition and a tetrafunctionalized polymeric composition.

According to certain embodiments with a first component (e.g., a first dry powder) comprising a multifunctionalized polymeric composition of the formula I—(—X-LM-G)$_n$, the polymeric composition may have any of a variety of suitable weight average molecular weights. For example, in certain embodiments, the first component (e.g., first dry powder) may have a weight average molecular weight of greater than or equal to 1 kDa, greater than or equal to 5 kDa, greater than or equal to 10 kDa, greater than or equal to 15 kDa, greater than or equal to 20 kDa, or greater than or equal to 25 kDa. In certain embodiments, the polymeric composition may be a macromer having a weight average molecular weight of less than or equal to 30 kDa, less than or equal to 25 kDa, less than or equal to 20 kDa, less than or equal to 15 kDa, less than or equal to 10 kDa, or less than or equal to 5 kDa. Combinations of the above recited ranges are also possible (e.g., the formulation may include a mixture of polymeric compositions or macromers that have a weight average molecular weight of greater than or equal to 1 kDa and less than or equal to 30 kDa, or greater than or equal to 10 kDa and less than or equal to 15 kDa, and the like). In some embodiments, the weight average molecular weight of the first component (e.g., a first dry powder) comprising a multifunctionalized polymeric composition of the formula I—(—X-LM-G)$_n$ is determined using size exclusion chromatography-multi-angle laser light scattering (SEC-MALLS). It should be understood that the weight average molecular weight can depend on, for example, the number of monomers in each polymeric component of a multifunctionalized polymeric composition. For example, in some embodiments, when the multifunctionalized polymeric composition is PEG(SS)2, the degree of ethoxylation in the PEG (and the value for n in the formula shown for PEG(SS)2 above) is such that the multifunctionalized polymeric composition has a weight average molecular weight in any of the ranges provided above. In certain embodiments, for the chemical structure of the 2-arm PEG disuccinimidyl succinate (PEG(SS)2 shown above, n is in the range of 10 to 500, or 50 to 200.

According to certain embodiments, multifunctionalized polymeric compositions describable by the formula I—(—X-LM-G)$_n$, such as but not limited to the examples noted above, may be prepared by any of a variety suitable synthetic methods known to those skilled in the art. For example, see, U.S. Pat. No. 6,576,263 issued on Jun. 10, 2003 to Truong et al.; U.S. Reissued Pat. No. RE38,827 issued on Oct. 11, 2005 to Barrows et al.; and U.S. Reissued Pat. No. RE38,158 issued on Jun. 24, 2003 to Barrows et al.; which are incorporated herein by reference in its entirety for all purposes.

For example, the multifunctionalized polymeric compositions describable by the formula I—(—X-LM-G)$_n$ may be prepared using known processes, procedures or synthetic methods such as the procedures reported in U.S. Pat. No. 4,101,380, issued on Jul. 18, 1978 to Rubinstein or U.S. Pat. No. 4,839,345, issued on Jun. 13, 1989 to Doi et al., the procedure reported in International Application Publication No. WO/1990/013540 by Zalipsky, published on Nov. 15, 1990 from International Application No. PCT/US90/02133 filed Apr. 19, 1990 or the procedure reported by Abuchowski et al., Cancer Biochem. Biophys., 7:175-186 (1984), which are each incorporated herein by reference. Briefly, a polyalkylene oxide-based component (e.g., polyethylene glycol discussed below as exemplary) and a suitable acid anhydride are dissolved in a suitable polar organic solvent in the presence of base and refluxed for a period of time sufficient to form a polyethylene glycol diester diacid. The diester diacid is then reacted with a leaving group such as an N-hydroxy imide compound in a suitable polar organic solvent in the presence of dicyclohexylcarbodiimide or other condensing agents and stirred at room temperature to form the desired bifunctional crosslinking agent.

All or some of the multifunctionalized polymeric compositions describable by the formula I—(—X-LM-G)$_n$ may be purchased from commercial sources, including, but not limited to, NOF America Corporation and/or Laysan Bio, Inc. The multifunctionalized polymeric compositions may also be readily synthetized by persons of ordinary skill in the chemical synthesis art in view the teaching and exemplary methods described herein for exemplary compositions, published literature, and the level of ordinary skill and knowledge of the skilled artisan.

In certain non-limiting embodiments, PEG(SS)2 can be synthesized by obtaining a linear PEG with an average weight average molecular weight of 3,350 Da, representing 75.7 oxyethylene repeat units. The linear PEG can be obtained, for example, from Dow Chemical Company. The linear PEG may be converted to PEG(SS)2 via a two-step synthesis, in some cases. For instance, the first step may comprise reacting the linear PEG with succinic anhydride to produce PEG(disuccinate), or PEG(SS). The second step may comprise reacting PEG(SS) with N-hydroxysuccinimide to produce PEG(SS)2, resulting in a white solid and a two arm crosslinker that possess two succinimidyl groups per molecule.

Alternatively, in another non-limiting embodiment, PEG (SG)4 is derived from a PEG with a weight average molecular weight of, between 2,000 Da and 10,000 Da, or greater, and utilizes glutaric acid anhydride in place of succinic anhydride to produce the intermediate, followed by the same N-hydroxysuccinimide reaction in the subsequent step. Instead of two reactive end groups, PEG(SG)4 possesses four reactive end groups. The first step is the addition of the anhydride (e.g., glutaric anhydride) to the linear PEG 10,000 to incorporate the carboxyl end groups. The product is then reacted with N-hydroxysuccinimide reagent in the second step to add the succinimidyl reactive end groups.

In yet another non-limiting embodiment, PEG(SG)4LA is similar to PEG(SG4) but possesses an additional step to incorporate lactic acid groups. The purpose of incorporating lactide groups, in certain embodiments, is to provide a hydrolytically susceptible linkage in the final product thereby facilitating faster resorption. In some embodiments, the lactide groups are added prior to the glutaric anhydride step utilizing cyclic lactide. Because lactide is a dimer of lactic acid, the number of lactic acid groups in the chain will be an even number and will be a distribution of molecular weights. Since the molecular weight of PEG(SG)4LA is stated to be 11,500 Da, in certain embodiments, there are roughly 2.5 lactide groups/arm or 10 lactide groups/molecule (e.g., 4 arms). The first synthetic step is the addition of the lactide groups to each end of the PEG. The second synthetic step is the addition of glutaric anhydride, followed by the addition of N-hydroxysuccinimide.

In certain embodiments, multifunctionalized polymeric composition of the formula I—(—X-LM-G)$_n$ comprise a leaving group G (e.g., N-oxysuccinimidyl, N-oxymaleimidyl, N oxyphthalimidyl, nitrophenoxyl, N-oxyimidazolyl, and tresyl) capable of reacting with (e.g., being displaced by) a nucleophilic group, for example an amine group on another natural or synthetic polymer, e.g., a protein. For example, when G is N-oxysuccinimidyl, G-LM-PEG-LM-G comprises an NHS ester electrophilic group comprising an N-oxy-succinimidyl leaving group. According to certain embodiments, the leaving group G reacts with an amine group of the protein to produce a crosslinked composition that forms an amide bond upon release of the leaving group G. Referring back to the example above, the N-oxy-succinimidyl leaving group of the G-LM-PEG-LM-G comprising the NHS ester electrophilic group reacts with an amine group of the protein (or of a modified polysaccharide) resulting in a crosslinked composition having an amide bond upon release of the N-oxy-succinimide. Such reactivity is further described in U.S. Pat. No. 6,458,147, issued on Oct. 1, 2002 to Cruise et al., which is incorporated herein by reference in its entirety.

In some cases, a hemostatic composition (e.g., a dry, powdered hemostatic composition) includes a first component and a second component. In certain cases, the first component comprises a multifunctionalized polymer comprising electrophilic groups comprising leaving groups selected from the same group as G described above (e.g., N-oxysuccinimidyl, N-oxysulfosuccinimidyl, N-oxymaleimidyl, N-oxyphthalimidyl, nitrophenoxyl, N-oxyimidazolyl, and tresyl), and the second component comprises a modified polysaccharide component comprising a plurality of polysaccharide chains functionalized with amine groups. The first component and the second component may crosslink (e.g., upon exposure to water) to form a hemostatic hydrogel. The multifunctionalized polymer may be a multifunctionalized polyalkylene oxide-based polymer, including any of the multifunctionalized polyalkylene oxides described above. In certain cases, the multifunctionalized polymer is a multifunctionalized polyethylene glycol, such as any of those described above (e.g., PEG(SS)2, PEG(SG) 4, tetrasuccinimidyl lactylglutarate). In certain embodiments, the multifunctionalized polymer is PEG(SS)2. In some cases, the modified polysaccharide component comprises hydrolyzed, uncrosslinked starch functionalized with amine groups. In certain instances, the modified polysaccharide comprises a plurality of dry, porous microspheres formed of crosslinked starch, such as modified microporous microspheres comprising hydrolyzed starch crosslinked with glycerol ether or polyglycerol ether linkages, such as 1,3,-oxy-propan-2-ol linkages. In some embodiments, the modified polysaccharide component comprises a starch functionalized with amine groups, where the amine groups are spaced apart (e.g., at least two bonds, at least three bonds, at least four bonds removed) from the backbone of the starch, such as a hydroxyalkyl starch. In some cases, the amine groups of the modified polysaccharide are part of any of the nucleophilic amino acids described above. In some cases, the amine groups of the modified polysaccharide are bound to the polysaccharide via a linking moiety that comprises silicon, such as any of those described above. Formation of hemostatic hydrogel comprising a polymer (e.g., a multifunctionalized polyalkylene oxide) crosslinked with a polysaccharide (e.g., functionalized hydrolyzed, uncrosslinked starch, functionalized porous starch microspheres, and/or functionalized hydroxyalkyl starches) can, in some cases, lead to the realization of certain advantages. For example, a hemostatic hydrogel comprising a polyalkylene oxide-based polymer (e.g., multifunctionalized PEG) crosslinked with a functionalized polysaccharide can, in some cases, have a relatively high burst strength while also being relatively biodegradable. Additionally, a hemostatic hydrogel comprising a multifunctionalized polymer such as a multifunctionalized polyalkylene oxide (e.g., PEG(SS)2) crosslinked with a functionalized polysaccharide (e.g., a polysaccharide functionalized with amine groups) can, in some cases, be free of any animal or human-derived components. As such, in some cases, such a hemostatic hydrogel lacking animal or human-derived components may pose a reduced risk (or even no risk) of viral transmission. In contrast, hemostatic hydrogels comprising, for example, a multifunctionalized polymer crosslinked with albumin contain animal or human-derived components, and therefore can, in some cases, pose at least some potential risk of viral transmission during hemostatic applications. Another advantage associated with certain embodiments involving hemostatic hydrogels comprising multifunctionalized polymers (e.g., PEG(SS)2) crosslinked with a functionalized polysaccharide is a potential for faster resorption time relative to hemostatic hydrogels comprising, for example, certain multifunctionalized polymers crosslinked with proteins such as albumin. A faster resorption time may, in some cases, be due to enzymatic activity (e.g., enzymatic amylase activity) that can occur when the hemostatic hydrogel is in contact with the body of a patient. A faster resorption time can, in certain cases, reduce the risk of infection and reduce inflammatory responses during hemostatic applications.

One exemplary embodiment includes a hemostatic composition where the first component (optionally in the form of a first powder) comprises a multifunctionalized polyalkylene oxide-based polymer comprising electrophilic groups comprising leaving groups selected from the same group as G described above, and the second component (optionally in the form of a second powder) comprises hydrolyzed, uncrosslinked starch that is functionalized with amine groups. Upon exposure to water (and optionally in the presence of an initiator), the amine groups of the hydrolyzed, uncrosslinked starch may react with the electrophilic groups of the polyalkylene oxide-based polymer such that a crosslinked hemostatic hydrogel is formed (e.g., at a bleeding/wound site). As a specific, non-limiting example, in certain cases, a dry, powdered hemostatic composition comprises a first component comprising PEG(SS)2 and a second component comprising hydrolyzed, uncrosslinked starch functionalized with an amino acid selected from the group consisting of lysine, glycine, arginine, and alanine. In certain embodiments, the amino acid is glycine or lysine. The amino acid of the functionalized hydrolyzed, uncrosslinked starch may react with the electrophilic groups of the PEG(SS)2 (e.g., upon exposure to water and optionally in the presence of an initiator), thereby forming a hemostatic hydrogel.

As another example, in some embodiments, uncrosslinked polysaccharide chains and/or microspheres modified with nucleophilic groups (e.g., modified with amines) are used in combination with the functionalized polyalkylene oxide-based component described above (e.g., PEG(SS)2). For example, in some certain embodiments, a dry powdered composition for use in hemostasis comprises a first dry powder component comprising PEG(SS)2 and a second dry powder component comprising dry, porous microspheres of crosslinked starch functionalized with amine groups. In certain embodiments, the first and second dry component, when exposed to water and/or an initiator, can crosslink to form a hemostatic hydrogel. The use of PEG(SS)2 in such an embodiment is exemplary, and other multifunctionalized polymers such as multifunctionalized polyalkylene oxide-based polymers described can crosslink with dry, porous microspheres of crosslinked starch comprising amine groups to form a hemostatic hydrogel (e.g., upon exposure to water and/or an initiator).

Another exemplary embodiment includes a hemostatic composition where the first component (optionally in the form of a first powder) comprises a multifunctionalized polyalkylene oxide-based polymer comprising electrophilic groups comprising leaving groups selected from the same group as G described above, and the second component (optionally in the form of a second powder) comprises a starch functionalized with the amine groups, and the amine groups are at least two bonds, at least three bonds, at least four bonds, or more removed from the backbone of the starch. In some embodiments, the second polysaccharide component comprises a hydroxyalkyl starch (e.g., hydroxyethyl starch) functionalized with the amine groups. Upon exposure to water (and optionally in the presence of an initiator), the amine groups of functionalized starch (e.g., hydroxyalkyl starch) may react with the electrophilic groups of the polyalkylene oxide-based polymer such that a crosslinked hemostatic hydrogel is formed (e.g., at a bleeding/wound site). As a specific, non-limiting example, in certain cases, a dry, powdered hemostatic composition comprises a first component comprising PEG(SS)2 and a second component comprising a starch functionalized with amine groups that are at least four bonds removed from the backbone of the starch (e.g., a functionalized hydroxyalkyl starch such as hydroxyethyl starch), where the amine groups are bound to the starch via a linking moiety that comprises silicon (e.g., as a result of APTES coupling). The amine group of the functionalized starch (e.g., hydroxyalkyl starch) may react with the electrophilic groups of the PEG(SS)2 (e.g., upon exposure to water and optionally in the presence of an initiator), thereby forming a hemostatic hydrogel.

In some cases, in which the hemostatic composition (e.g., a dry, powdered hemostatic composition) includes a first component and a second component, the first component comprises a modified polysaccharide component comprising a plurality of polysaccharide chains functionalized with electrophilic groups capable of reacting with amine groups, and the second component comprises a protein. The first component and the second component may crosslink (e.g., upon exposure to water) to form a hemostatic hydrogel. In some cases, the modified polysaccharide comprises hydrolyzed, uncrosslinked starch functionalized with electrophilic groups capable of reacting with amines (e.g., amines from the protein). In some embodiments, the electrophilic groups of the modified polysaccharide comprise ligands comprising leaving groups selected from the same group as G described above (e.g., N-oxysuccinimidyl, N-oxysulfosuccinimidyl, N-oxymaleimidyl, N-oxyphthalimidyl, nitrophenoxyl, N-oxyimidazolyl, and tresyl). In certain instances, the modified polysaccharide comprises a plurality of dry, porous microspheres, such as modified microporous microspheres comprising hydrolyzed starch crosslinked with glycerol ether or polyglycerol ether linkages, such as 1,3,-oxy-propan-2-ol linkages. In some embodiments, the modified polysaccharide component comprises a starch functionalized with electrophilic groups, where the electrophilic groups are spaced apart from (e.g., at least two bonds, at least three bonds, at least four bonds removed) from the backbone of the starch, such as a hydroxyalkyl starch.

In certain cases, the protein of the second component comprises any of a variety of suitable albumins. For example, in some embodiments, the protein comprises serum albumin. The serum albumin may be, in some cases, human serum albumin (HSA) derived from donor blood, recombinant human albumin (rHA) derived from yeast, and/or animal sourced albumin, e.g., bovine serum albumin (BSA), may be used. In certain non-limiting embodiments, for example, the protein may be Cohn analog culture grade BSA obtained from Proliant Biologicals. In some aspects, the recombinant human albumin may be Cellastim™ recombinant human albumin, Healthgen™ recombinant human albumin, or Optibumin™ recombinant human albumin.

According to some embodiments, the nucleophilic polymer or protein may comprise any of a variety of nucleophiles with reactive primary amines. For example, in some embodiments, the second component comprises collagen, gelatin and/or synthetic or natural polymers modified with amines. Other nucleophilic materials may also be possible.

Formation of hemostatic hydrogel comprising a polysaccharide (e.g., functionalized hydrolyzed starch such as functionalized maltodextrin, functionalized porous starch microspheres, and/or functionalized hydroxyalkyl starch) crosslinked with a protein (e.g., albumin) can, in some cases, lead to the realization of certain advantages. For example, a hemostatic hydrogel comprising a modified polysaccharide (e.g., functionalized hydrolyzed starch such as functionalized maltodextrin, starch microspheres, and/or hydroxyalkyl starch) crosslinked with a protein can, in some cases, have a relatively high biocompatibility. Additionally, a hemostatic hydrogel comprising a functionalized polysaccharide crosslinked with a protein (e.g., albumin) may, in some cases, have enhanced stability over hemostatic hydrogels comprising, for example, a multifunctionalized polyalkylene oxide (e.g., PEG(SS)2) crosslinked with albumin. As one specific example, the functionalized polysaccharides described herein may be less temperature-sensitive than multifunctionalized polymers such as multifunctionalized polyalkylene oxides. Moreover, functionalized polysaccharides (e.g., functionalized hydrolyzed starch such as functionalized maltodextrin, porous starch microspheres, or hydroxyalkyl starch) may be able to include a higher number or density of functional groups (e.g., electrophilic groups) than for certain multifunctionalized polymers such as PEG(SS)2. The presence of a relatively high number or density of electrophilic groups may result in hemostatic hydrogels with a relatively high density of crosslinks. Having a relatively high density of crosslinks can, in some cases, contribute to higher stability for the hydrogel. Another advantage associated with certain embodiments involving hemostatic hydrogels comprising functionalized polysaccharides crosslinked with a protein (e.g., albumin) is the potential for a faster resorption time. A faster resorption time may, in some cases, be due to enzymatic activity (e.g., enzymatic amylase activity) that can occur when the hemostatic hydrogel is in contact with the body of a patient. A faster resorption time can, in certain cases, reduce the risk of infection and reduce inflammatory responses during hemostatic applications.

One exemplary embodiment includes a hemostatic composition where the first component (optionally in the form of a first dry powder) comprises hydrolyzed, uncrosslinked starch (e.g., maltodextrin) that is functionalized with electrophilic groups comprising ligands comprising leaving groups selected from the same group as G above, and the second component (optionally in the form of a second dry powder) comprises a protein. Upon exposure to water (and optionally in the presence of an initiator), the electrophilic groups of the hydrolyzed, uncrosslinked starch may react with the nucleophilic groups of the protein (e.g., nucleophilic amino acid residues) such that a cross-linked hemostatic hydrogel is formed (e.g., at a bleeding/wound site). As a specific example, in certain cases, a dry, powdered hemostatic composition comprises a first component comprising hydrolyzed, uncrosslinked starch functionalized with a ligand comprising an leaving group selected from group G above and a second component comprising albumin. In certain embodiments, the leaving group is N oxysuccinimidyl. The electrophilic group (e.g., comprising N-oxysuccinimidyl, comprising N-oxysulfosuccinimidyl) of the functionalized hydrolyzed, uncrosslinked starch may react with nucleophilic amino acids of the albumin (e.g., upon exposure to water and optionally in the presence of an initiator), thereby forming a hemostatic hydrogel.

As another example, in some embodiments, uncrosslinked polysaccharide chains and/or microspheres modified with electrophilic groups are used in combination with a protein component (e.g., albumin). For example, in some certain embodiments, a dry powdered composition for use in hemostasis comprises a first component (e.g., first dry powder component) comprising dry, porous microspheres of crosslinked starch functionalized with N-oxysuccinimidyl groups and a second component (e.g., second dry powder component) comprising albumin. In certain embodiments, the first and second dry component, when exposed to water and/or an initiator, can crosslink to form a hemostatic hydrogel.

Another exemplary embodiment includes a hemostatic composition where the first component (optionally in the form of a first dry powder) comprises a starch functionalized with the electrophilic groups (the electrophilic groups being at least two bonds, at least three bonds, at least four bonds, or more removed from the backbone of the starch), and the second component (optionally in the form of a second dry powder) comprises a protein. In some embodiments, the first polysaccharide component comprises a hydroxyalkyl starch (e.g., hydroxyethyl starch) functionalized with the electrophilic groups. In some such embodiments, the electrophilic groups comprise ligands comprising leaving groups selected from the same group as G above. Upon exposure to water (and optionally in the presence of an initiator), the electrophilic groups of the functionalized starch (e.g., hydroxyalkyl starch) may react with the nucleophilic groups of the protein (e.g., nucleophilic amino acid residues) such that a cross-linked hemostatic hydrogel is formed (e.g., at a bleeding/wound site). As a specific example, in certain cases, a dry, powdered hemostatic composition comprises a first component comprising a first component comprising a starch (e.g., hydroxyalkyl starch such as hydroxyethyl starch) functionalized with leaving groups selected from group G above (where the leaving groups are at least four bonds removed from the backbone of the starch), and a second component comprising albumin. In some such embodiments, the leaving groups are bound to the starch via a linking moiety that comprises silicon (e.g., as a result of a coupling involving a silane reagent). In some embodiments, the leaving groups are bound to the starch via a linking moiety that comprises a diester linkage (e.g., a succinate linker, a glutarate linker). In certain embodiments, the leaving group is N-oxysuccinimidyl. In certain embodiments, the leaving group is N-oxysulfosuccinimidyl. The electrophilic group (e.g., comprising N-oxysuccinimidyl) of the functionalized starch (e.g., hydroxyalkyl starch) may react with nucleophilic amino acids of the albumin (e.g., upon exposure to water and optionally in the presence of an initiator), thereby forming a hemostatic hydrogel.

In some embodiments, in which the hemostatic composition (e.g., a dry, powdered hemostatic composition) includes a first component and a second component, the first component comprises a modified polysaccharide component comprising a plurality of polysaccharide chains functionalized with electrophilic groups capable of reacting with amine groups, and the second component comprises a multifunctionalized polyalkylene oxide-based polymer comprising amine groups (or corresponding salts thereof). A corresponding salt of a polyalkylene-oxide-based polymer comprising an amine group refers to a salt comprising the polymer with a protonated amine and a suitable counter-anion. For example, in some embodiments, a corresponding salt of a multifunctionalized polyalkylene oxide-based polymer comprising amine groups is an HCl salt of the polymer, where the chloride ion is the counter-anion. The first component and the second component may crosslink (e.g., upon exposure to water) to form a hemostatic hydrogel. In some cases, the modified polysaccharide comprises hydrolyzed, uncrosslinked starch functionalized with electrophilic groups capable of reacting with amines (e.g., amines from the multifunctionalized polyalkylene oxide-based polymer). In some embodiments, the electrophilic groups of the modified polysaccharide comprise ligands comprising leaving groups selected from the same group as G described above (e.g., N oxysuccinimidyl, N-oxysulfosuccinimidyl, N-oxymaleimidyl, N-oxyphthalimidyl, nitrophenoxyl, N-oxyimidazolyl, and tresyl). In certain instances, the modified polysaccharide comprises a plurality of dry, porous microspheres, such as modified microporous microspheres comprising hydrolyzed starch crosslinked with glycerol ether or polyglycerol ether linkages, such as 1,3,-oxy-propan-2-ol linkages. In some embodiments, the modified polysaccharide component comprises a starch functionalized with electrophilic groups, where the electrophilic groups are spaced apart from (e.g., at least two bonds, at least three bonds, at least four bonds removed) from the backbone of the starch, such as a hydroxyalkyl starch.

A multifunctionalized polyalkylene oxide-based polymer comprising amine groups can have any of a variety of suitable structures. In some embodiments, a multifunctionalized polyalkylene oxide-based polymer comprises two terminal amine groups. Some such polymers have the following structure:

$$R_2N-(CH_2)_n-(O(CH_2)_n)_m-NR_2$$

where each R can independently be hydrogen or branched or unbranched $C_1$-$C_4$ alkyl, n is an integer from 1 to 6, and m is an integer from 1 to 200. As a point of illustration, one non-limiting example of a corresponding salt of the above structure is the following HCl salt:

$$[HR_2N-(CH_2)_n-(O(CH_2)_n)_m-NR_2H]Cl_2$$

In some embodiments, the multifunctionalized polyalkylene oxide-based polymer is a polyethylene glycol diamine (PEG-diamine) having the following structure:

$$H_2N-(CH_2)_2-(O(CH_2)_2)_m-NR_2$$

where m is an integer from 1 to 200 (e.g., an integer from 10 to 100, 20 to 50, etc.). Suitable multifunctionalized polyalkylene oxide-based polymers comprising diamine groups (or corresponding salts thereof) can be obtained commercially, for example from Sigma Aldrich (St. Louis, Mo.), JenKem Technology USA Inc. (Plano, Tex.), and Alfa Aesar (Haverill, Mass.).

In some embodiments, a multifunctionalized polyalkylene oxide-based polymer comprising amine groups (or a corresponding salt thereof) is a multi-arm polymer, analogous to the multi-arm polyalkylene oxide polymers comprising electrophilic groups described above. For example, the structure of a multi-arm polymer comprising amine groups may correspond to the structure of any of those falling within the scope of I—(—X-LM-G)$_n$ above, except replacing the LM-G groups with any suitable linking moiety bound to a primary or secondary amine. For example, LM-G in the formula above could be replaced with a substituted or unsubstituted ether, alkyl, or aryl linking group terminating with a primary or second amine. In some embodiments, a multifunctionalized polyalkylene oxide-based polymer comprising amine groups is a 3-arm polymer (e.g., comprising 3 amines), a 4-arm polymer (e.g., comprising 4 amines), a 5-arm polymer (e.g., comprising 5 amines), a 6-arm polymer (e.g., comprising 6 amines), a 7-arm polymer (e.g., comprising 7 amines), an 8-arm polymer (e.g., comprising 8 amines), or a 10-arm polymer (e.g., comprising 10 amines). In some embodiments, a second component (e.g., second dry powder) comprises a mixture of different multifunctionalized polyalkylene oxide polymers comprising amine groups (e.g, a mixture of 2-arm PEG-diamine and a 4-arm PEG comprising 4 amine groups).

Formation of hemostatic hydrogel comprising a polysaccharide (e.g., functionalized hydrolyzed starch such as functionalized maltodextrin, functionalized porous starch microspheres, and/or functionalized hydroxyalkyl starch) crosslinked with a multifunctionalized polyalkylene oxide-based polymer comprising amine groups (e.g., PEG-diamine) or a corresponding salt thereof can, in some cases, lead to the realization of certain advantages. For example, a hemostatic hydrogel comprising a modified polysaccharide (e.g., functionalized hydrolyzed starch such as functionalized maltodextrin, starch microspheres, and/or hydroxyalkyl starch) crosslinked with a multifunctionalized polyalkylene oxide-based polymer comprising amine groups can, in some cases, be free of any animal or human-derived components. As such, in some cases, such a hemostatic hydrogel lacking animal or human-derived components may pose a reduced risk (or even no risk) of viral transmission. In contrast, hemostatic hydrogels comprising, for example, a multifunctionalized polymer crosslinked with albumin contain animal or human-derived components, and therefore can, in some cases, pose at least some potential risk of viral transmission during hemostatic applications. Another advantage associated with certain embodiments involving hemostatic hydrogels comprising multifunctionalized polyalkylene-based polymers comprising amine groups (e.g., PEG-diamine) crosslinked with a functionalized polysaccharide (e.g., functionalized hydrolyzed starch such as functionalized maltodextrin, starch microspheres, and/or hydroxyalkyl starch) is a potential for faster resorption time relative to hemostatic hydrogels comprising, for example, certain multifunctionalized polymers crosslinked with proteins such as albumin. A faster resorption time may, in some cases, be due to enzymatic activity (e.g., enzymatic amylase activity) that can occur when the hemostatic hydrogel is in contact with the body of a patient. A faster resorption time can, in certain cases, reduce the risk of infection and reduce inflammatory responses during hemostatic applications. Additionally, use of polyalkylene oxides having relatively high molecular weights (e.g., weight average molecular weight of greater than or equal to 5 kDa, greater than or equal to 10 kDa, greater than or equal to 20 kDa, or greater) may contribute to improved gel strength of the resulting hydrogel.

One exemplary embodiment includes a hemostatic composition where the first component (optionally in the form of a first dry powder) comprises hydrolyzed, uncrosslinked starch (e.g., maltodextrin) that is functionalized with electrophilic groups comprising ligands comprising leaving groups selected from the same group as G above, and the second component (optionally in the form of a second dry powder) comprises a multifunctionalized polyalkylene oxide-based polymer comprising amine groups (or corresponding salts thereof). Upon exposure to water (and optionally in the presence of an initiator), the electrophilic groups of the hydrolyzed, uncrosslinked starch may react with the amines of the multifunctionalized polyalkylene oxide-based polymer (e.g., terminal amines) such that a cross-linked hemostatic hydrogel is formed (e.g., at a bleeding/wound site). As a specific example, in certain cases, a dry, powdered hemostatic composition comprises a first component comprising hydrolyzed, uncrosslinked starch functionalized with a ligand comprising an leaving group selected from group G above and a second component comprising PEG-diamine or a corresponding salts thereof. In certain embodiments, the leaving group is N-oxysuccinimidyl, or N-oxysulfosuccinimidyl. The electrophilic group (e.g., comprising N-oxysuccinimidyl, comprising N-oxysulfosuccinimidyl) of the functionalized hydrolyzed, uncrosslinked starch may react with the amine groups of the PEG-diamine (e.g., upon exposure to water and optionally in the presence of an initiator), thereby forming a hemostatic hydrogel.

As another example, in some embodiments, uncrosslinked polysaccharide chains and/or microspheres modified with electrophilic groups are used in combination with a component comprising a multifunctionalized polyalkylene oxide-based polymer comprising amine groups (e.g., PEG-diamine) or corresponding salts thereof. For example, in some certain embodiments, a dry powdered composition for use in hemostasis comprises a first component (e.g., first dry powder component) comprising dry, porous microspheres of crosslinked starch functionalized with N-oxysuccinimidyl groups and a second component (e.g., second dry powder component) comprising a multifunctionalized polyalkylene oxide-based polymer comprising amine groups or corresponding salts thereof. In certain embodiments, the first and second dry component, when exposed to water and/or an initiator, can crosslink to form a hemostatic hydrogel.

Another exemplary embodiment includes a hemostatic composition where the first component (optionally in the form of a first dry powder) comprises a starch functionalized with the electrophilic groups (the electrophilic groups being at least two bonds, at least three bonds, at least four bonds, or more removed from the backbone of the starch), and the second component (optionally in the form of a second dry powder) comprises a multifunctionalized polyalkylene oxide-based polymer comprising amine groups or corresponding salts thereof. In some embodiments, the first polysaccharide component comprises a hydroxyalkyl starch (e.g., hydroxyethyl starch) functionalized with the electrophilic groups. In some such embodiments, the electrophilic groups comprise ligands comprising leaving groups selected from the same group as G above. Upon exposure to water (and optionally in the presence of an initiator), the electrophilic groups of the functionalized starch (e.g., hydroxyalkyl starch) may react with the amines of the multifunctionalized polyalkylene oxide-based polymer (e.g., terminal amines) such that a cross-linked hemostatic hydrogel is formed (e.g., at a bleeding/wound site). As a specific example, in certain cases, a dry powdered hemostatic composition comprises a first component comprising a starch (e.g., hydroxyalkyl starch such as hydroxyethyl starch) functionalized with leaving groups selected from group G above (where the leaving groups are at least four bonds removed from the backbone of the starch), and a second component comprising PEG-diamine or a corresponding salt thereof. In some such embodiments, the leaving groups are bound to the starch via a linking moiety that comprises silicon (e.g., as a result of a coupling involving a silane reagent). In some embodiments, the leaving groups are bound to the starch via a linking moiety that comprises a diester linkage (e.g., a succinate linker). In certain embodiments, the leaving group is N-oxysuccinimidyl. In certain embodiments, the leaving group is N-oxysulfosuccinimidyl. The electrophilic group (e.g., comprising N-oxysuccinimidyl or N-oxysulfosuccinimidyl) of the functionalized starch (e.g., hydroxyalkyl starch) may react with the amine groups of the PEG-diamine (e.g., upon exposure to water and optionally in the presence of an initiator), thereby forming a hemostatic hydrogel.

According to certain embodiments, the modified polysaccharide may comprise the first modified polysaccharide component (e.g., dry, porous microspheres of starch comprising polysaccharide chains functionalized with electrophilic groups as described above) in any of a variety of suitable amounts in weight percent by mass based on the overall amount of dry, porous microspheres of starch used in the hemostat formulation. For example, in some embodiments, the modified polysaccharide comprises the first modified polysaccharide component in an amount of greater than or equal to 5 wt. %, greater than or equal to 7.5 wt. %, greater than or equal to 10 wt. %, 15 wt. %, greater than or equal to 20 wt. %, greater than or equal to 25 wt. %, greater than or equal to 30 wt. %, greater than or equal to 40 wt. %, greater than or equal to 50 wt. %, greater than or equal to 60 wt. %, greater than or equal to 70 wt. %, greater than or equal to 75 wt. %, greater than or equal to 80 wt. %, greater than or equal to 90 wt. %, or greater than or equal to 95 wt. %. In certain embodiments, the modified polysaccharide comprises the first modified polysaccharide component in an amount of less than or equal to 95 wt. %, less than or equal to 90 wt. %, less than or equal to 80 wt. %, less than or equal to 75 wt. %, less than or equal to 70 wt. %, less than or equal to 60 wt. %, less than or equal to 50 wt. %, less than or equal to 40 wt. %, less than or equal to 35 wt. %, less than or equal to 30 wt. %, less than or equal to 25 wt. %, or less than or equal to 20 wt. %, less than or equal to 15 wt. %, less than or equal to 10 wt. %, less than or equal to 7.5 wt. %, or less than or equal to 5 wt. %. Combinations of the above recited ranges are also possible (e.g., the modified polysaccharide comprises the first modified polysaccharide component in an amount of greater than or equal to 5 wt. % and less than or equal to 95 wt. %, the modified polysaccharide comprises the first modified polysaccharide component in an amount of greater than or equal to 25 wt. % and less than or equal to 75 wt. %).

According to certain embodiments, the modified polysaccharide may comprise the second modified polysaccharide component (e.g., dry, porous microspheres of starch comprising polysaccharide chains functionalized with amine groups such as described above) in any of a variety of suitable amounts in weight percent by mass based on the overall amount of dry, porous microspheres of starch used in the hemostat formulation. For example, in some embodiments, the modified polysaccharide comprises the second modified polysaccharide component in an amount of greater than or equal to 5 wt. %, greater than or equal to 7.5 wt. %, greater than or equal to 10 wt. %, 15 wt. %, greater than or equal to 20 wt. %, greater than or equal to 25 wt. %, greater than or equal to 30 wt. %, greater than or equal to 40 wt. %, greater than or equal to 50 wt. %, greater than or equal to 60 wt. %, greater than or equal to 70 wt. %, greater than or equal to 75 wt. %, greater than or equal to 80 wt. %, greater than or equal to 90 wt. %, or greater than or equal to 95 wt. %. In certain embodiments, the modified polysaccharide comprises the second modified polysaccharide component in an amount of less than or equal to 95 wt. %, less than or equal to 90 wt. %, less than or equal to 80 wt. %, less than or equal to 75 wt. %, less than or equal to 70 wt. %, less than or equal to 60 wt. %, less than or equal to 50 wt. %, less than or equal to 40 wt. %, less than or equal to 35 wt. %, less than or equal to 30 wt. %, less than or equal to 25 wt. %, or less than or equal to 20 wt. %, less than or equal to 15 wt. %, less than or equal to 10 wt. %, less than or equal to 7.5 wt. %, or less than or equal to 5 wt. %. Combinations of the above recited ranges are also possible (e.g., the modified polysaccharide comprises the second modified polysaccharide component in an amount of greater than or equal to 5 wt. % and less than or equal to 95 wt. %, the modified polysaccharide comprises the second modified polysaccharide component in an amount of greater than or equal to 25 wt. % and less than or equal to 75 wt. %).

According to certain embodiments, the dry powdered hemostat composition may comprise the first component (e.g., a first dry powder containing dry, porous microspheres of starch or dry powder of hydrolyzed, uncrosslinked starch functionalized with electrophilic groups) in any of a variety of suitable amounts in weight percent by mass based on the overall mass of the two-component hemostat formulation. For example, in some embodiments, the dry powdered hemostat composition comprises the first component (e.g., first dry powder) in an amount of greater than or equal to 5 wt. %, greater than or equal to 7.5 wt. %, greater than or equal to 10 wt. %, 15 wt. %, greater than or equal to 20 wt. %, greater than or equal to 25 wt. %, greater than or equal to 30 wt. %, greater than or equal to 40 wt. %, greater than or equal to 50 wt. %, greater than or equal to 60 wt. %, greater than or equal to 70 wt. %, greater than or equal to 75 wt. %, greater than or equal to 80 wt. %, greater than or equal to 90 wt. %, or greater than or equal to 95 wt. %. In certain embodiments, the dry powdered hemostat composition comprises the first component (e.g., first dry powder component) in an amount of less than or equal to 95 wt. %, less than or equal to 90 wt. %, less than or equal to 80 wt. %, less than or equal to 75 wt. %, less than or equal to 70 wt. %, less than or equal to 60 wt. %, less than or equal to 50 wt. %, less than or equal to 40 wt. %, less than or equal to 35 wt. %, less than or equal to 30 wt. %, less than or equal to 25 wt. %, or less than or equal to 20 wt. %, less than or equal to 15 wt. %, less than or equal to 10 wt. %, less than or equal to 7.5 wt. %, or less than or equal to 5 wt. %. Combinations of the above recited ranges are also possible (e.g., the dry powdered hemostat composition comprises the first component (e.g., first dry powder) in an amount of greater than or equal to 5 wt. % and less than or equal to 95 wt. %, dry powdered hemostat composition comprises the first component (e.g., first dry powder) in an amount of greater than or equal to 25 wt. % and less than or equal to 75 wt. %).

According to certain embodiments, the dry powdered composition may comprise the second component (e.g., a second dry powder containing dry, porous microspheres of starch or dry powder of hydrolyzed, uncrosslinked starch functionalized with amine groups) in any of a variety of suitable amounts in weight percent by mass based on the overall mass of the two-component hemostat formulation. For example, in some embodiments, the dry powdered hemostat composition comprises the second component (e.g., second dry powder) in an amount of greater than or equal to 5 wt. %, greater than or equal to 7.5 wt. %, greater than or equal to 10 wt. %, 15 wt. %, greater than or equal to 20 wt. %, greater than or equal to 25 wt. %, greater than or equal to 30 wt. %, greater than or equal to 40 wt. %, greater than or equal to 50 wt. %, greater than or equal to 60 wt. %, greater than or equal to 70 wt. %, greater than or equal to 75 wt. %, greater than or equal to 80 wt. %, greater than or equal to 90 wt. %, or greater than or equal to 95 wt. %. In certain embodiments, the dry powdered hemostat composition comprises the second component (e.g., second dry powder) in an amount of less than or equal to 95 wt. %, less than or equal to 90 wt. %, less than or equal to 80 wt. %, less than or equal to 75 wt. %, less than or equal to 70 wt. %, less than or equal to 60 wt. %, less than or equal to 50 wt. %, less than or equal to 40 wt. %, less than or equal to 35 wt. %, less than or equal to 30 wt. %, less than or equal to 25 wt. %, or less than or equal to 20 wt. %, less than or equal to 15 wt. %, less than or equal to 10 wt. %, less than or equal to 7.5 wt. %, or less than or equal to 5 wt. %. Combinations of the above recited ranges are also possible (e.g., the dry powdered hemostat composition comprises the second component (e.g., second dry powder) in an amount of greater than or equal to 5 wt. % and less than or equal to 95 wt. %, dry powdered hemostat composition comprises the second dry powder component in an amount of greater than or equal to 25 wt. % and less than or equal to 75 wt. %).

In some embodiments, the above nucleophilic electrophilic crosslinking reactions are pH sensitive and are inhibited at acidic pH while being initiated by increasing the pH to neutral or basic values. In such cases, the dry, powdered hemostatic composition comprises an initiator (e.g., a crosslinking initiator) comprising a base or a basic buffer that may be used in combination with the reactive materials to initiate or facilitate crosslinking. The base or basic buffer may be provided in any of a variety of forms. In some embodiments, the crosslinking initiator is part of the second component of the dry, powdered hemostatic composition. For example, the base or basic buffer may be present as a separate solid in the second component (e.g., as separate particles of a dry powder and/or as a separate region of a composite particle). However, in some embodiments, the crosslinking initiator is provided in a different manner, such as a third component of the dry, powdered hemostatic composition (e.g., a third dry powder). In some embodiments, a crosslinking initiator is a portion of the protein, such as a chemically-modified portion of the protein (e.g., a deprotonated amino acid side chain). For example, in some embodiments, the protein of the second component of the dry, powdered hemostatic composition is at least partially deprotonated to form the free amine groups acting as an initiator. A protein may be at least partially deprotonated prior to inclusion in the dry, powdered hemostatic composition, such that the protein acts as both a crosslinking reactant component and as an initiator of the crosslinking reaction. For example, prior to inclusion in the dry, powdered hemostatic composition, the protein may be exposed to a base such that one or more acidic protons are removed from the protein. As one example, the protein may initially include lysine amino acid side chains that are protonated (having ammonium groups, —$NH_3^+$), and the protein may be exposed to a liquid under basic conditions. Under the basic conditions, a base (e.g., hydroxide ion) may deprotonate some or all of the protonated lysine amino acids of the protein to provide free amino groups (—$NH_2$) or even a negatively charged amide ion groups (—$NH^-$) if the base is sufficiently strong. The protein may then be provided in a solid form (e.g., as particles of a powder) in which at least some of the lysines are still present as free amino groups or amide ion groups.

According to certain embodiments, a crosslinking initiator comprising a base and/or basic buffer is required in order to facilitate the reaction between the leaving group G in compositions of the formula described above and the amine group of a functionalized polysaccharide, multifunctionalized polyalkylene oxide, and/or protein as described above. In some cases, the base is sodium bicarbonate. It has been observed that in some instances where a dry powder hemostat comprises relatively acidic compositions (e.g., acidic functionalized starch), foaming caused by $CO_2$ generation occurs upon acid treatment of bicarbonate anions. Therefore, in some embodiments, the base does not comprise a bicarbonate salt. In some embodiments, the base is a borate ($BO_3^-$) or metaborate ($BO_2^-$) salt. For example, in some embodiments, the base is sodium borate ($NaBO_3$), potassium borate ($KBO_3$), or a combination thereof. In some embodiments, the base is a tetraborate salt (e.g., sodium tetraborate, $Na_2B_4O_7$, potassium tetraborate, $K_2B_4O_7$). It has been observed that such borate and/or metaborate salts do not cause observable foaming upon combination with acidic compositions such as functionalized hydrolyzed starch. According to certain embodiments, the basic crosslinking initiator is a base and/or basic buffer that does not include amine functionalities.

In some embodiments, the base and/or basic buffer of the crosslinking initiator is non-gas-forming in aqueous solutions. In this context, a gas-forming base and/or basic buffer is one that, upon reaction with one or more protons in water, undergoes a gas evolution reaction under standard conditions. For example, reaction of bicarbonate with a proton (e.g., in the form of a hydronium ion $H_3O^+$) can generate carbon dioxide (a gaseous species) and water. Therefore, bicarbonate salts such as sodium bicarbonate are considered to be gas-forming. In contrast, reaction of a non-gas-forming base and/or basic buffer with a proton in water does not form a gaseous species. For example, reaction of dibasic phosphate ($HPO_4^{2-}$) with one or more protons (e.g., in the form of a hydronium ion, $H_3O^+$) generates monobasic ($H_2PO_4$) or phosphoric acid ($H_3PO_4$), neither of which are gaseous species under standard conditions. Therefore, phosphate salts such as sodium phosphate dibasic are considered non-gas-forming. Other examples of non-gas-forming bases and/or basic buffers include, but are not limited to sodium borate, potassium tetraborate, and sodium hydroxide. It has been observed in the context of this disclosure that gas evolution reactions by gas-forming bases and/or basic buffers such as sodium bicarbonate can generate gas bubbles during crosslinking reactions under some conditions. Formation of gas bubbles may disrupt the integrity of resulting hemostatic hydrogels and/or adversely affect adherence of such a hemostatic hydrogel with bleeding tissue. Inclusion of non-gas-forming bases and/or basic buffers may mitigate or eliminate bubble formation and resulting adverse effects on hemostasis. In some embodiments, the dry, powdered hemostatic composition is free from any powdered gas-forming basic salt and/or basic buffer. In some embodiments, the dry, powdered hemostatic composition is free from any powdered basic salt and/or basic buffer comprising a carbonate anion or bicarbonate anion.

According to certain embodiments, the reaction between the leaving group G and the amine group occurs at pH of greater than or equal to 7, and the crosslinking reaction in situ is made to occur (e.g., through addition to a base or basic buffer to one or both of the reactive components) at a pH of greater than or equal to 7, a pH of greater than or equal to 7.4, a pH of greater than or equal to 8, a pH of greater than or equal to 9, a pH of greater than or equal to 10.

According to certain embodiments, a dry powder hemostat comprises a mixture of a multifunctionalized electrophilic polymeric first component (e.g., first dry powder such as PEG(SS)2) in any of a variety of suitable amounts in weight percent by mass in combination with a second component comprising a nucleophilic polymer (e.g., a functionalized polysaccharide). For example, in some embodiments, the dry powder composition (e.g., dry powder mixture) comprises the first component (e.g., first dry powder) in an amount of greater than or equal to 15 wt. %, greater than or equal to 20 wt. %, greater than or equal to 25 wt. %, greater than or equal to 30 wt. %, or greater than or equal to 35 wt. %. of the total mixture. In certain embodiments, the dry powder composition (e.g., dry powder mixture) comprises the first component (e.g., first dry powder) in an amount of less than or equal to 40 wt. %, less than or equal to 35 wt. %, less than or equal to 30 wt. %, less than or equal to 25 wt. %, or less than or equal to 20 wt. %. Combinations of the above recited ranges are also possible (e.g., the dry powder mixture comprises the first dry powder in an amount of greater than or equal to 15 wt. % and less than or equal to 40 wt. %, the dry powder mixture comprises the first dry powder in an amount of greater than or equal to 20 wt. % and less than or equal to 25 wt. %).

According to certain embodiments, the second component of the dry powder composition (e.g., dry powder mixture) may comprise the protein (e.g., albumin) in any of a variety of suitable amounts in weight percent by mass. For example, in certain embodiments, the dry powder composition (e.g., dry powder mixture) comprises the protein in an amount of greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, greater than or equal to 55 wt. %, or greater than or equal to 60 wt. % of the total mixture. In certain embodiments, the dry powder composition (e.g., dry powder mixture) comprises the protein in an amount of less than or equal to 80 wt. %, less than or equal to 75 wt. %, less than or equal to 70 wt. %, less than or equal to 65 wt. %, less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, or less than or equal to 25 wt. % of the total mixture. Combinations of the above recited ranges are also possible (e.g., the dry powder mixture comprises the protein in an amount of greater than or equal to 20 wt. % and less than or equal to 65 wt. %, the dry powder mixture comprises the protein in an amount of greater than or equal to 40 wt. % and less than or equal to 50 wt. %). According to certain embodiments, the dry powder composition, when applied to blood, may require a lesser amount of the protein as compared to when the dry powder composition is applied to other media (e.g., saline) due to the presence of additional proteins (e.g., albumin) and/or cellular components in the blood.

In some embodiments, the second component of the dry powder composition (e.g., dry powder mixture) comprises the protein (e.g., albumin) in an amount of greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, greater than or equal to 55 wt. %, greater than or equal to 60 wt. %, greater than or equal to 65 wt. %, greater than or equal to 70 wt. %, greater than or equal to 75 wt. %, greater than or equal to 80 wt. %, greater than or equal to 85 wt. %, greater than or equal to 90 wt. %, greater than or equal to 95 wt. %, greater than or equal to 98 wt. %, greater than or equal to 99 wt. %, greater than or equal to 99.8 wt. %, or greater by mass of the second component. In some embodiments, the second component of the dry powder composition (e.g., dry powder mixture) comprises the protein (e.g., albumin) in an amount of less than or equal to 99.9 wt. %, less than or equal to 99.8 wt. %, less than or equal to 99 wt. %, less than or equal to 98 wt. %, less than or equal to 95 wt. %, less than or equal to 90 wt. %, less than or equal to 85 wt. %, less than or equal to 65 wt. %, less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, or less than or equal to 25 wt. % by mass of the second component. Combinations of the above recited ranges are also possible (e.g., the second component comprises the protein in an amount of greater than or equal to 20 wt. % and less than or equal to 99.9 wt. % by mass of the second component, the dry powder mixture comprises the protein in an amount of greater than or equal to 40 wt. % and less than or equal to 90 wt. % by mass of the second component).

According to some embodiments, the second component comprises a protein or other nucleophilic polymer consisting essentially of particles having a certain particle size. As used herein, the phrase "consisting essentially of particles having a certain particle size distribution" means that greater than or equal to 80 wt. % of the particles fall within the stated particle size range. In certain cases, greater than or equal to 90 wt. %, greater than or equal to 95 wt. %, greater than or equal to 98 wt. %, greater than or equal to 99 wt. %, or greater than or equal to 99.9 wt. % of the particles fall within the stated particle size range. Similarly, "consisting essentially of particles having a certain particle size" means that greater than or equal to 80 wt. % of the particles fall within a range that is ±20% of the stated particle size. In certain cases, greater than or equal to 90 wt. %, greater than or equal to 95 wt. %, greater than or equal to 98 wt. %, greater than or equal to 99 wt. %, or greater than or equal to 99.9 wt. % fall within a range that is ±20% of the stated particle size. Also similarly, "consisting essentially of particles not exceeding a certain particle size" or "consisting essentially of particles having at least a certain particle size" means that greater than or equal to 80 wt. % of the particles do not exceed, or have a size that is at least, respectively, the stated particle size. In certain cases, greater than or equal to 90 wt. %, greater than or equal to 95 wt. %, greater than or equal to 98 wt. %, greater than or equal to 99 wt. %, or greater than or equal to 99.9 wt. % of the particles do not exceed, or have a size that is at least, respectively, the stated particle size.

In certain embodiments, the protein particles are substantially spherical and the particle size is a maximum cross-sectional particle diameter. Other particle shapes, however, are also possible. Without wishing to be bound by theory, in some embodiments, the measured time it takes for the dry powdered composition to crosslink and/or the degree of crosslinking may depend on the particle size of the protein or other nucleophilic polymer. Accordingly, it may be advantageous, in certain aspects, to employ a protein or other nucleophilic polymer consisting essentially of particles within a certain particle size range in order to control the time it takes for the dry powdered composition to crosslink when applied to a bleeding/wound site and/or the extent of crosslinking, as is explained below in greater detail.

In certain embodiments, the protein or other nucleophilic polymer particles may be separated by particle size (e.g., maximum particle diameter) using methods known to a person of ordinary skill in the art, such as using a sieve and/or filter to separate target particles above and below a certain sieve/filter cutoff size. In some embodiments the sieve-separated protein or other nucleophilic polymer particle size may be further measured using spectroscopic techniques, such as dynamic light scattering (DLS), transmission electron microscopy (TEM), or scanning electron microscopy (SEM). In some aspects, the spectroscopic techniques may be used to supplement and/or confirm the particle size of the particles that have been separated using sieves and/or filters.

The protein or other nucleophilic polymer particles may have any of a variety of suitable particle sizes. In certain embodiments, for example, the protein or other nucleophilic polymer consists essentially of particles having a particle size of greater than or equal to 50 micrometers, greater than or equal to 100 micrometers, greater than or equal to 150 micrometers, greater than or equal to 200 micrometers, greater than or equal to 250 micrometers, greater than or equal to 300 micrometers, greater than or equal to 350 micrometers, greater than or equal to 400 micrometers, greater than or equal to 450 micrometers, or greater than or equal to 500 micrometers. In some embodiments, the protein or other nucleophilic polymer consists essentially of particles having a particle size of less than or equal to 600 micrometers, less than or equal to 500 micrometers, less than or equal to 450 micrometers, less than or equal to 400 micrometers, less than or equal to 350 micrometers, less than or equal to 300 micrometers, less than or equal to 250 micrometers, less than or equal to 200 micrometers, less than or equal to 150 micrometers, or less than or equal to 100 micrometers. Combinations of the above recited ranges are also possible (e.g., the protein or other nucleophilic polymer consists essentially of particles having a particle size of greater than or equal to 50 micrometers and less than or equal to 600 micrometers, the protein or other nucleophilic polymer consists essentially of particles having a particle size of greater than or equal to 100 micrometers and less than or equal to 250 micrometers), etc.

In certain embodiments, the second component comprises a protein or other nucleophilic polymer that comprises a plurality of particles having a certain bulk or tapped particle density (e.g., tapped particle density). Without wishing to be bound by theory, in some embodiments, the measured time it takes for the dry powdered composition to crosslink and the degree of crosslinking may depend on the particle density (e.g., tapped particle density) of the protein or other nucleophilic polymer. Accordingly. it may be advantageous, in certain aspects, to employ a composition comprising a protein or other nucleophilic polymer with a certain particle density (e.g., tapped particle density) in order to control the time it takes for the dry powdered composition to crosslink or the degree of crosslinking when applied to a bleeding/wound site, as is explained below in greater detail.

In some embodiments, employing a composition comprising a protein or other nucleophilic polymer with a certain particle density may have further advantages in addition to controlling the time it takes for the dry powdered composition to crosslink. In some aspects, for example, employing a composition comprising a protein or other nucleophilic polymer with a certain particle density may affect the time it takes for the dry powdered composition to break the surface tension of blood, penetrate through the layer of blood, and adhere to the underlying tissue. In some embodiments, for example, a protein or other nucleophilic polymer with a higher particle density may break the surface tension of blood, penetrate through the layer of blood, and adhere to the underlying tissue more quickly than a protein or other nucleophilic polymer with a lower particle density.

According to some embodiments, the particle density of the protein or other nucleophilic polymer may be measured using methods known to a person of ordinary skill in the art. For example, the particle densities referred to herein are determined using a tapped density method. Specifically, for the measurements made herein, a tapped density measurement is made as follows: the mass of the protein and/or other nucleophilic polymer is measured using a standard analytical balance capable of reading up to 0.1 mg, for example, the mass of the protein and/or other nucleophilic polymer may be measured by adding greater than a 6.0 ml volume of the protein and/or other nucleophilic polymer to a calibrated 10 ml graduated cylinder that is capable or reading up to 0.1 ml (e.g., Pyrex No. 3022) that has been pre-tared on the analytical balance; the bottom of the graduated cylinder containing the protein and/or other nucleophilic polymer is then repeatedly "tapped" against a flat surface in order to increase the packing density of the protein or other nucleophilic polymer in the graduated cylinder until the volume of the protein and/or other nucleophilic polymer does not change more than 0.1 mL between taps; and the tapped density is determined by dividing the measured mass by the measured volume.

In certain embodiments, the particle density of the protein or other nucleophilic polymer can be controlled. In some embodiments, for example, the particle density of the protein or other nucleophilic polymer may be changed by lyophilizing solutions of different concentrations of the protein or other nucleophilic polymers. For example, in some embodiments, the particle density of the starting material of the protein or other nucleophilic polymer may be determined as described above, and a solution of the protein or other nucleophilic polymer is solubilized and lyophilized to provide a particle density that is different than the particle density of the starting material. In certain embodiments, the particle density of the protein or other nucleophilic polymer after lyophilization is preferably lower than the particle density of the protein or other nucleophilic polymer starting material. The final, post lyophilization density can be controlled at least in part by controlling the concentration of the protein or other nucleophilic polymer in the solution that is lyophilized. In some embodiments, for example, more concentrated solutions lead to higher post-lyophilization densities as compared to less concentrated solutions. In some embodiments, the post-lyophilization density is lower than the particle density of the protein or other nucleophilic polymer starting material. In certain other embodiments, the post-lyophilization density is greater than the particle density of the protein or other nucleophilic starting material. A post-lyophilization particle density that is greater than the starting material particle density may be obtained, in some embodiments, by lyophilizing solutions containing high concentrations of starting materials with low particle densities (e.g., less than 0.30 g/ml). In some embodiments, the particle density of the protein or other nucleophilic polymer starting material may be increased by roller compacting and granulating the protein or other nucleophilic polymer starting material. In certain embodiments, it may be advantageous to increase the particle density of the protein by roller compacting the second component comprising the protein. In certain embodiments, it may be advantageous to increase the particle density of the protein by roller compacting the second component comprising the protein and the crosslinking initiator (e.g., the base or basic buffer) together.

The protein or other nucleophilic polymer particles may have any of a variety of suitable particle densities (e.g., tapped particle densities). For example, in certain embodiments, the protein or other nucleophilic polymer comprises a plurality of particles having a particle density of greater than or equal to 0.20 g/ml, greater than or equal to 0.30 g/ml, greater than or equal to 0.35 g/ml, greater than or equal to 0.40 g/ml, greater than or equal to 0.45 g/ml, greater than or equal to 0.50 g/ml, greater than or equal to 0.55 g/ml, greater than or equal to 0.60 g/ml, greater than or equal to 0.65 g/ml, greater than or equal to 0.70 g/ml, greater than or equal to 0.75 g/ml. In some embodiments, the protein or other nucleophilic polymer comprises a plurality of particles having a particle density of less than or equal to 0.80 g/ml, less than or equal to 0.75 g/ml, less than or equal to 0.70 g/ml, less than or equal to 0.65 g/ml, less than or equal to 0.60 g/ml, less than or equal to 0.50 g/ml, less than or equal to 0.45 g/ml, less than or equal to 0.40 g/ml, or less than or equal to 0.35 g/ml. Combinations of the above recited ranges are also possible (e.g., the protein or other nucleophilic polymer comprises a plurality of particles having a particle density of greater than or equal to 0.20 g/ml and less than or equal to 0.80 g/ml, the protein or other nucleophilic polymer comprises a plurality of particles having a particle density of greater than or equal to 0.35 g/ml and less than or equal to 0.45 g/ml).

In a specific, non-limiting embodiment, the dry powder composition comprises lyophilized bovine serum albumin with a tapped particle density greater than or equal to 0.60 g/ml and less than or equal to 0.70 g/ml. In another specific non-limiting embodiment, the dry powder composition comprises lyophilized bovine serum albumin with a particle density greater than or equal to 0.20 g/ml and less than or equal to 0.40 g/ml. In another specific non-limiting embodiment, the dry powder composition comprises lyophilized human serum albumin with a particle density greater than or equal to 0.20 g/mL and less than or equal to 0.40 g/mL.

According to certain embodiments, the functionalized polysaccharides comprising electrophilic groups, the multifunctionalized polymeric compositions (e.g., describable by the formula G-LM-PEG-LM-G, I—(—X-LM-G)$_n$, or I-(LM-G)) or other electrophilic polymer components comprises a plurality of particles having any of a variety of suitable particle sizes and/or particle densities (e.g., tapped particle densities), which may be determined as described above in reference to the protein or other nucleophilic polymers.

In some embodiments, the multifunctionalized polymeric composition describable by the formula G-LM-PEG-LM-G, I—(—X-LM-G)$_n$, or I-(LM-G) (e.g., PEG(SS)2, PEG(SG4), PEG(SG)4LA, and/or any other of the first component electrophilic compositions described herein (collectively "multifunctionalized polymeric composition")) comprises a plurality of particles having a particle size of greater than or equal to 10 micrometers, greater than or equal to 50 micrometers, greater than or equal to 100 micrometers, greater than or equal to 150 micrometers, greater than or equal to 200 micrometers, greater than or equal to 250 micrometers, greater than or equal to 300 micrometers, greater than or equal to 350 micrometers, greater than or equal to 400 micrometers, greater than or equal to 450 micrometers, greater than or equal to 500 micrometers, or greater than or equal to 550 micrometers. In certain embodiments, the functionalized polysaccharides comprising electrophilic groups, the multifunctionalized polymeric compositions comprises a plurality of particles having a particle size of less than or equal to 600 micrometers, less than or equal to 550 micrometers, less than or equal to 500 micrometers, less than or equal to 450 micrometers, less than or equal to 400 micrometers, less than or equal to 350 micrometers, less than or equal to 300 micrometers, less than or equal to 250 micrometers, less than or equal to 200 micrometers, less than or equal to 150 micrometers, less than or equal to 100 micrometers, or less than or equal to 50 micrometers. Combinations of the above recited ranges are also possible (e.g., the a plurality of particles having a particle size greater than or equal to 10 micrometers and less than or equal to 600 micrometers, a plurality of particles having a particle size greater than or equal to 200 micrometers and less than or equal to 300 micrometers).

In certain embodiments, the functionalized polysaccharides comprising electrophilic groups, the multifunctionalized polymeric compositions comprises a plurality of particles having a particle density (e.g., tapped particle density) greater than or equal to 0.20 g/ml, greater than or equal to 0.25 g/ml, greater than or equal to 0.30 g/ml, greater than or equal to 0.35 g/ml, greater than or equal to 0.40 g/ml, greater than or equal to 0.45 g/ml, greater than or equal to 0.50 g/ml, or greater than or equal to 0.55 g/ml. In some embodiments, the functionalized polysaccharides comprising electrophilic groups, the multifunctionalized polymeric compositions comprises a plurality of particles having a particle density (e.g., tapped particle density) of less than or equal to 1.0 g/mL, less than or equal to 0.90 g/mL, less than or equal to 0.80 g/mL, less than or equal to 0.70 g/mL, less than or equal to 0.60 g/ml, less than or equal to 0.55 g/ml, less than or equal to 0.50 g/ml, less than or equal to 0.45 g/ml, less than or equal to 0.40 g/ml, less than or equal to 0.35 g/ml, less than or equal to 0.30 g/ml, or less than or equal to 0.25 g/ml. Combinations of the above recited ranges are also possible (e.g., a plurality of particles having a particle density greater than or equal to 0.20 g/ml and less than or equal to 1.0 g/ml, a plurality of particles having a particle density greater than or equal to 0.25 g/ml and less than or equal to 0.35 g/ml).

According to some embodiments, the crosslinking initiator (e.g., a basic salt such as sodium bicarbonate, sodium borate, etc.) comprises a plurality of particles having any of a variety of suitable particle sizes and/or particle densities (e.g., tapped particle densities), which may be determined as described above in reference to the protein.

In certain embodiments, the crosslinking initiator comprises a plurality of particles having a particle size of greater than or equal to 20 micrometers, greater than or equal to 50 micrometers, greater than or equal to 100 micrometers, greater than or equal to 150 micrometers, greater than or equal to 200 micrometers, greater than or equal to 250 micrometers. In some embodiments, the crosslinking initiator comprises a plurality of particles having a particle size of less than or equal to 300 micrometers, less than or equal to 250 micrometers, less than or equal to 200 micrometers, less than or equal to 150 micrometers, less than or equal to 100 micrometers, or less than or equal to 50 micrometers. Combinations of the above recited ranges are also possible (e.g., the crosslinking initiator comprises a plurality of particles having a particle size of greater than or equal to 20 micrometers and less than or equal to 300 micrometers, the crosslinking initiator comprises a plurality of particles having a particle size of greater than or equal to 50 micrometers and less than or equal to 100 micrometers).

In some embodiments, the crosslinking initiator comprises a plurality of particles having a particle density (e.g., tapped particle density) greater than or equal to 0.50 g/ml, greater than or equal to 0.60 g/ml, greater than or equal to 0.70 g/ml, greater than or equal to 0.80 g/ml, greater than or equal to 0.90 g/ml, greater than or equal to 1.00 g/ml, greater than or equal to 1.10 g/ml; greater than or equal to 1.20 g/ml, greater than or equal to 1.30 g/ml, or greater than or equal to 1.40 g/ml. In certain embodiments, the crosslinking initiator comprises a plurality of particles having a particle density (e.g., tapped particle density) less than or equal to 1.50 g/ml, less than or equal to 1.40 g/ml, less than or equal to 1.30 g/ml, less than or equal to 1.20 g/ml, less than or equal to 1.10 g/ml, less than or equal to 1.00 g/ml, less than or equal to 0.90 g/ml, less than or equal to 0.80 g/ml, less than or equal to 0.70 g/ml, or less than or equal to 0.60 g/ml. Combinations of the above recited ranges are also possible (e.g., the crosslinking initiator comprises a plurality of particles having a particle density greater than or equal to 0.50 g/ml and less than or equal to 1.50 g/ml, the crosslinking initiator comprises a plurality of particles having a particle density greater than or equal to 0.90 g/ml and less than or equal to 1.20 g/ml).

In some embodiments, a dry powder (e.g., dry powder component) comprising a functionalized polysaccharide has a relatively high particle density as measured by the tapped density procedure described above. Having a relatively high particle density may promote improved performance of a dry hemostatic powder, because if powder particles are too fine or light, the powder may tend to float upon exposure to an aqueous solution (e.g., blood), and a poor-quality gel may be formed. It has unexpectedly been observed that certain solvent mixtures used during formation of a dry powder component comprising a functionalized polysaccharide (e.g., hydrolyzed, uncrosslinked starch) can tune the particle density of the dry powder. For example, precipitation from solvent mixtures comprising a first polar solvent and a second non-polar solvent may contribute to increased particle density of precipitates compared to mixtures comprising only the polar solvent (e.g., by affecting rates of agglomeration and/or precipitation). One example of such a solvent mixture is a mixture of an alcohol (e.g., ethanol) and an ether (e.g., diethyl ether). The mixture be, for example, a 50:50 mixture by volume of the first polar solvent and the second non-polar solvent.

In some embodiments, a component of a dry powder hemostat (e.g., any of the first components or second component as described above) is a dry powder having a particle density (as determined by the tapped density method) of greater than or equal to 0.20 g/mL, greater than or equal to 0.30 g/mL, greater than or equal to 0.35 g/mL, greater than or equal to 0.40 g/mL, greater than or equal to 0.45 g/mL, greater than or equal to 0.50 g/mL, greater than or equal to 0.55 g/mL, greater than or equal to 0.6 g/mL, or greater. In some embodiments, a component of a dry powder hemostat (e.g., any of the first components or second component as described above) is a dry powder having a particle density of less than or equal to 1.0 g/mL, less than or equal to 0.80 g/mL, less than or equal to 0.75 g/mL, less than or equal to 0.70 g/mL, less than or equal to 0.65 g/mL, or less. Combinations (e.g., greater than or equal to 0.20 g/mL and less than or equal to 1.0 g/mL, or greater than or equal to 0.5 g/mL and less than or equal to 0.70 g/mL) are possible.

For embodiments in which the second component of the dry powder composition (e.g., second powder of a dry powder mixture) further comprises a base or basic buffer as a crosslinking initiator (e.g., sodium bicarbonate, sodium borate), such base or basic buffer may be present in any suitable amount. Without wishing to be bound by theory, the amount of the base or basic buffer may affect the reactivity of the dry powder composition, such as the measured time it takes for the dry powdered composition to crosslink, which is explained below in greater detail. Accordingly, in certain embodiments, it may be advantageous to select the amount of base or basic buffer in order to advance or delay hemostasis when the dry powder composition is applied to a bleeding/wound site.

The dry powder composition may comprise the base of basic buffer in any of a variety of suitable amounts. For example, in certain embodiments, the second component of the dry powder composition (e.g., dry powder mixture) comprises the basic crosslinking initiator in an amount of greater than or equal to 1 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, or greater than or equal to 40 wt. %. In certain embodiments, the second component of the dry powder composition (e.g., dry powder mixture) comprises the basic crosslinking initiator in an amount of less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, or less than or equal to 5 wt. %. Combinations of the above recited ranges are also possible (e.g., the dry powder mixture comprises the basic crosslinking initiator in an amount of greater than or equal to 1 wt. % and less than or equal to 45 wt. %, the dry powder mixture comprises the basic crosslinking initiator in an amount of greater than or equal to 25 wt. % and less than or equal to 35 wt. %).

The time it takes for the dry powder composition to crosslink may determine how fast the composition forms a hemostatic hydrogel when the dry powder is applied to a bleeding/wound site. It may be beneficial for the dry powdered composition to crosslink in a substantially short time in order to quickly promote hemostasis when applied to a bleeding/wound site. In some aspects, it may be beneficial to delay formation of the hemostatic hydrogel depending on the location of the bleeding/wound site and/or the state of the patient. The "measured crosslink time" as used herein is determined by first applying the dry powder composition to a vial containing either whole blood or a solution of 0.9% normal saline as follows: to a 15.5 mm×50 mm Fisherbrand™ Vial containing a 3 mm×12.7 mm VWR™ brand Yellow Micro Stir Bar on a stir plate adjusted to 60 RPM, add either 631 microliters of whole blood with 33 microliters of 0.2 M $CaCl_2$, or 664 microliters of 0.9% normal saline, at 37° C.; to this add 166 mg of the dry powder composition (shaking lightly as needed to prevent powder from sticking to the sides of the vial); the initial time ($T_0$) is recorded upon addition of the dry powder composition, and the timer is stopped (at $T_F$) when gelation causes the stir bar to stop spinning or when gelation occurs (as indicated by an obvious change in consistency). The stir bar may not come to a complete stop. If the stir bar continues beyond 3 minutes without an obvious change in consistency, a time of ">3 minutes" is recorded, but if the operator observes an obvious change in consistency indicating gel formation, the time of such observation is recorded and the test is discontinued even if the stir bar may not completely stop in all cases. The measured crosslink time is the time when the timer is stopped minus the initial time.

The dry powder composition may have any of a variety of suitable measured crosslink times. In some embodiments, for example, the dry powder composition may have a measured crosslink time of greater than or equal to 10 seconds, greater than or equal to 15 seconds, greater than or equal to 20 second, greater than or equal to 25 seconds, greater than or equal to 30 seconds, greater than or equal to 40 seconds greater than or equal to 50 seconds, greater than or equal to 100 seconds, greater than or equal to 150 seconds, greater than or equal to 200 seconds, greater than or equal to 250 seconds, greater than or equal to 300 seconds, greater than or equal to 350 seconds, greater than or equal to 400 seconds, or greater than or equal to 450 seconds. In certain embodiments, the dry powder composition may have a measured crosslink time of less than or equal to 500 seconds, less than or equal to 450 seconds, less than or equal to 400 seconds, less than or equal to 350 seconds, less than or equal to 300 seconds, less than or equal to 250 seconds, less than or equal to 200 seconds, less than or equal to 150 seconds, less than or equal to 100 seconds, less than or equal to 75 seconds, less than or equal to 50 seconds. Less than or equal to 40 seconds, less than or equal to 30 seconds, or less than or equal to 25 seconds. Combinations of the above recited ranges are also possible (e.g., the dry powder composition may have a measured crosslink time of greater than or equal to 10 seconds less than or equal to 500 seconds, the dry powder composition may have a measured crosslink time or greater than or equal to 15 seconds and less than or equal to 100 seconds).

In some embodiments wherein the second component comprises a protein, the measured crosslink time of the dry powder composition may depend on the type of protein and/or source of the protein. For example, in certain embodiments wherein the protein comprises albumin, the measured crosslink time may depend on the source of albumin. In a certain non-limiting embodiment, for example, the protein comprises bovine serum albumin and the measured crosslink time is greater than or equal to 30 seconds and less than or equal to 50 seconds. In another non-limiting embodiment, the protein comprises human serum albumin and the measured crosslink time is greater than 10 seconds and less than 30 seconds. In yet another non-limiting embodiment, the protein may comprise recombinant human albumin and the measured crosslink time is greater than or equal to 30 seconds and less than or equal to 70 seconds. In certain embodiments, the measured crosslink time of the dry powder composition may depend on the media that the dry powder composition is applied to. For example, in some embodiments, the measured crosslink time of the dry powder composition is different when mixed with whole blood as compared to normal saline (i.e., 0.90% w/v NaCl in deionized water). In some embodiments, for example, the dry powder composition has a measured crosslink time of greater than or equal to 10 seconds, greater than or equal to 15 second, greater than or equal to 50 seconds, or greater than or equal to 100 seconds when the dry powder composition is applied to whole blood. In certain embodiments, the dry powder composition has a measured crosslink time of less than or equal to 150 seconds, less than or equal to 100 seconds, or less than or equal to 50 seconds when the dry powder composition is applied to whole blood. Combinations of the above recited ranges are also possible (e.g., the dry powder has a measured crosslink time of greater than or equal to 10 seconds and less than or equal to 150 seconds when the dry powder composition is applied to whole blood, the dry powder has a crosslink time or greater than or equal to 50 seconds and less than or equal to 100 seconds when the dry powder is applied to blood). According to certain embodiments, the dry powder composition may crosslink at a substantially faster rate in blood as compared to other media (e.g., saline), due to the presence of additional proteins (e.g., albumin) and/or cellular components in the blood.

According to certain embodiments, the dry powder composition has a measured crosslink time of greater than or equal to 10 seconds, greater than or equal to 15 seconds, greater than or equal to 50 seconds, greater than or equal to 100 seconds, greater than or equal to 150 seconds, or greater than or equal to 200 seconds when the composition is added to normal saline. In some embodiments, the dry powder composition has a crosslink time of less than or equal to 250 seconds, less than or equal to 200 seconds, less than or equal to 150 seconds, less than or equal to 100 seconds, or less than or equal to 50 seconds when the dry powder composition is added to normal saline. Combinations of the above recited ranges are also possible (e.g., the dry powder composition has a measured crosslink time of greater than or equal to 10 seconds and less than or equal to 250 seconds when the dry powder composition is added to normal saline, the dry powder composition has a measured crosslink time or greater than or equal to 50 seconds and less than or equal to 150 seconds when the dry powder composition is added to normal saline).

As explained above, the measured crosslink time of the dry powder composition may be affected by certain properties of the reactive powder(s) (e.g., particle size and/or particle density) of the dry powder composition. For example, in some embodiments, the protein or other nucleophilic polymer consists essentially of particles having a particle size greater than or equal to 100 micrometers, greater than or equal to 150 micrometers, or greater than or equal to 200 micrometers, and the dry powder composition may have a measured crosslink time of greater than or equal to 10 seconds and less than or equal to 75 seconds, or in other embodiments greater than or equal to 75 seconds and less than or equal to 150 seconds, when the dry powder composition is added to blood. In some embodiments, the protein or other nucleophilic polymer consists essentially of particles having a particle size of less than or equal to 250 micrometers, less than or equal to 200 micrometers, or less than or equal to 150 micrometers, and the dry powder composition has a measured crosslink time of greater than or equal to 10 seconds and less than or equal to 75 seconds when the dry powder composition is added to whole blood.

In some embodiments, the protein or other nucleophilic polymer consists essentially of particles having a particle size of greater than or equal to 100 micrometers, greater than or equal to 150 micrometers, or greater than or equal to 200 micrometers, and the dry powder composition has a measured crosslink time of greater than or equal to 10 seconds and less than or equal to 100 seconds, or in other embodiments greater than or equal to 100 seconds and less than or equal to 150 seconds, when the dry powder composition is added to normal saline. In some embodiments, the protein or other nucleophilic polymer consists essentially of particles having a particle size of less than or equal to 250 micrometers, less than or equal to 200 micrometers, or less than or equal to 150 micrometers, and the dry powder composition has a measured crosslink time of greater than or equal to 10 seconds and less than or equal to 75 seconds when the dry powder composition is added to normal saline.

In certain embodiments, the protein or other nucleophilic polymer comprises a plurality of particles having a tapped particle density of greater than or equal to 0.35 g/ml, or greater than or equal to 0.40 g/ml, or greater than 0.50 g/ml, or greater than 0.60 g/ml, and the dry powder composition may have a measured crosslink time of greater than or equal to 10 seconds and less than or equal to 75 seconds, or in other embodiments greater than or equal to 75 seconds and less than or equal to 150 seconds, when the dry powder composition is added to whole blood. In some embodiments, the protein or other nucleophilic polymer comprises a plurality of particles having a tapped particle density of less than or equal to 0.45 g/ml or less than or equal to 0.40 g/ml, and the composition may have a measured crosslink time of greater than or equal to 10 seconds and less than or equal to 75 seconds, or in other embodiments greater than or equal to 75 seconds and less than or equal to 150 seconds, when the dry powder composition is added to whole blood.

In some embodiments, the protein or other nucleophilic polymer comprises a plurality of particles having a tapped particle density of greater than or equal to 0.35 g/ml, or greater than or equal to 0.40 g/ml, or greater than 0.50 g/ml, or greater than 0.60 g/ml, and the dry powder composition may have a measured crosslink time of greater than or equal to 10 seconds and less than or equal to 100 seconds, or in other embodiments greater than or equal to 100 seconds and less than or equal to 150 seconds when the dry powder composition is added to normal saline. In some embodiments, the protein or other nucleophilic polymer comprises a plurality of particles having a tapped particle density of less than or equal to 0.45 g/ml or less than or equal to 0.40 g/ml, and the dry powder composition may have a measured crosslink time of greater than or equal to 10 seconds and less than or equal to 100 seconds, or in other embodiments greater than or equal to 100 seconds and less than or equal to 150 seconds, when the dry powder composition is added to normal saline.

In certain cases, the measured crosslink time of the dry powder composition may be affected by the relative amount of base or basic buffer. For example, in certain embodiments, the dry powder composition may comprise a crosslinking initiator (e.g., a base or basic buffer), and the amount of the crosslinking initiator may affect the time it takes for the composition to crosslink in various media (e.g., a solution of blood, a solution of saline) due to changes in the pH value of the solution. In some embodiments, the dry powder comprises greater than or equal to 1 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, or greater than or equal to 40 wt. % by mass base or basic buffer, and the composition has a measured crosslink time of greater than or equal to 10 seconds and less than or equal to 150 seconds when the dry powder composition is added to whole blood. In some embodiments, the dry powder comprises less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, or less than or equal to 1 wt. % by mass base or basic buffer, and the dry powder composition has a measured crosslink time of greater than or equal to 10 seconds and less than or equal to 150 seconds when the dry powder composition is added to whole blood.

In some embodiments, the dry powder composition comprises greater than or equal to 1 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, or greater than or equal to 40 wt. % by mass base or basic buffer, and the dry powder composition has a measured crosslink time of greater than or equal to 10 seconds and less than or equal to 250 seconds, or in other embodiments greater than or equal to 250 seconds and less than or equal to 400 seconds, when the dry powder composition is added to normal saline. In some embodiments, the dry powder composition comprises less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, or less than or equal to 1 wt. % by mass base or basic buffer, and the dry powder composition has a measured crosslink time of greater than or equal to 10 seconds and less than or equal to 250 seconds when the dry powder composition is added to normal saline.

In any of the above described embodiments, the dry powder crosslinking hemostat composition (e.g., dry powder crosslinking hemostat mixture) may comprise other active agents or ingredients for various purposes, for example biomaterials, such as crosslinked gelatin or starch particles to allow for additional blood absorption, biologics such as thrombin to accelerate blood clotting, or any of a variety of suitable antimicrobials.

Another aspect disclosed herein relates to methods for controlling bleeding, which may employ, but are not necessarily limited to, the above described hemostatic materials. For example, in some embodiments, the method comprises applying any of the above described the crosslinkable dry powder hemostats (e.g., the various crosslinking dry powder compositions and/or mixtures) to a bleeding/wound site (e.g., bleeding tissue). In certain embodiments, upon exposure to aqueous liquid in the bleeding/wound site, the crosslinkable dry powder crosslinks to form a hemostatic hydrogel capable of stopping and/or reducing bleeding at the bleeding/wound site.

FIG. 1, for example, shows steps in an exemplary method for forming a hemostatic hydrogel with a dry powdered mixture. In method 100, step 110 comprises admixing a first dry powder component and the second dry powder component (e.g., one or more of the candidate first and second component material described above) to form a dry powder mixture. Step 120 comprises applying the dry powder mixture to a bleeding/wound site, and step 130 comprises allowing the dry powder mixture to crosslink into a hemostatic hydrogel upon exposure to aqueous liquid in the bleeding/wound site capable of stopping and/or reducing bleeding at the bleeding/wound site. The dry, powdered hemostatic composition may be applied the bleeding/wound site as a single powder mixture. Alternatively (not pictured), the first and second powder components could be applied separately to the site simultaneously or sequentially without prior formation of a powder mixture. For example, in some embodiments, a first powder comprising the first component and a second powder comprising the second component, and any third component (e.g., powdered initiator) if separately packaged, are applied separately to the bleeding/wound site separately (simultaneously or sequentially) without prior formation of a powder mixture.

Figure 2:
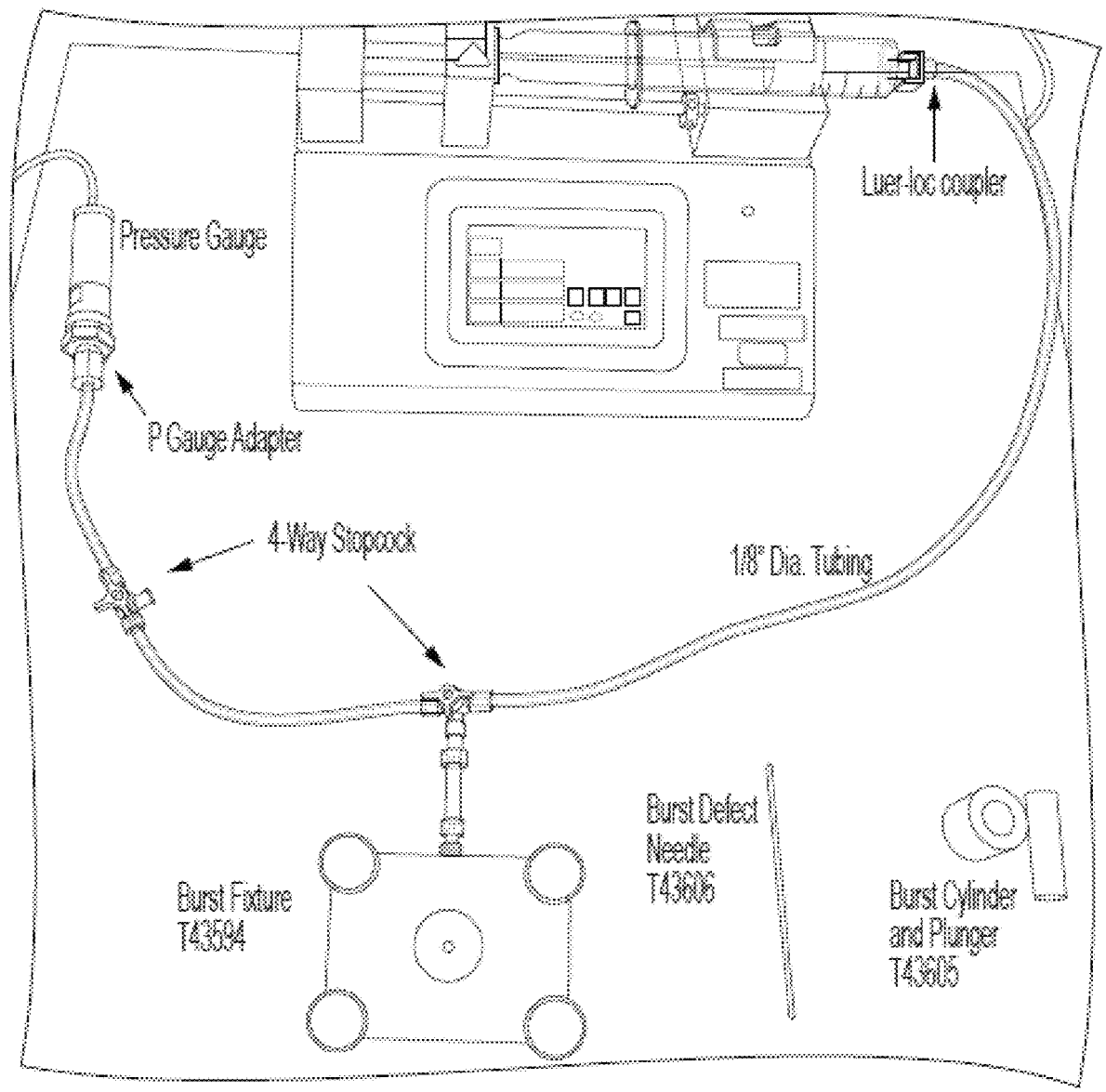
FIG. 2 shows, in accordance with certain embodiments, an experimental setup for measuring burst strength of hemostatic hydrogels.

According to certain embodiments, the adherence of the hemostatic hydrogel compositions described herein once formed upon crosslinking can be determined by a burst pressure model based on ASTM F2392-04, (the Standard Test Method for Surgical Sealants). According to certain embodiments, the test is designed to determine the pressure needed to rupture a sealant patch covering a simulated liquid leak and indirectly measure the adhesion property of the sealant to simulated tissue. Briefly, a pressure gauge, syringe pump, and burst fixture are assembled as shown in FIG. 2. The burst fixture is described in more detail in the ASTM F2392-04 standard protocol. All tubing is filled with 0.9% saline that has been dyed with a colored food dye (2-3 drops per L) so that no air bubbles are present in the tubing. Once the tubing is filled with the 0.9% saline, the line to all tubing is opened and the syringe is pushed until the saline starts to come out of the top hole of the burst fixture. Next, an appropriately sized piece of collagen is cut and then rinsed a minimum of three times in deionized water in a 500 mL beaker to remove glycerol. The collagen is cut into 2 inch wide strips and transferred to a new 500 mL beaker of deionized water to soak for a minimum of ten minutes. Next, the top of the burst fixture is removed and a single piece of collagen is placed over the opening of the burst fixture. The top of the burst fixture is then placed over the collagen and secured tightly. A burst defect needle (e.g., as shown in FIG. 2) is used to create a single defect in the center of the collagen by piercing the needle straight down the center of the hole in the burst fixture and straight back up. The burst cylinder (e.g., as shown in FIG. 2) is then placed on top of the fixture on top of the collagen. The dry powder composition is weighed in amount of 166 mg and poured into the burst cylinder. Next, 250 microliters of saline is pipetted into the cylinder directly onto the dry powder composition. Immediately after pipetting the saline, the burst plunger (e.g., as shown in FIG. 2) is placed into the burst cylinder on top of the hydrated composition. The hydrated composition is allowed to polymerize for 2.5 minutes. Next, the burst cylinder is removed by holding down the top of the burst plunger and pulling the cylinder straight up and off the top surface of the burst fixture. Once the cylinder has been released from the burst fixture, the plunger and cylinder are tilted and lifted to the side and then up and away from the polymerized composition. The sample is then inspected to ensure that removal of the cylinder and/or plunger did not disrupt the polymerized composition. A computer and appropriate software (e.g., Omega Digital Transducer Application, v. 2.3.0.300) is then used to record pressure readings. The polymerized composition is observed until the sample and/or substrate fails, a large pressure drop occurs, or the pressure plateaus for 30 seconds. Substrate failure occurs if the collagen rips separate from the material. Cohesive failure occurs if there is a defect through the polymerized composition. Cohesive and substrate failure occurs if the collagen and polymerized composition rip away from the defect site. Adhesive failure occurs if there is a defect between the material and the substrate interface. The above description for a burst pressure test method is a standard model. A "wet-field" burst pressure model may also be performed. The wet-field burst pressure model test method is identical to that of the standard model described above, except 250 μL of blood is allowed to pool over the defect in the collagen before pouring the dry powder into the burst cylinder.

In certain embodiments, the burst pressure of the hemostatic hydrogel measured by such test is greater than or equal to 10 mm Hg, greater than or equal to 50 mm Hg, greater than or equal to 100 mm Hg, greater than or equal to 150 mm Hg, greater than or equal to 200 mm Hg, greater than or equal to 250 mm Hg, greater than or equal to 300 mm Hg, or greater than or equal to 350 mm Hg. In certain embodiments, the burst pressure of the hemostatic hydrogel is less than or equal to 400 mm Hg, less than or equal to 350 mm Hg, less than or equal to 300 mm Hg, less than or equal to 250 mm Hg, less than or equal to 200 mm Hg, less than or equal to 150 mm Hg, less than or equal to 100 mm Hg, or less than or equal to 50 mm Hg. Combinations of the above recited ranges are also possible (e.g., the burst pressure of the hemostatic hydrogel is greater than or equal to 10 mm Hg and less than or equal to 350 mm Hg).

The hemostatic hydrogel (e.g., resulting from application of the dry powder composition to a bleeding/wound site) may have one or more viscoelastic properties that may be measured, in some embodiments, using an ElastoSens™ Bio 2 instrument from Rheolution, Inc. (Montreal, Quebec, Canada). In certain embodiments, for example, the ElastoSens™ Bio$^2$ instrument may be used to measure, for example, the shear elastic modulus (G'), the gelation rate (dG'/dt), and/or other relevant viscoelastic properties. In some embodiments, the shear elastic modulus (G') may be measured as a function of time as the dry powder composition hydrates with a fluid and polymerizes. It may be beneficial, in some embodiments, for the hemostatic hydrogel to have a sufficiently large shear elastic modulus to prevent or reduce elastic deformation of the hemostatic hydrogel after application to a bleeding/wound site. In certain embodiments, it may be beneficial for the hemostatic hydrogel to have a sufficiently fast gelation rate in order to quickly promote hemostasis when the dry powder composition is applied to a bleeding/wound site.

The ElastoSens™ Bio² instrument may be operated according to the following procedure. The ElastoSens™ Bio² instrument is first calibrated each day of use according to standard calibration procedures using the provided plastic calibration inserts and the associated instrument software (ElastoView™, version 18.12). After calibration, the sample holders are placed in an incubator at 37° C. for 20 minutes. The sample holders are then placed into the thermal chamber of the instrument and secured such that the sample holders cannot move. A new test is created using the associated instrument software. Next, 0.5 g of the dry powder composition is weighed and poured into sample holder. A single pipette or multi-channel pipette is then filled with the hydration fluid at 37° C., which is then released into the sample holder in a circular motion to ensure that all powder is evenly covered with the hydration fluid. Once sample loading is complete, the lid is of the instrument is closed and the test is started immediately. The results may be viewed in real time and/or exported from the software after completion.

In some embodiments, the maximum shear elastic modulus of the hemostatic hydrogel measured by such test is greater than or equal to 1000 Pa, greater than or equal to 2000 Pa, greater than or equal to 3000 Pa, greater than or equal to 4000 Pa, greater than or equal to 5000 Pa, greater than or equal to 7500 Pa, greater than or equal to 10000 Pa, greater than or equal to 11000 Pa, greater than or equal to 11000 Pa, greater than or equal to 12000 Pa, greater than or equal to 13000 Pa, greater than or equal to 14000 Pa, greater than or equal to 15000 Pa, greater than or equal to 16000, greater than or equal to 18,000, greater than or equal to 19000 Pa. or greater. In some embodiments, the maximum shear elastic modulus of the hemostatic hydrogel measured by such test is less than or equal to 20000 Pa, less than or equal to 19000 Pa, less than or equal to 18000 Pa, less than or equal to 17000 Pa, less than or equal to 16000 Pa, less than or equal to 15000 Pa, less than or equal to 14000 Pa, less than or equal to 13000 Pa, less than or equal to 12000 Pa, or less. Combinations of these ranges (e.g., greater than or equal to 1000 Pa and less than or equal to 20000 Pa) are possible.

The dry powder composition may have any of a variety of suitable gelation rates. As used herein, the term "gelation rate" refers to the speed at which hydrogel formation occurs over time, measured as (dG'/dt), which is the derivative of the shear elastic modulus over the derivative of time. In some embodiments, the maximum gelation rate measured of the hemostatic hydrogel measured by such test is greater than or equal to 50 Pa/s, greater than or equal to 60 Pa/s, greater than or equal to 75 Pa/s, greater than or equal to 90 Pa/s, greater than or equal to 100 Pa/s, greater than or equal to 150 Pa/s, greater than or equal to 200 Pa/s, greater than or equal to 225 Pa/s, greater than or equal to 250 Pa/s, or greater. In some embodiments, the maximum gelation rate measured of the hemostatic hydrogel measured by such test is less than or equal to 500 Pa/s, less than or equal to 400 Pa/s, less than or equal to 350 Pa/s, less than or equal to 300 Pa/s, less than or equal to 275 Pa/s, or less. Combinations of these ranges (e.g., greater than or equal to 50 Pals and less than or equal to 500 Pa/s) are possible.

According to certain embodiments, the hemostatic efficiency of the hemostatic hydrogel compositions can be determined by the number of cycles of manually applied pressure required to achieve hemostasis upon application of the dry powder mixture hemostats, as described above. In some embodiments, the number of pressure cycles required to achieve hemostasis upon application of the dry powder mixture hemostats is greater than or equal to 1 cycles, greater than or equal to 2 cycles, or greater than or equal to 3 cycles. According to certain embodiments, the number of pressure cycles required to achieve hemostasis upon application of the dry powder mixture hemostats is less than or equal to 4 cycles, less than or equal to 3 cycles, or less than or equal to 2 cycles. Combinations of these ranges are also possible (e.g., the number of pressure cycles required to achieve hemostasis upon application of the dry powder mixture hemostats is greater than or equal to 1 cycle and less than or equal to 3 cycles).

According to certain embodiments, the hemostatic efficiency of the hemostatic hydrogel compositions can also be determined by the time it takes to achieve hemostasis upon application of the dry powder mixture hemostats described herein. According to certain embodiments, the time it takes to achieve hemostasis upon application of the dry powder mixture is less than or equal to 2.5 minutes, less than or equal to 2.0 minutes, less than or equal to 1.5 minutes, less than or equal to 1.0 minute, less than or equal to 0.5 minutes, or less than or equal to 0.2 minutes.

In some embodiments, the hemostatic efficiency of the hemostatic hydrogel compositions can also be determined by the percent of treated defects achieving and maintaining hemostasis upon application of the dry powder mixture hemostats described herein. According to some embodiments, the percent of treated defects achieving and maintaining hemostasis upon application of the dry powder mixture is greater than or equal 70%, greater than or equal to 75%, greater than or equal to 80%, greater than or equal to 85%, greater than or equal to 90%, greater than or equal to 95%, or greater than or equal to 99%, or 100%.

In certain embodiments, the dry powder composition (e.g., dry powder mixture) may be prepared and/or admixed by any of a variety of suitable methods. For example, in some embodiments, the dry powder mixture may be prepared by ball milling (e.g., the dry powder mixture may be ground in a ball mill). In certain embodiments, the dry powder mixture may be prepared and/or admixed by grinding with a mortar and pestle. In some embodiments, the dry powder mixture is prepared and/or admixed using a rotary mixer.

According to certain embodiments, the dry powder composition (e.g., dry powder mixture) can be provided (e.g., packaged) as a sealed, admixed powder. For example, in some cases, the dry powder mixture is provided in a vial and/or ampoule (e.g., a flame-sealed vial and/or ampoule). In certain embodiments, the vial and/or ampoule containing the dry powder mixture may be attached to a sprayer that is capable of spraying the powder (e.g., onto a bleeding/wound site. In yet other embodiments. the dry powdered components could be formed into one or two component paste, putty or wax forms for use as crosslinking patching/filling materials—e.g., in bone bleeding applications.

In certain embodiments, it may be advantageous to reduce the physical contact between certain components of the composition prior to applying the dry powder mixture to a bleeding/wound site. In some embodiments, for example, physical contact between a functionalized polysaccharide (e.g., a polysaccharide functionalized with reactive groups such as the electrophilic groups described above) or a multifunctionalized polymeric composition (e.g., PEG(SS)2) and one or more components of the dry powdered composition, such as the optional crosslinking initiator (e.g., base or basic buffer), a functionalized polysaccharide (e.g., a polysaccharide functionalized with amine groups), a multifunctionalized polymer (e.g., PEG-diamine), or a protein may be reduced prior to applying the dry powder mixture to a bleeding/wound site. In some embodiments, for example, reducing the physical contact between the functionalized polysaccharide (e.g., a polysaccharide functionalized with reactive groups) or multifunctionalized polymeric composition and the crosslinking initiator may avoid chemical reactions between the two that have the potential to occur during storage, thereby increasing the overall shelf-life of the dry powder composition. As would be understood by a person of ordinary skill in the art, the functionalized polysaccharide (e.g., a polysaccharide functionalized with reactive groups) or multifunctionalized polymeric composition (e.g., PEG(SS)2), in some embodiments, is temperature and/or moisture sensitive. For example, in certain non-limiting embodiments, one or more ester bonds of the reactive groups or the multifunctionalized polymeric composition may be hydrolyzed in the presence of moisture (e.g., inherent in the atmosphere), which, in some embodiments, is facilitated and/or accelerated by the presence of the crosslinking initiator (e.g., base or basic buffer). Therefore, in certain embodiments, reducing the physical contact between the functionalized polysaccharide (e.g., a polysaccharide functionalized with reactive groups) or multifunctionalized polymeric composition and the crosslinking initiator may inhibit such hydrolysis from occurring during product storage, therefore increasing the overall shelf-life of the dry powder composition. It may be advantageous, in some embodiments, to reduce the physical contact between the functionalized polysaccharide or multifunctionalized polymeric composition and, for example, a protein (e.g., albumin) in order to prevent hydrolysis that may occur when the functionalized polysaccharide or multifunctionalized polymeric composition is in contact with inherent moisture present within the protein.

In certain embodiments, reducing the physical contact comprises lowering (or eliminating) the surface area (e.g., points of contact) between the functionalized polysaccharide (e.g., a polysaccharide functionalized with reactive groups) or multifunctionalized polymeric composition and one or more components of the dry powdered composition, such as the optional crosslinking initiator (e.g., base or basic buffer), a functionalized polysaccharide (e.g., a polysaccharide functionalized with amine groups), a multifunctionalized polymer (e.g., PEG-diamine), or a protein. In some embodiments involving a protein (e.g., albumin), the protein and/or crosslinking initiator may be manipulated such that there is limited physical contact between the functionalized polysaccharide (e.g., a polysaccharide functionalized with reactive groups) and the crosslinking initiator. According to some embodiments, for example, the protein may be roller compacted and/or granulated with the crosslinking initiator (e.g., base or basic buffer) prior to mixing with the functionalized polysaccharide (e.g., a polysaccharide functionalized with reactive groups). In other embodiments, the protein may be spray coated onto and/or over the crosslinking initiator (e.g., base or basic buffer) prior to mixing with the functionalized polysaccharide (e.g., a polysaccharide functionalized with reactive groups), such that, upon mixing, the functionalized polysaccharide (e.g., a polysaccharide functionalized with reactive groups) is substantially only in contact with the protein and not the crosslinking initiator during storage.

In certain embodiments, the functionalized polysaccharide or multifunctionalized polymeric composition may be manipulated such that there is limited physical contact between the functionalized polysaccharide or multifunctionalized polymeric composition and one or more other components of the dry powdered composition (e.g., the crosslinking initiator, functionalized polysaccharide, multifunctionalized polymer, and/or the protein). In some embodiments, for example, the functionalized polysaccharide or multifunctionalized polymeric composition may be coated with an inert material. The inert material may be, in some embodiments, a polymer. Any of a variety of suitable polymers that are suitable to coat and will not destroy or substantially degrade the reactivity of the functionalized polysaccharide or multifunctionalized polymeric composition may be employed. Suitable polymers include those polymers that are biodegradable, biocompatible, and/or soluble or water dispersible. In some embodiments, for example, such polymer is polyvinylpyrrolidone (PVP) or hydroxypropyl methylcellulose (HPMC).

The dry, powdered hemostatic compositions described herein may be provided in any of a variety of suitable forms. In some embodiments, dry, powdered hemostatic composition comprises at least a first dry powder and a second dry powder (and optionally a third dry powder, etc.). The first dry powder may comprise a first component described above. For example, in some embodiments, the first dry powder comprises a multifunctionalized polyalkylene oxide-based polymer comprising electrophilic groups (e.g., PEG(SS)2). In some embodiments, the first dry powder comprises a modified polysaccharide component comprising polysaccharide chains functionalized with electrophilic groups (e.g., hydrolyzed starch functionalized with electrophilic groups from group G). The second powder may comprise a second component described above. For example, the second dry powder may comprise a protein (e.g., albumin). In some embodiments, the second powder comprises a modified polysaccharide comprising polysaccharide chains functionalized with amine groups (e.g., hydrolyzed starch and/or hydroxyalkyl starch functionalized with amine groups).

In some embodiments, the dry, powdered hemostatic composition comprises at least one dry powder mixture. For example, the dry, powdered hemostatic composition may comprise a single dry powder that is a composite of some or all of the components described above (e.g., a single dry powder of particles of a nucleophilic component (e.g., albumin, polysaccharide functionalized with amine groups) coated an electrophilic component (e.g., PEG(SS)2, polysaccharide functionalized with electrophilic groups)). Such a powder of coated particles could be prepared, for example, by spray-coating using a solvent in which the components are unreactive (e.g., a non-aqueous solvent). In some embodiments, the dry, powdered composition comprises a dry powder mixture of multiple dry powders (e.g., the first dry powder and second dry powder). In other embodiments, the first dry powder and the second dry powder are provided as separated, unmixed powders (e.g., as packaged), and are combined prior to use (e.g., prior to applying to a bleeding/wound site).

In embodiments in which a crosslinking initiator (e.g., base or basic buffer) is present in the dry, powdered, hemostatic composition, the crosslinking initiator may be incorporated in any of a variety of suitable forms. For example, in some embodiments, the first dry powder comprises the crosslinking initiator. In some such embodiments, the composition comprises a first dry powder comprising a first component comprising a powder mixture of or composite particles of a reactive electrophilic compound (e.g., a multifunctionalized polyalkylene oxide-based polymer, a modified polysaccharide component comprising polysaccharide chains functionalized with electrophilic groups) and the crosslinking initiator (e.g., a base or basic buffer). In some embodiments, a first dry powder comprises particles of the reactive electrophilic compound spray-coated with crosslinking initiator, or vice versa. In some embodiments, the second dry powder comprises the crosslinking initiator. In some such embodiments, the composition comprises a second dry powder comprising a second component comprising a power mixture of or composite particles of a reactive nucleophilic compound (e.g., a protein such as albumin, a modified polysaccharide component comprising polysaccharide chains functionalized with amine groups) and the crosslinking initiator (e.g., a base or basic buffer). In some embodiments, a second dry powder comprises particles of the reactive nucleophilic compound spray-coated with crosslinking initiator, or vice versa.

In some embodiments, the crosslinking initiator is present as a powder other than that of the reactive electrophilic (e.g., PEG(SS)2, functionalized polysaccharide) or nucleophilic (e.g., albumin, functionalized polysaccharide) compounds above. For example, in some embodiments, the dry, powdered hemostatic composition comprises a first dry powder comprising the first component, a second dry powder comprising a reactive nucleophilic compound (e.g., a protein such as albumin, polysaccharide chains functionalized with amine groups), and a third dry powder comprising the crosslinking initiator (e.g., a base or basic buffer). The first, second, and third dry powders may be packaged separately or combined as a dry powder mixture. In some embodiments, the dry, powdered hemostatic composition comprises a single dry powder comprising composite particles of a reactive nucleophilic compound, a crosslinking initiator, and a reactive electrophilic compound. For example, the dry, powdered hemostatic composition comprises a single dry powder of particles of a nucleophilic component (e.g., albumin, polysaccharide functionalized with amine groups) coated with a crosslinking initiator (e.g., a base or basic buffer), which is in turn coated with an electrophilic component (e.g., PEG(SS)2, polysaccharide functionalized with electrophilic groups)). Other configurations of the components are also possible. Such a powder of coated particles could be prepared, for example, by spray-coating using a solvent in which the components are unreactive (e.g., a non-aqueous solvent).

In another aspect, hemostatic articles are described. In certain cases, a hemostatic article comprises a powdered hemostatic composition (e.g., any of the reactive, dry, powdered hemostatic compositions described herein) used with, in contact with, or otherwise associated with a tamponade device. Applying a reactive, dry, powdered hemostatic composition to a bleeding wound using a tamponade may further reduce or stop bleeding at a bleeding/wound site upon formation of a hydrogel due to cross-linking of components of the hemostatic composition compared to use of the dry, powdered hemostatic compositions alone. The presence of a tamponade can, in some cases, improve the efficacy of dry, powdered hemostatic compositions in applications where high flow bleeding occurs. In some embodiments, the tamponade is a biodegradable tamponade. Combining a reactive, dry, powdered hemostatic composition with a biodegradable tamponade can, in some cases, provide for a hemostatic device that can be easily applied to a wound or bleeding site while improving certain performance aspects of the reactive hemostats. For example, applying a dry, powdered hemostatic composition in contact with a biodegradable tamponade can, in some cases, mitigate adhesion between polymerized hemostatic composition and, for example, a non-biodegradable applicator or material otherwise used to contact the hemostatic composition, such as gauze.

In some, but not necessarily all cases, the reactive, dry, powdered hemostatic composition that is used with (e.g., is in contact with) the tamponade is one of the dry, powdered hemostatic compositions described above. For example, in some embodiments, a dry, powdered hemostatic composition comprising a first component comprising a multifunctionalized polymer (e.g., PEG(SS)2) and a second component comprising a protein (e.g., albumin) is in contact with the tamponade. As another non-limiting example, in certain cases, a dry, powdered hemostatic composition comprising a first component comprising a modified polysaccharide functionalized with electrophilic groups capable of reacting with amines (e.g., hydrolyzed, uncrosslinked starch and/or microporous microspheres functionalized with electrophilic groups) and a second component comprising a modified polysaccharide functionalized with amine groups (e.g., hydrolyzed, uncrosslinked starch and/or microporous microspheres functionalized with amino acids such as glycine or dimethyl glycine) is in contact with the tamponade.

The tamponade can comprise any of a variety of suitable materials. In certain cases, the tamponade is in the form of a foam having any suitable form factor or aspect ratio. For example, the tamponade may be in the form of a sheet or layer. In some embodiments, the tamponade is in the form of a foam that is in the form of a sheet or a layer. In some cases, the tamponade is or comprises collagen (e.g., collagen foam). One such collagen-containing tamponade is an Ultrafoam™ tamponade. In other cases, the tamponade is or comprises gelatin (e.g., a gelatin foam). One such gelatin-containing tamponade is Gelfoam™. In certain embodiments, the tamponade comprises carboxymethylcellulose (CMC). In some embodiments, the tamponade comprises a polysaccharide. As an example, in some embodiments, the tamponade comprises a starch foam. In certain embodiments, the starch foam may be degradable, dispersible, and/or soluble.

The reactive, dry, powdered hemostatic composition in contact with the tamponade (e.g., the Ultrafoam™ tamponade, the tamponade comprising a starch foam, etc.) may be located relatively close to the surface of the tamponade. For example, in some cases the reactive, dry, powdered hemostatic composition is in contact predominately with an external surface of the tamponade. In certain embodiments, the reactive, dry, powdered hemostatic composition is contained within the tamponade (e.g., the tamponade is impregnated with the reactive, dry, powdered hemostatic composition).

In some embodiments, the reactive, dry, powdered hemostatic composition is applied to a bleeding/wound site at a different time than is the tamponade. For example, in some embodiments, a dry, powdered hemostatic composition is applied to a bleeding/wound site, and subsequently the tamponade is applied to the bleeding/wound site (optionally with an application of steady or intermittent manual pressure to the tamponade). However, in certain cases, the reactive, dry, powdered hemostatic composition and the tamponade (e.g., containing the dry, powdered hemostatic composition) are applied to the bleeding/site at the same time.

U.S. Provisional Patent Application No. 63/047,892, filed Jul. 2, 2020, and entitled "Reactive Polysaccharide-Based Hemostatic Agent," and U.S. Provisional Patent Application No. 63/047,889, filed Jul. 2, 2020, and entitled "Flowable Hemostatic Suspension," are each incorporated herein by reference in its entirety for all purposes.

Example 1

The following example describes the functionalization of a starch with amine groups. A solution of Hespan®, which contained 6% hydroxyethyl starch (having a weight-averaged molecular weight of $M_w$=450-800 kDa with 75 hydroxyethyl groups for every 100 glucose units) was mixed with 3-amino triethoxysilane (APTES) to form a reaction mixture for the functionalization reaction. The reaction was carried out at room temperature. The reaction mixtures were formed by adding 6 mL of APTES to 20 mL of Hespan solution (a volume ratio of Hespan:APTES of 1:0.3). The pH of the reaction mixture was adjusted with glacial acetic acid. In one sample, the addition of 4.3 mL of glacial acetic acid to the reaction mixture adjusted the pH to a value of 4. In another sample, the addition of 1.2 mL of glacial acetic acid to the reaction mixture adjusted the pH to a value of 7. In another sample, the addition of 1.0 mL of glacial acetic acid to the reaction mixture adjusted the pH to a value of 9. The respective reaction mixtures were left to react overnight. After the reactions were completed, ethanol was added at each sample at a volume of 5 times the reaction mixture volume. For example, 150 mL of 100% ethanol was added to the reaction mixture that had a pH of 4. The resulting solids were then collected from the resulting suspensions by centrifuging the samples at 1,000 G for 5 minutes. The collected tacky solids were washed with 95% ethanol and then dried for 3 hours at a temperature of 110° C. After the drying step, the samples were subjected to three additional cycles of being washed with 95% ethanol and then centrifuged. The resulting solids were then dried for 30 minutes at a temperature of 110° C. directly prior to use.

The extent of amine functionalization achieved for the functionalized hydroxyethyl starch of the collected solids above was characterized using a 2,4,6-trinitrobenzene sulfonic acid (TNBSA) assay. The TNBSA assay determined the number of free amino groups present in the functionalized hydroxyethyl starch. The functionalized hydroxyethyl starch was dried to remove moisture, and a test solution was form by dissolving 30 mg of the resulting dried powder was in 10 mL Of 0.1 M borate ($BO_3^-$) buffer solution, which had a pH of 9.3. In a 96-well plate, 100 µL of the test solution was combined with 20 µL of 3.75 mM TNBSA solution and incubated at room temperature for 30 minutes. The absorbance of the incubated solution was monitored at 420 nm. The amine content of the functionalized hydroxyethyl starch was determined using a glycine calibration curve. It was observed that the amine content of the functionalized hydroxyethyl starch ranged from 214-254 µmol of amine per gram of powder of the functionalized hydroxyethyl starch.

Example 2

The following example describes the measured crosslink time of a dry powder composition containing the functionalized hydroxyethyl starch of Example 1, PEG(SS)2, and sodium bicarbonate. The measured crosslink time was measured as described above using saline. The dry powder composition formed a cross-linked hydrogel in 60-90 seconds when added to the saline.

Example 3

The following example describes the functionalization of hydrolyzed starch with amine groups via an amino acid ligand. The hydrolyzed starch (Dextrose Equivalent of 3.5 and a weight-averaged molecular weight of 60 kDa) was functionalized with glycine with a tert-butoxycarbonyl protecting group (Boc-Gly) for a target modification of 2.2 Boc-Gly esters per glucose repeating unit of the hydrolyzed starch. The procedure was as follows. 192.7 g of Boc-Gly was added to 400 mL of anhydrous dimethylformamide (DMF). The solution temperature was maintained at 60° C. 187.3 g of carbonyl diimidazole (CDI) was added to the Boc-Gly/DMF solution and the CDI container was rinsed with an additional 50 mL of DMF. The reaction proceeded for 1.5 hours at 60° C.

After completion of the CDI/Boc-Gly reaction, 90 g of hydrolyzed starch was added to the reaction mixture, and the container was rinsed with an additional 50 mL of DMF. The reaction then proceeded for 4 hours at 60° C. and then was allowed to cool slowly overnight at 10° C.

After the cooling step overnight, 1 L of water was added to the solution. The reaction mixture and the water were mixed for 1 hour, and the resulting precipitate was allowed to settle overnight. After overnight settling, the supernatant was removed by vacuum filtration. The solid precipitate was rinsed with 100 mL of additional water and then transferred back to the reaction vessel for another wash cycle. 1.5 L of water was added and mixed for an hour. The solid precipitate was collected by vacuum filtration and rinsed with 100 mL of additional water. This rinse process was repeated for a total of five washes. Then, the collected hydrolyzed starch-Gly-Boc precipitate was dried in a vacuum oven at 60° C. for 48 hours. The hydrolyzed starch-Gly-Boc was characterized by NMR (Methanol-d4) and showed a large signal corresponding to the Boc group. A very small amount of DMF and imidazole was also detected.

The hydrolyzed starch-Gly-Boc product was deprotected to remove the Boc group, resulting in the glycine comprising a free amino group. The resulting product was denoted hydrolyzed starch-Gly-$NH_2$. The deprotection procedure was as follows. 100 g of hydrolyzed starch-Gly-Boc was added to 900 mL of anhydrous dichloromethane (DCM) and mixed for 0.5 hour at room temperature. Then, 100 mL of trifluoroacetic acid (TFA) was added to the mixture, mixed for 3 hours, and cooled using an ice bath. 190 mL of triethylamine was added and mixed for 0.5 hour while cooling with ice.

The hydrolyzed starch-Gly-$NH_2$ product was precipitated by adding 1 L of ethanol, mixing for 1 hour, and allowing to settle overnight in a refrigerator. The solid precipitate was then collected by vacuum filtration and then washed 5 times by adding 500 mL of ethanol and applying suction to remove the liquid. The hydrolyzed starch-Gly-$NH_2$ precipitate was dried in a vacuum oven at 55° C. for approximately 72 hours.

The extent of amine functionalization of the hydrolyzed starch was determined using elemental analysis. Based on the nitrogen content, there were approximately 1.1 amines per glucose repeating unit of the hydrolyzed starch.

Example 4

This example describes the functionalization of a starch with amine groups. A solution of Hespan®, which contained 6% hydroxyethyl starch (HES) (having a weight-averaged molecular weight of $M_w$=450-800 kDa with 75 hydroxyethyl groups for every 100 glucose units) was mixed with 3-amino triethoxysilane (APTES) to form a reaction mixture for the functionalization reaction. The reaction was carried out at room temperature. The reaction mixtures were formed by adding 50 mL of APTES to 167 mL of Hespan solution (a volume ratio of Hespan:APTES of 1:0.3). The pH of the reaction mixture was adjusted to pH 4 by adding 35 mL of glacial acetic acid. The respective reaction mixtures were left to react for 24 hours, with aliquots removed at various time intervals for characterization. After the reactions were completed, 167 mL of acetonitrile was added to the reaction mixture, and the solvent was then removed by rotary evaporation. The acetonitrile addition and rotary evaporation cycles was repeated a total of four times, after which a viscous liquid remained. The viscous liquid was then added to 800 mL of rapidly stirring ethanol to induce precipitation. The precipitate was recovered by filtration and subjected to three cycles of washing with 150 mL of 100% ethanol. The washed crude solid was then subjected to an annealing step in a 110° C. environment for 3 hours. Finally, the annealed solid was subjected to three cycles of washing with 150 mL of 100% ethanol and dried overnight at room temperature in a vacuum desiccator. A mass recovery percentage of 162% was recorded.

Figure 3:
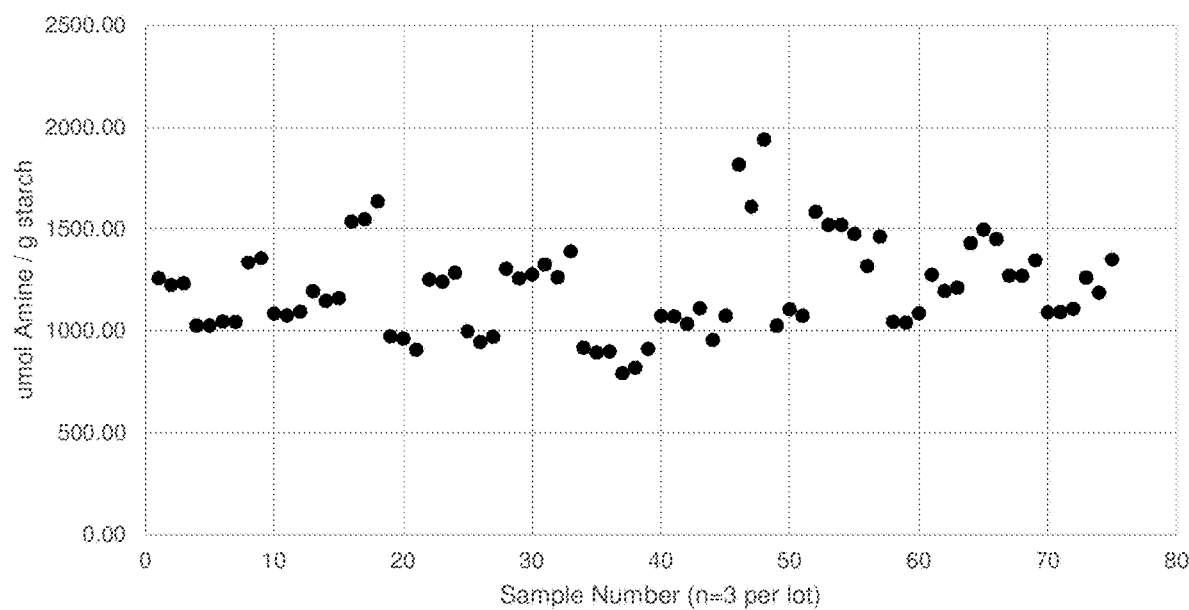
FIG. 3 shows, in accordance with certain embodiments, measured amine density of an exemplary functionalized polysaccharide component.

The extent of amine functionalization achieved for the functionalized hydroxyethyl starch of the collected solids above was characterized using a 2,4,6-trinitrobenzene sulfonic acid (TNBSA) assay. The TNBSA assay determined the number of free amino groups present in the functionalized hydroxyethyl starch. The functionalized hydroxyethyl starch was dried to remove moisture, and a test solution was formed by dissolving 30 mg of the resulting dried powder in 10 mL of 0.1 M borate ($BO_3^-$) buffer solution, which had a pH of 9.3. In a 96-well plate, 100 μL of the test solution was combined with 20 μL of 3.75 mM TNBSA solution and incubated at room temperature for 30 minutes. The absorbance of the incubated solution was monitored at 420 nm. The amine content of the functionalized hydroxyethyl starch was determined using a glycine calibration curve. For 200 g of amine-functionalized hydroxyethyl starch measured via multiple batches (~75 samples), it was observed that the amine content of the functionalized hydroxyethyl starch ranged from ~800 to 2,000 μmol of amine per gram of powder of the functionalized hydroxyethyl starch. FIG. 3 shows batch-to-batch variability of amine functionalization for samples synthesized according to this example. The TNBSA assay indicated that in a representative sample, 8.34% of hydroxy groups were functionalized by APTES. It was also observed that longer reaction times between the hydroxyethyl starch and the APTES were correlated with higher amine contents as measured by the TNBSA assay.

Example 5

This example describes the measured crosslink time, gel strength, burst strength, and gelation time of a dry powder composition containing the functionalized hydroxyethyl starch of Example 4, PEG(SS)2, and sodium bicarbonate.

The functionalized hydroxyethyl starch used for these measurements was a dry powder having a bulk density of 0.39±0.01 g/mL, a tapped density of 0.46±0.01 g/mL, a Hausner ratio of 1.18, a D10 of 101 micrometers, a D50 of 306 micrometers, and a D90 of 584 micrometer.

Two formulations of functionalized hydroxyethyl starch, PEG(SS)2, and sodium bicarbonate were tested, as described in Table 1 below.

TABLE 1

| Functionalized starch and PEG(SS)2 formulations. | | | | |
|---|---|---|---|---|
| Sample | HES-amine | PEG(SS)2 | $NaHCO_3$ | Total weight |
| 1 | 12.2 g | 4.8 g | 3.0 g | 20 g |
| 2 | 9.12 g | 4.76 g | 6.12 g | 20 g |

The crosslink time of the resulting crosslinked hydrogels was measured according to the stir bar procedure described above. The burst strength of the resulting crosslinked hydrogels was measured according to the burst pressure model based on ASTM F2392-04 described above, using saline. The gel shear elastic modulus (G'), gelation rate, and other viscoelastic properties of the resulting crosslinked hydrogels were measured as function of time upon initiation of crosslinking, according to the procedure described above for the ElastoSens™ $Bio^2$ instrument. The maximum observed shear elastic modulus (G'max) was also recorded. Table 2 summarizes the crosslinking, burst strength, and viscoelastic properties of the hydrogels formed from Samples 1 and 2.

TABLE 2

| Crosslink time, burst strength, and viscoelastic properties of functionalized starch and PEG(SS)2 formulations. Measurements shown as average ± standard deviation | | | | | | | | |
|---|---|---|---|---|---|---|---|---|
| Sample | Crosslink Time (s) | Burst Strength (mmHg) | G'max (Pa) | Time of G'max (s) | Max. Gelation Rate (Pa/s) | Time of Max. Gelation Rate | G' at 150 s (Pa) | Time to reach 5000 P (s) |
| 1 | 38 ± 3 | 193.5 ± 30.4 | 11693.8 ± 1606.2 | 122.6 ± 75.7 | 268.6 ± 49.1 | 30.9 ± 5.3 | 9531.7 ± 1068.3 | 24.3 ± 6.0 |
| 2 | 39 ± 3 | 191.2 ± 35.2 | 10939.2 ± 2016.3 | 163.5 ± 72.4 | 278.0 ± 36.4 | 33.6 ± 14.8 | 9764.3 ± 1107.0 | 27.9 ± 2.6 |

Example 6

This example describes the application of an amine-functionalized starch and PEG(SS)2-based dry powder mixture in porcine spleen biopsy defect models. The dry powder mixtures was prepared by mixing the amine-functionalized hydroxyethyl starch (HES-amine) as prepared in Example 4 with PEG(SS)2 and sodium bicarbonate in a mass ratio of 61% HES-amine, 24% PEG(SS)2, and 15% sodium bicarbonate. A control composition for comparative purposes was prepared by mixing bovine serum albumin (BSA), PEG(SS)2, and sodium bicarbonate in a mass ratio of 61.5% BSA, 22% PEG(SS)2, and 16.5% sodium bicarbonate. The defect models included both standard and modified wet field bleeding models, as described as follows. Briefly, a 10 mm diameter biopsy defect to a depth of about 5 mm was made in the spleen. Next, 0.5 g of the dry powder mixture was applied to the defect and a 3 cm×3 cm piece of Ultrafoam was placed on top of the powder to prevent it from sticking to the gauze used for application of pressure. Cessation of bleeding was assessed after thirty second tamponade or pressure cycles. The wet-field measurement differed from the standard defect model in that in the wet field model, the material was applied to an actively bleeding site, instead of blotting the defect dry prior to placement. In the wet field model, the defect was allowed to fill with blood after the defect was made and prior to application of the dry powder. Table 3 shows results of the standard and wet field measurements for the HES-amine formulation as well as the comparative formulation of albumin and PEG(SS)2.

TABLE 3

Hemostatic efficacy of PEG(SS)2-based dry powder mixture in a porcine spleen biopsy defect model.

| Group | Description | #of Defects Treated | # of Pressure Cycles Required to Achieve Hemostasis (mean ± std. dev.) | % of Defects Achieving and Maintaining Hemostasis (2 min. Observation) |
|---|---|---|---|---|
| Standard Model | | | | |
| HES-Amine + PEG(SS)2 powder mixture + Ultrafoam | powder + foam sponge | 3* | 3.3 ± 2.5 | 67 |
| Albumin + PEG(SS)2 + Foam Tamponade | powder + foam sponge | 4 | 2.0 ± 2.0 | 100 |
| Wet Field Model | | | | |
| HES-Amine + PEG(SS)2 powder mixture + Ultrafoam | powder + foam sponge | 2 | 1.0 ± 0.0 | 100 |
| Albumin + PEG(SS)2 + Foam Tamponade | powder + foam sponge | 5 | 1.8 ± 1.8 | 100 |

* Outlier removed: a significant amount of powder was carried away by high flow arterial bleeding during application It was observed that the crosslinking and tissues adherence for the HES-amine+PEG(SS)2 dry powder mixtures was similar to that observed with albumin+PEG(SS)2 dry powder mixtures.

Example 7

This example describes the functionalization of a starch with amine groups. An aqueous solution of hydroxyethyl starch was provided by dissolving 3.6 g of hydroxyethyl starch (HES; BOC Sciences, Shirley, N.Y.) having a weight average molecular weight of 592 kDa and MS 0.79 in 60 mL of deionized water. APTES (17.85 mL) was added to the aqueous solution of HES while stirring. The pH of the resulting solution was immediately adjusted to 4 by adding glacial acetic acid dropwise. The reaction mixture was left to stir overnight under a nitrogen gas atmosphere. After the overnight reaction, 60 mL of acetonitrile was added to reaction mixture and the combined mixture underwent evaporation to remove the liquid via rotary evaporation under a reduced pressure and using a water bath of 50° C. Another 60 mL of acetonitrile was added to the dried crude product and another round of rotary evaporation was performed. A total of 3-6 cycles of acetonitrile addition and evaporation were performed. When the solution reached a liquid-gel state, the liquid-gel crude product was slowly poured into to 300 mL of stirring 100% ethanol to induce precipitation of the HES-APTES. The HES-APTES crude solid was removed via filtration and washed with 50 mL of 100% ethanol three times. The collected HES-APTES crude solid was dried for 3 hours at 110° C. The dried HES-APTES solid was then crushed into a powder and suspended in 50 mL of 100% ethanol. The suspended solids were then filtered and washed twice with 50 mL of 100% ethanol. The filtered solids were dried for an additional 30 minutes at 110° C. to afford the final HES-APTES product.

Example 8

This example describes the functionalization of a starch with electrophilic groups. Hydrolyzed starch was provided as Glucidex® Maltodextrin 12 (Glx12) from Roquette America, Inc. (Keokuk, Iowa). To functionalize some of the hydroxy groups of the maltodextrin to succinic acid, 25 g of the Glx12, 6.3 g of succinic anhydride (SA, Sigma), and 7.7 g of dimethylaminopyridine (Sigma) were weighted and dissolved in 100 mL of dimethylsulfoxide (DMSO, Sigma) in a 300 mL round-bottom flask. The reaction was stirred for 24 hours at 40° C. The following day, 900 mL of an ethanol/ether (60/40) mixture was added to the reaction mixture to induce precipitation. The precipitated mixture was filtered and wash with ethanol. The filtered material (Glx12-SA) was dried overnight in a vacuum oven at room temperature.

Figure 4:
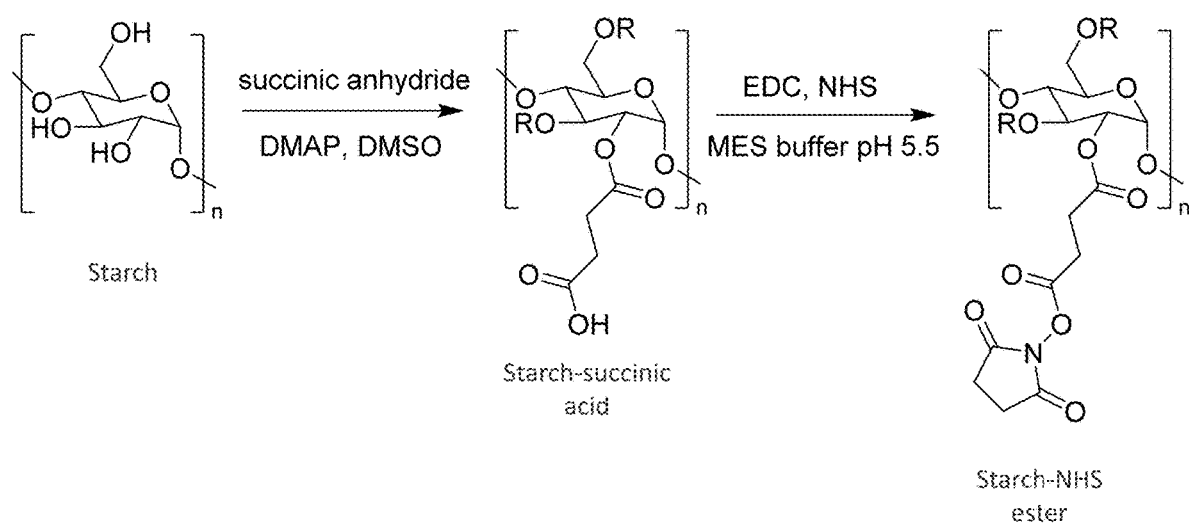
FIG. 4 shows, in accordance with certain embodiments, a reaction scheme for functionalizing a polysaccharide with an electrophilic group.

To functionalize the succinic acid groups of the Glx12-SA to N-oxysulfosuccinimidyl groups (sNHS groups), 5 g of Glx12-SA was dissolved in 20-25 mL of 2-(N morpholino) ethanesulfonic acid (MES) buffer (pH 5.5, Sigma) in a 30 mL scintillation vial and stirred at room temperature prior to adding 2.7 g of N-hydroxysulfosuccinimide (Thermo Fisher Scientific, Waltham, Mass.) and 2.4 g of 1-ethyl-3-(-3-dimethylaminopropyl) carbodiimide hydrochloride (EDC, Thermo Fisher Scientific, Waltham, Mass.) to the reaction mixture. After 45 minutes, the reaction mixture was poured into 200 mL ethanol to induce precipitation. The precipitated material was gently pelleted by centrifuging at 500 G for 20 seconds. The supernatant was removed and the material was washed with ethanol and re-pelleted. The resulting solid was dried overnight in a vacuum oven at room temperature. FIG. 4 shows the overall reaction scheme. Successful synthesis of the product was confirmed by $^1$H NMR.

Example 9

This example describes the measured crosslink time of a dry powder composition containing the starch with electrophilic groups of Example 8 and a multifunctionalized polymer comprising amine groups. Saline solution was added to a three-component dry powder mixture of the Glx12-sNHS from Example 8, polyethylene glycol diamine (PEG-diamine, Sigma Aldrich, Catalog #P9906), and sodium borate (NaBO$_3$, Millipore). The Glx12-sNHS, PEG-diamine, and sodium borate were present in the three-component dry power mixture in an 80:40:50 mass ratio, respectively. In one set of experiments, the crosslinking measurement was carried out as described in Example 2 or 5, and an average crosslink time of 70±9 s was measured. It was observed that the Glx12-sNHS powder tended to float in the saline solution, likely due to the small particle size and/or lower density. In another set of experiments, the crosslinking protocol described in Example 2 or 5 was modified to include a step of vortexing the solution for 3 seconds prior to stirring with the stir bar. Using this modified vortexing protocol, an average crosslink time of 19±6 s was measured.

Example 10

This example describes preparation of a relatively dense powder of the starch with electrophilic groups of Example 8. In this example, the Glx12-sNHS was synthesized in a reaction mixture as described in Example 8, but the reaction mixture was split into two batches for precipitation. A first batch was precipitated with ethanol as described in Example 8. A second batch was precipitated using a 50:50 mixture of ethanol and diethyl ether. The precipitated Glx12-sNHS material was then washed, dried overnight, manually ground, and sieved. The recovered powder material precipitated using ethanol had a tapped density of ~0.4 g/mL, while the recovered powder material precipitated using the 50:50 ethanol:diethyl ether had an increased tapped density of ~0.6 g/mL.

Example 11

This example describes the measured crosslink time of a dry powder composition containing a starch with an increased extent of functionalization with electrophilic groups and a multifunctionalized polymer comprising amine groups. Glx12-sNHS was synthesized as described in Example 8, with two modifications: (1) instead of a 1.0:0.15 molar ratio of starch hydroxy groups to sNHS groups in the reaction mixture, ratios of 1.0:0.30 and 1.0:0.45 were employed to test for increased functionalization, and (2) precipitation was performed using 50:50 ethanol:diethyl ether instead of ethanol. It was observed that this precipitation method using 50:50 ethanol:diethyl ether yielded Glx12-sNHS powder with greater density than Glx12-sNHS precipitated using ethanol only. The greater density allowed the Glx12-sNHS powder of this example to be used in crosslinking tests without vortexing the sample (as was done in Example 8). Crosslinking measurements with PEG-diamine and sodium borate were performed using the protocol described above in Example 5 using saline in one set of experiments and blood in another. Results are shown in Table 4.

TABLE 4

Crosslinking time for electrophile-functionalized starch with PEG-diamine.

| —OH:sNHS molar ratio | Crosslinking Solution | Crosslinking Time (s) |
|---|---|---|
| 1:0:0.3 | Saline | 48 ± 5 |
|  | Blood | 48 ± 8 |
| 1.0:0.45 | Saline | 36 ± 4 |
|  | Blood | 27 ± 5 |

The data in Table 4 indicate that increased functionalization leads to reduced crosslinking time, and similar crosslinking times are observed in saline and blood solutions. In the blood samples, the stir bar slowed down but did not stop completely.

Example 12

This example describes the measured crosslink time of a dry powder composition containing the starch with amine groups of Example 4 and a starch with electrophilic groups of Example 8. Glx12-sNHS was synthesized as described in Example 8 except precipitation was performed using 50:50 ethanol:diethyl ether instead of ethanol. Crosslinking measurements with a dry powder mixture of HES-amine, Glx12-sNHS, and sodium borate in an 80:80:50 mass ratio were performed using the protocol described above in Example 2 or 5, using blood. An average crosslinking time of 21.8 s±6.0 was observed. Complete gelation and good flow in blood was observed for all five samples tested. The gelation caused the stir bar to slow.

Example 13

This example describes the measured crosslink time of a dry powder composition containing the starch with electrophilic groups of Example 8 and albumin. Glx12-sNHS was synthesized as described in Example 8 except precipitation was performed using 50:50 ethanol:diethyl ether instead of ethanol. Crosslinking measurements with a dry powder mixture of Glx12-sNHS, human serum albumin (HSA), and sodium borate in a 80:80:50 mass ratio were performed using the protocol described above in Example 2 or 5, using blood. An average crosslinking time of 18.2 s±4.0 was observed. Complete gelation in blood was observed for all five samples tested. In three of the five samples the resulting gel stopped the stir bar, while in the other two samples the stir bar was able to continuously stir because the gel was formed above the stir bar in the vial.

Example 14

This example describes the measured wet-field burst pressure of a hydrogel formed from a dry powder composition containing the starch with electrophilic groups of Example 8 and a variety of nucleophilic polymers. Glx12-sNHS was synthesized as described in Example 8, with two modifications: (1) instead of only 1.0:0.15 molar ratio of starch hydroxy groups to sNHS groups in the reaction mixture, batches having ratios of 1.0:0.15, 1.0:0.30 and 1.0:0.45 were employed to test for the effect of increased functionalization, and (2) precipitation was performed using 50:50 ethanol:diethyl ether instead of ethanol. The nucleophilic polymers tested were the following: PEG-diamine HCl (JenKem Technology USA Inc.), the starch with amine groups of Example 4, and the human serum albumin of Example 13. The wet-field burst pressure method based on ASTM F2392-04 was performed as described above. Table 5 shows wet-field burst pressure measurements for hydrogels formed from dry powders containing electrophile-functionalized starch with the nucleophilic polymers. The powder mixtures also contained either potassium tetraborate tetrahydrate ($K_2B_4O_7 \cdot 4H_2O$, Alfa Aesar catalog #39435) or disodium hydrogen phosphate ($Na_2HPO_4$, Fisher catalog #S374-500)

TABLE 5

Wet-field burst pressure measurements for hydrogels formed from dry powders containing electrophile-functionalized starch with various nucleophilic polymers.

| Sample | —OH:sNHS molar ratio of starch electrophile batch | Mass of electrophilic component in powder (mg) | Nucleophilic component | Mass of nucleophilic component in powder (mg) | Potassium tetraborate tetrahydrate mass in powder (mg) | Disodium hydrogen phosphate mass in powder (mg) | Max Pressure (Avg. ± std. deviation) (mmHg) |
|---|---|---|---|---|---|---|---|
| 1 | 1:0:0.15 | 80 | PEG-diamine HCl | 40 | 50 | 0 | 141.7 ± 54.1 |
| 2 | 1:0:0.3 | 80 | PEG-diamine HCl | 40 | 50 | 0 | 124.3 ± 67.9 |
| 3 | 1.0:0.45 | 80 | PEG-diamine HCl | 40 | 50 | 0 | 179.5 ± 68.9 |
| 4 | 1:0:0.15 | 80 | HES-amine | 40 | 50 | 0 | 101.4 ± 47.5 |
| 5 | 1:0:0.15 | 80 | Human serum albumin | 40 | 50 | 0 | 111.1 ± 59.6 |
| 6 | 1:0:0.15 | 80 | PEG-diamine HCl | 40 | 0 | 50 | 131 ± 51 |

The results in Table 5 indicate that hydrogels formed from each dry powder formulation comprising a starch functionalized with electrophilic groups have sufficient burst strengths for hemostatic applications, and are sufficiently strong to serve as vascular sealants.

Example 15

This example describes the application of dry powder mixtures of starch functionalized with electrophilic groups and various nucleophilic polymers in porcine spleen biopsy defect models.

The dry powder mixtures were prepared by mixing the sNHS-functionalized maltodextrin (Glx12-sNHS) synthesized using the protocols described in Examples 8 and 10 with either PEG-diamine.HCl salt or human serum albumin (HSA). Potassium tetraborate tetrahydrate ($K_2B_4O_7 \cdot 4H_2O$; Alfa Aesar catalog #39435) or disodium hydrogen phosphate ($Na_2HPO_4$, Fisher catalog #S374-500) was used as the base for preparing these mixtures. The mass ratio of Glx12-sNHS, PEG-diamine.HCl and base in the dry powder mixture was 80:40:50 and that of Glx12-sNHS, HSA and base was 80:80:50 in its respective dry powder mixture. A wet field bleeding model, as described in Example 6, was employed. Table 6 shows results of the wet field measurements using the aforementioned samples.

TABLE 6

Hemostatic efficacy of electrophile-functionalized starch-based dry powder mixtures in a porcine spleen biopsy defect model.

| Group Wet Field Model | Description | #of Defects Treated | # of Pressure Cycles Required to Achieve Hemostasis (mean ± std. dev.) | % of Defects Achieving and Maintaining Hemostasis (2 min. Observation) |
|---|---|---|---|---|
| Glx12-sNHS + PEG-diamine•HCl + potassium tetraborate + Foam Tamponade | powder + foam sponge | 14 | 1.9 ± 0.7 | 100 |
| Glx12-sNHS + PEG-diamine•HCl + disodium hydrogen phosphate + Foam Tamponade | powder + foam sponge | 7 | 2.4 ± 2.1 | 100 |
| Glx12-sNHS + HSA + potassium tetraborate + Foam Tamponade | powder + foam sponge | 5 | 3.3 ± 3.8 | 80 |

It was observed that the crosslinking and tissues adherence for the Glx12-sNHS+PEG-diamine.HCl dry powder mixtures was similar to that observed with albumin+PEG (SS)2 dry powder mixtures.

Example 16

This example describes an alternate method of coupling sNHS groups to Glx12-SA synthesized in Example 8, and crosslinking experiments with the resulting product. Specifically, a non-polar carbodiimide (e.g., N,N'-Diisopropylcarbodiimide, DIC, Sigma catalog #D125407 or N,N'-Dicyclohexylcarbodiimide, DCC, Sigma catalog #D80002) was dissolved in an organic solvent instead of EDC being dissolved in an aqueous reaction mixture. This was done to reduce water content in the final product. In a typical reaction, 5 g of Glx12-SA was dissolved in 50 mL DMSO in a 100 mL round bottom flask and stirred at room temperature prior to adding 2.7 g of N-hydroxysulfosuccinimide (Thermo Fisher, Waltham, Mass.) and 1.96 mL of DIC or 2.57 grams of DCC to the reaction mixture. The reaction was stirred for 24 hours at room temperature. The following day, the reaction mixture was poured into 450 mL of an ethanol/ether (5/95) to precipitate the product. It should be noted that a higher ether content (95% instead of 50% described earlier in Example 10) was employed in the precipitation solvent to precipitate reaction product from the organic solvent (DMSO) used in this Example. The solvent was decanted from the precipitated product and the precipitated material was washed five times with ethanol. The precipitated product was then dried under reduced pressure in a vacuum oven at room temperature for 24 hours. Successful synthesis was confirmed by $^1$H NMR spectroscopy.

Crosslinking measurements were carried out using dry powder mixtures of the Glx12-sNHS prepared using organic solvent route describe above, PEG-diamine.HCl and potassium tetraborate in an 80:40:50 mass ratio using the protocol described in Example 2 or 5, using saline. A crosslinking time of 35-45 sec was observed. Complete gelation and good flow in saline were observed for all samples tested.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An isolated modified polysaccharide, comprising hydrolyzed, uncrosslinked starch functionalized with electrophilic groups capable of reacting with amine groups, wherein the electrophilic groups comprise a leaving group selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl.

2. The isolated modified polysaccharide of claim 1, wherein the hydrolyzed, uncrosslinked starch functionalized with electrophilic groups is present in an amount of greater than or equal to 50 wt. %.

3. The isolated modified polysaccharide of claim 1, wherein the electrophilic groups comprise N-oxysulfosuccinimidyl.

4. A dried, isolated starch composition, comprising starch functionalized with N-oxysulfosuccinimidyl groups.

5. The dried, isolated starch composition of claim 4, wherein the dried, isolated starch composition has a water solubility of at least 1 wt. % at a temperature of 37° C.

6. A dry, powdered hemostatic composition comprising a modified polysaccharide, the modified polysaccharide comprising:
a first modified polysaccharide component comprising a plurality of polysaccharide chains functionalized with electrophilic groups capable of reacting with amine groups, wherein the first modified polysaccharide component comprises one or more modified polysaccharides chosen from:
a) a plurality of dry, porous, microspheres formed of crosslinked starch functionalized with the electrophilic groups, and
b) hydrolyzed, uncrosslinked starch functionalized with the electrophilic groups; and
a second modified polysaccharide component comprising a plurality of polysaccharide chains functionalized with amine groups; wherein the second modified polysaccharide component comprises one or more modified polysaccharides chosen from:
a) a plurality of dry, porous, microspheres formed of crosslinked starch functionalized with the amine groups, and
b) hydrolyzed, uncrosslinked starch functionalized with the amine groups;
wherein the first and second modified polysaccharide components are able to crosslink with each other to form a hemostatic hydrogel.

7. The dry, powdered hemostatic composition of claim 6, wherein the first modified polysaccharide component comprises a plurality of dry, porous, microspheres formed of crosslinked starch functionalized with the electrophilic groups, and wherein the second modified polysaccharide component comprises a plurality of dry, porous, microspheres formed of crosslinked starch functionalized with the amine groups.

8. The dry, powdered hemostatic composition of claim 6, wherein the first modified polysaccharide component comprises hydrolyzed, uncrosslinked starch functionalized with the electrophilic groups, and wherein the second modified polysaccharide component comprises hydrolyzed, uncrosslinked starch functionalized with the amine groups.

9. A dry, powdered hemostatic composition comprising a modified polysaccharide, the modified polysaccharide comprising:
a first modified polysaccharide component comprising a plurality of polysaccharide chains functionalized with electrophilic groups capable of reacting with amine groups; and
a second modified polysaccharide component comprising a starch functionalized with amine groups, wherein the amine groups are at least two bonds removed from the backbone of the starch.

10. The dry, powdered hemostatic composition of claim 9, wherein the electrophilic groups comprise a leaving group selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl.

11. The dry, powdered hemostatic composition of claim 10, wherein the first modified polysaccharide component comprises hydrolyzed, uncrosslinked starch functionalized with the electrophilic groups.

12. The dry, powdered hemostatic composition of claim 11, wherein the hydrolyzed, uncrosslinked starch functionalized with the electrophilic groups comprises maltodextrin.

13. The dry, powdered hemostatic composition of claim 12, wherein the electrophilic groups comprise N-oxysulfosuccinimidyl.

14. The dry, powdered hemostatic composition of claim 13, wherein the second modified polysaccharide component comprises hydroxyethyl starch functionalized with the amine groups.

15. The dry, powdered hemostatic composition of claim 14, wherein at least some of the amine groups of the hydroxyethyl starch are bound to the hydroxyethyl starch via a linking moiety comprising silicon.

16. The dry, powdered hemostatic composition of claim 13, wherein the second modified polysaccharide component comprises hydroxyethyl starch functionalized with (3-aminopropyl)triethoxy silane.

17. The dry, powdered hemostatic composition of claim 9, wherein the first modified polysaccharide component comprises a starch functionalized with the electrophilic groups, and the electrophilic groups are at least two bonds removed from the backbone of the starch.

18. The dry, powdered hemostatic composition of claim 9, wherein the first modified polysaccharide component comprises a starch functionalized with the electrophilic groups, and the electrophilic groups are at least four bonds removed from the backbone of the starch.

19. The dry, powdered hemostatic composition of claim 9, wherein the second modified polysaccharide component comprises a hydroxyalkyl starch functionalized with the amine groups.

20. The dry, powdered hemostatic composition of claim 9, wherein at least some of the amine groups of the second modified polysaccharide component are bound to the polysaccharide via a linking moiety comprising silicon.

21. The dry, powdered hemostatic composition of claim 9, wherein the second modified polysaccharide component comprises hydroxyethyl starch functionalized with the amine groups.

22. A modified polysaccharide, comprising:
a first modified polysaccharide component comprising a plurality of polysaccharide chains functionalized with electrophilic groups capable of reacting with amine groups, wherein the electrophilic groups comprise a leaving group selected from the group consisting of: N-oxysuccinimidyl, N-oxysulfosuccinimidyl, N-oxymaleimidyl, N-oxyphthalimidyl, nitrophenoxyl, N-oxyimidazolyl, and tresyl; and a second modified polysaccharide component comprising a starch functionalized with amine groups, wherein the amine groups are at least two bonds removed from a backbone of the starch.

23. The modified polysaccharide of claim 22, wherein the second modified polysaccharide component comprises hydroxyethyl starch functionalized with the amine groups.

24. The modified polysaccharide of claim 22, wherein the first modified polysaccharide component comprises hydrolyzed, uncrosslinked starch functionalized with the electrophilic groups.

25. The modified polysaccharide of claim 24, wherein the hydrolyzed, uncrosslinked starch functionalized with the electrophilic groups comprises maltodextrin.

26. The modified polysaccharide of claim 25, wherein the electrophilic groups comprise N-oxysulfosuccinimidyl.

27. The modified polysaccharide of claim 26, wherein the second modified polysaccharide component comprises hydroxyethyl starch functionalized with the amine groups.

28. The modified polysaccharide of claim 27, wherein at least some of the amine groups of the hydroxyethyl starch are bound to the hydroxyethyl starch via a linking moiety comprising silicon.

29. The modified polysaccharide of claim 26, wherein the second modified polysaccharide component comprises hydroxyethyl starch functionalized with (3-aminopropyl) triethoxy silane.

30. A modified polysaccharide, comprising:
a first modified polysaccharide component comprising a plurality of polysaccharide chains functionalized with electrophilic groups capable of reacting with amine groups; and
a second modified polysaccharide component comprising a starch functionalized with amine groups, wherein the amine groups are at least two bonds removed from a backbone of the starch, wherein at least some of the amine groups of the second modified polysaccharide component are bound to the polysaccharide via a linking moiety comprising silicon.

31. The modified polysaccharide of claim 30, wherein the second modified polysaccharide component comprises hydroxyethyl starch functionalized with the amine groups.

32. The modified polysaccharide of claim 30, wherein the second modified polysaccharide component comprises hydroxyethyl starch functionalized with (3-aminopropyl) triethoxy silane.

* * * * *

UNITED STATES PATENT AND TRADEMARK OFFICE
CERTIFICATE OF CORRECTION

PATENT NO. : 11,739,166 B2  
APPLICATION NO. : 17/365749  
DATED : August 29, 2023  
INVENTOR(S) : Keith Greenawalt et al.

Page 1 of 1

It is certified that error appears in the above-identified patent and that said Letters Patent is hereby corrected as shown below:

In the Specification

At Column 73, Line 12:
"3-amino triethoxysilane (APTES)"
Should read:
--APTES--

At Column 74, Line 65:
"3-amino triethoxysilane (APTES)"
Should read:
--APTES--

Signed and Sealed this
Twenty-fourth Day of October, 2023

Katherine Kelly Vidal
*Director of the United States Patent and Trademark Office*